(12) United States Patent
Liu et al.

(10) Patent No.: US 11,021,478 B2
(45) Date of Patent: Jun. 1, 2021

(54) INDOLIZINE DERIVATIVES AND THEIR APPLICATION IN MEDICINE

(71) Applicant: Kind Pharmaceutical, Hangzhou (CN)

(72) Inventors: Dong Liu, Hangzhou (CN); Dongdong Chen, Hangzhou (CN); Biao Deng, Hangzhou (CN); Xiangyun Tu, Hangzhou (CN); Zinan Fang, Hangzhou (CN); Haohao Wu, Hangzhou (CN); Danyan Gu, Hangzhou (CN)

(73) Assignee: KIND PHARMACEUTICAL, Zhejiang (CN)

( * ) Notice: Subject to any disclaimer, the term of this patent is extended or adjusted under 35 U.S.C. 154(b) by 27 days.

(21) Appl. No.: 16/611,838

(22) PCT Filed: May 8, 2018

(86) PCT No.: PCT/CN2018/086025
§ 371 (c)(1),
(2) Date: Nov. 7, 2019

(87) PCT Pub. No.: WO2018/205928
PCT Pub. Date: Nov. 15, 2018

(65) Prior Publication Data
US 2020/0165242 A1    May 28, 2020

(30) Foreign Application Priority Data

May 9, 2017    (CN) .......................... 201710322377.2

(51) Int. Cl.
C07D 471/04    (2006.01)
C07D 491/20    (2006.01)
A61P 7/00      (2006.01)

(52) U.S. Cl.
CPC .............. *C07D 471/04* (2013.01); *A61P 7/00* (2018.01); *C07D 491/20* (2013.01)

(58) Field of Classification Search
CPC ........ C07D 471/04; C07D 491/20; A61P 7/00
USPC ...................................................... 514/291
See application file for complete search history.

(56) References Cited

U.S. PATENT DOCUMENTS

2010/0047367 A1    2/2010    Deng et al.

FOREIGN PATENT DOCUMENTS

| CN | 101460223 A | 6/2009 |
|---|---|---|
| CN | 102264740 A | 11/2011 |
| CN | 104903295 B | 9/2017 |
| CN | 107739378 A | 2/2018 |
| EP | 0661269 A1 | 12/1994 |
| JP | 2006527200 A | 11/2006 |
| JP | 2011037841 A | 2/2011 |
| JP | 2012500802 A | 1/2012 |
| JP | 2012500850 A | 1/2012 |
| JP | 2012508752 A | 4/2012 |
| JP | 2012532897 A | 12/2012 |
| JP | 2016503052 A | 2/2016 |
| WO | 9405662 | * 3/1994 |
| WO | WO2004108661 A1 | 12/2004 |
| WO | WO 2004108681 A1 | 12/2004 |
| WO | WO2007070359 A2 | 6/2007 |
| WO | WO2007150011 A2 | 12/2007 |
| WO | WO2008076425 A1 | 6/2008 |
| WO | WO2008076427 A3 | 6/2008 |
| WO | WO 2008134553 A1 | 11/2008 |
| WO | WO2010022240 A1 | 2/2010 |
| WO | WO2011007856 A1 | 1/2011 |
| WO | WO2011042477 A1 | 4/2011 |
| WO | WO2012006472 A1 | 1/2012 |
| WO | WO2013043621 A1 | 3/2013 |
| WO | WO2014102818 A1 | 7/2014 |
| WO | WO 2014102818 A1 | 7/2014 |

OTHER PUBLICATIONS

Addison, "Is Routine Ordering of Both Hemoglobin and Hematocrit Justifiable?", Canada Medical Association Journal, 1966; 95(19): 974-975.

Arrieta et al., "NMR investigation and theoretical studies on the tautomerism of β,β'-tricarbonyl compounds", Tetrahedron, 2013; 69(42): 8872-8877.

Basílio et al., "Tautomeric Equilibria of 3-Formylacetylacetone: Low-Temperature NMR Spectroscopy and ab Initio Calculations", Journal of Organic Chemistry, 2009; 74(13): 4878-4881.

Cunliffe et al., "Novel Inhibitors of Prolyl 4-Hydroxylase. 3. Inhibition by the Substrate Analogue N-Oxaloglycine and Its Derivatives", Journal Medicinal Chemistry, 1992; 35(14): 2652-2658.

Dowell et al., "Novel Inhibitors of Prolyl 4-Hydroxylase", Journal of Medicinal Chemistry, 1992; 35(5): 800-804.

Dvornikova et al., "Synthesis of 2- and 3-Substituted N-Methylpyrroles", Synlett, 2002; 7: 1152-1154.

(Continued)

*Primary Examiner* — Niloofar Rahmani
(74) *Attorney, Agent, or Firm* — James S. Keddie; Bozicevic, Field & Francis LLP

(57) ABSTRACT

This invention relates to indolizine derivatives and their use in medicine. In particular, the present invention discloses novel substituted indolizine derivatives of formula I, or an isotopically labeled compound thereof, or an optical isomer thereof, a geometric isomer thereof, a tautomer thereof or a mixture of various isomers, or a pharmaceutically acceptable salt thereof, or a prodrug thereof. The invention also relates to the use of these compounds in medicine.

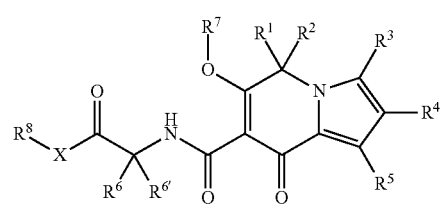

15 Claims, No Drawings

(56) References Cited

OTHER PUBLICATIONS

Epstein et al., "C. elegans EGL-9 and Mammalian Homologs Define a Family of Dioxygenases that Regulate HIF by Prolyl Hydroxylation", Cell 2001; 107(1): 43-54.

Hales et al., "Novel Inhibitors of Prolyl 4-Hydroxylase. 5. The Intriguing Structure-Activity Relationships Seen with 2,2'-Bipyridine and its 5,5'-Dicarboxylic Acid Derivatives", Journal of Medicinal Chemistry, 1993; 36(24): 3853-3858.

Ivan et al., "HIFalpha Targeted for VHL-Mediated Destruction by Proline Hydroxylation: Implications for O2 Sensing", Science, 2001; 292(5516): 464-468.

Laatsch et al., "Synthese von Pentabrompseudilin, einem cytotoxischen Phenylpyrrol aus Alteromonas luteo-violaceus", Liebigs Annalen Der Chemie, 1989; 9: 863-881.

Luo, "Design, synthesis and biological evaluation of PAC-1 analogues", PHD thesis, Jilin University, China, 2014.

Lovering et al., "Escape from Flatland: Increasing Saturation as an Approach to Improving Clinical Success", Journal of Medical Chemistry, 2009; 52(21): 6752-6756.

Munday, "Amino-acids of the Cyclohexane Series. Part I.", Journal of the Chemical Society, 1961; 4372-4379.

Oehme et al., "A nonradioactive 96-well plate assay for the detection of hypoxia-inducible factor prolyl hydroxylase activity", Analytical Biochemistry, 2004; 330(1): 74-80.

"Organic Chemistry Study Guide and Typical Examples (I), Chapter 7 Aromatic Hydrocarbons", Xinhua College of Sun Yat-Sen University, Study Gide posted to the internet of unknown origin. Downloaded on Jan. 28, 2021.

PubChem access No. 11256664: Roxadustat. Downloaded from the NCBI website on Jan. 27, 2021.

Report of a WHO Scientific Group, "Nutritional Anaemias", World Health Organization Technical Report Series No. 405, 1968; 405: 5-37.

Sajiki et al., "Complete Replacement of H2 by D2 via Pd/C-Catalyzed H/D Exchange Reaction", Organic Letters, 2004; 6(20): 3521-3523.

Semenza et al., "A Nuclear Factor Induced by Hypoxia via De Novo Protein Synthesis Binds to the Human Erythropoietin Gene Enhancer at a Site Required for Transcriptional Activation", Molecular and Cellular Biology, 1992; 12(12): 5447-5454.

Semenza, "Targeting HIF-1 for Cancer Therapy", Nature Review Cancer, 2003; 3(10): 721-732.

Stotani et al., "Design and Synthesis of Fsp(3)-Rich, Bis-Spirocyclic-Based Compound Libraries for Biological Screening", ACS Combinatorial Science, 2016; 18(6): 330-336.

Notice of acceptance issued for Australian Application No. 2018264313, dated May 26, 2020.

Office Action issued for Australian Application No. 2018264313, dated Feb. 24, 2020.

Notice of acceptance issued for China Application No. 201810434087.1, dated Jan. 25, 2021.

Office Action issued for China Application No. 201810434087.1, dated Jan. 21, 2020.

Office Action issued for China Application No. 201810434087.1, dated Jul. 8, 2020.

Office Action issued for China Application No. 201810434087.1, dated Oct. 14, 2020.

Extended European Search Results issued for European Application No. 18798694.8 dated Dec. 4, 2020.

Notice of Reasons for Refusal issued for Japan Application No. 2020-513389 dated Oct. 19, 2020.

International Search Report and Written Opinion of the International Searching Authority issued for International Application No. PCT/CN2018/086025, dated Aug. 16, 2018.

\* cited by examiner

INDOLIZINE DERIVATIVES AND THEIR APPLICATION IN MEDICINE

CROSS-REFERENCE TO RELATED APPLICATION

This application is a National Stage of International Patent Application No. PCT/CN2018/086025, filed on May 8.2018, which claims priority to Chinese Patent Application No. 201710322377.2, filed on May 9, 2017, both of which are incorporated herein by reference in their entirety.

TECHNICAL FIELD

The present disclosure belongs to the field of medicine and relates to an indolizine derivative, its preparation and its application in medicine. In particular, the present disclosure relates to treatment of diseases associated with HIF prolyl hydroxylase, such as anemia and the like.

BACKGROUND

Anemia is a disease caused by a decrease in the number of erythrocytes or a decrease in erythrocyte hemoglobin content in the body's blood. Because the main function of hemoglobin is to carry oxygen to various organs for use, low levels of hemoglobin will directly lead to insufficient oxygen supply in various body's organs. Since the normal physiological activities of body depend on full utilization of oxygen, various degrees of anemia can cause various clinical symptoms. Common anemia secondary diseases include cardiovascular diseases such as heart failure, atrial fibrillation, angina pectoris and the like, urinary system diseases such as renal failure and proteinuria, and nervous system diseases such as dizziness, headache, tinnitus, vertigo, lack of energy, fatigue and lethargy, irritability, and inattention. Patients with severe anemia may experience fainting, digestive diseases such as loss of appetite and constipation, reproductive system diseases such as decline of sexual desire and irregular menstruation and so on. Not only can anemia seriously affect patient's health and quality of life, but also anemia can even threaten patient's life if it is not improved in time.

There are many causes of anemia, which usually include decreased production of erythropoietin (EPO). Chronic kidney disease (CKD) causes a decrease in erythropoietin synthesis, so most patients with CKD have anemia. In addition, after receiving radiotherapy and chemotherapy, cancer patients may also suffer from anemia because their bone marrow hematopoietic stem cells are suppressed. Some antiviral drugs such as drugs for treating hepatitis C and HIV and inflammation can also cause anemia.

Stabilizing hypoxia-inducible factor (HIF) by inhibiting HIF prolyl hydroxylase can increase erythropoietin production (Cell, 2001, 107, 43-54). HIF is a transcriptional regulator that plays a crucial role in regulating oxygen balance in body's hypoxia response (Molecular Cellular Biology 1992, 12, 5447-5454). HIF-1 is a heterodimer that up-regulates expression of many genes when it is linked to the promoter region of a hypoxia-responsive element (HRE) (Nature Reviews Cancer 2003, 3, 721-732). Proteins encoded by genes regulated by HIF-1 can cause many biological effects, including erythropoiesis, angiogenesis, vasodilation, glycolysis, immune regulation, neuroprotection, cardiac ischemic protection, cerebral ischemia protection and so on. In the case of normal oxygen levels, HIF-1α subunit is hydroxylated at proline residue by prolyl hydroxylase. The hydroxylated HIF-1α is linked to von Hippel Lindau protein and then degraded by proteosome via ubiquitination. In the absence of oxygen, inhibitory activity of prolyl hydroxylase is suppressed, so HIF-1α subunit is stabilized, the content of HIF-1α subunit is increased, and the levels of genes regulated by the subunit and erythropoietin are elevated (Science 2001, 292, 464-468).

Collagen prolyl hydroxylase inhibitors have been disclosed in the literatures, for example, J. Med. Chem. 1992, 35, 800-804; J. Med. Chem. 1992, 35, 2652-2658; J. Med. Chem 1993, 36, 3853-3858; and Patent document EP 661 269. In the field of prolyl hydroxylases associated with HIFs, there are also patent literatures disclosing such type of inhibitors, such as WO2004108681, WO2007070359, WO2007150011, WO2008076425, WO2011007856, WO201206472, WO2013043621, WO2014102818, and the like. Most of the prolyl hydroxylase inhibitors associated with HIFs in these patents are mimics of 2-oxoglutaric acid.

However, to date, no HIF prolyl hydroxylase inhibitor drugs associated with HIFs has been approved for market entry. Therefore, it is still necessary to find a novel prolyl hydroxylase inhibitor, so that patients with diseases associated with HIFs may have various options in the future.

SUMMARY

1. Compounds of the Present Disclosure

It is an object of the present disclosure to provide a novel HIF prolyl hydroxylase inhibitor. Another object of the present disclosure is to provide a novel compound for treating or preventing a disease associated with HIFs such as anemia.

Accordingly, one aspect of the present disclosure provides a compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof, wherein the compound of Formula I is as follows

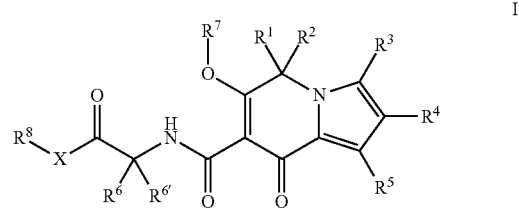

in which
$R^1$ and $R^2$ are each independently selected from the group consisting of cyano, alkyl, heterocyclyl, alkenyl, alkynyl, aryl, heteroaryl, acyl, amino, $R^9O-$, $R^9S-$, $R^9(O=)S-$, and $R^9(O=)_2S-$, wherein $R^9$ is alkyl, heterocyclyl, alkenyl, alkynyl, aryl or heteroaryl; and wherein the alkyl, heterocyclyl, alkenyl, alkynyl, aryl, heteroaryl, acyl, and amino are optionally substituted by one or more substituents wherein the substituents are independently selected from the group consisting of halo, cyano, hydroxy, amino, carboxy, acyl, alkyl, heterocyclyl, alkenyl, alkynyl, aryl, heteroaryl, $=O$, $=S$, $-SH$, $R^{10}O-$, $R^{10}S-$, $R^{11}(O=)S-$, and $R^{11}(O=)_2S-$, and wherein $R^{11}$ is alkyl, heterocyclyl, alkenyl, alkynyl, aryl, or heteroaryl; or $R^1$ and $R^2$ are taken together to form a ring;

$R^3$, $R^4$ and $R^5$ are each independently selected from the group consisting of hydrogen, halogen, hydroxy, carboxy, cyano, amino, acyl, alkyl, heterocyclyl, alkenyl, alkynyl, aryl, heteroaryl, $R^{11}O-$, $R^{11}S-$, $R^{11}(O=)S-$, and $R^{11}(O=)_2S-$, wherein $R^{11}$ is an alkyl group, a heterocyclyl group, an alkenyl group, an alkynyl group, an aryl group or a heteroaryl group; wherein the alkyl, heterocyclyl, alkenyl, alkynyl, aryl, heteroaryl, acyl, and amino group are optionally substituted by one or more substituents wherein the substituents are independently selected from the group consisting of halogen, cyano, hydroxy, amino, carboxy, acyl, alkyl, heterocyclyl, alkenyl, alkynyl, aryl, heteroaryl, $=O$, $=S$, $-SH$, $R^{12}S-$, $R^{12}(O=)S-$, and $R^{12}(O=)_2S-$, and wherein $R^{12}$ is alkyl, heterocyclyl, alkenyl, alkynyl, aryl, or heteroaryl;

$R^6$ and $R^{6'}$ are each independently selected from the group consisting of hydrogen and optionally substituted alkyl;

$R^7$ is selected from the group consisting of hydrogen, alkyl and acyl; wherein the alkyl and acyl are optionally substituted by the following groups: halogen, cyano, hydroxy, amino, carboxy, acyl, alkyl, heterocyclyl, alkenyl, alkynyl, aryl, heteroaryl, $=O$, $=S$, $-SH$, $R^{13}O-$, $R^{13}S-$, $R^{13}(O=)S-$, and/or $R^{13}(O=)_2S-$, wherein $R^{13}$ is alkyl, heterocyclyl, alkenyl, alkynyl, aryl, or heteroaryl;

$R^8$ is selected from the group consisting of hydrogen, alkyl and $-OC(O)R^{14}$, wherein $R^{14}$ is alkyl, heterocyclyl, alkenyl, alkynyl, aryl or heteroaryl; wherein the alkyl, heterocyclyl, alkenyl, alkynyl, aryl, or heteroaryl group is optionally substituted with the following groups: halogen, cyano, hydroxy, amino, carboxy, acyl, alkyl, heterocyclyl, alkenyl, alkynyl, aryl, heteroaryl, $=O$, $=S$, $-SH$, $R^{15}S-$, $R^{15}(O=)S-$, and/or $R^{15}(O=)_2S-$; wherein $R^{15}$ is alkyl, heterocyclyl, alkenyl, alkynyl, aryl, or heteroaryl; and X is an oxygen atom or a sulfur atom or NH.

Another aspect of the present disclosure provides a compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof, wherein the compound of Formula I is as follows

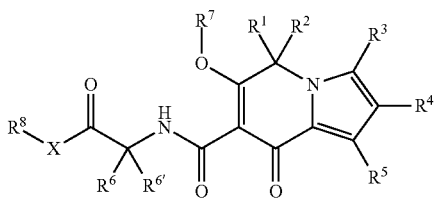

I in which $R^1$ and $R^2$ are independently selected from the group consisting of cyano, C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members, heteroaryl containing 5 to 14 ring members, C1-C12 acyclic alkyl $-C(=O)-$, C2-C12 acyclic alkenyl-$C(=O)-$, amino, $R^9O-$, $R^9S-$, $R^9(O=)S-$, and $R^9(O=)_2S-$, wherein $R^9$ is C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members; wherein the above C1-C12 acyclic alkyl group, C2-C12 acyclic alkenyl group, C2-C12 acyclic alkynyl group, C6-C14 aryl group, C3-C8 cycloalkyl group, C3-C8 cycloalkenyl, heterocycloalkyl having 3 to 8 ring members, heterocycloalkenyl having 3 to 8 ring members, heteroaryl having 5 to 14 ring members, C1-C12 acyclic alkyl-$C(=O)-$, C2-C12 acyclic alkenyl-$C(=O)-$, and amino group are optionally substituted by 1 to 3 substituents wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, heteroaryl-O— having 5 to 14 ring members, C1-C6 acyclic alkyl-S—, C3-C8 cycloalkyl-S—, C2-C6 acyclic alkenyl-S—, C2-C6 acyclic alkynyl —S—, C3-C8 cycloalkenyl-S—, C6-C14 aryl-S—, heteroaryl-S— having 5 to 14 ring members, heterocycloalkyl having 3 to 8 ring members, heterocycloalkenyl having 3 to 8 ring members, $=O$, $=S$, $-SH$, $-CF_3$, $-CO_2C_1-C_6$ acyclic alkyl, C1-C6 acyclic alkyl-S—, C1-C6 acyclic alkyl (O=)S— and C1-C6 acyclic alkyl $(O=)_2S-$; or $R^1$ and $R^2$ are taken together to form an optionally substituted cycloalkane ring, cycloalkylene ring, heterocycloalkane ring, or heterocycloalkylene ring having 3 to 8 ring members;

$R^3$, $R^4$ and $R^5$ are each independently selected from the group consisting of hydrogen, halogen, hydroxy, carboxy, cyano, C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members, heteroaryl having 5 to 14 ring members, C1-C12 acyclic alkyl-$C(=O)-$, C2-C12 acyclic alkenyl-$C(=O)-$, amino, $R^{11}O-$, $R^{11}(O=)S-$, and $R^{11}(O=)_2S-$ wherein $R^{11}$ is C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3-8 ring members, or heterocycloalkenyl having 3 to 8 ring members; wherein the above C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members, heteroaryl having 5 to 14 ring members, C1-C12 acyclic alkyl-$C(=O)-$, C2-C12 acyclic alkenyl-$C(=O)-$, and amino are optionally substituted with from 1 to 3 substituents wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, heteroaryl-O— having 5 to 14 ring members, C1-C6 acyclic alkyl-S—, C3-C8 cycloalkyl-S—, C2-C6 acyclic alkenyl-S—, C2-C6 acyclic alkynyl-S—, C3-C8 cycloalkenyl-S—, C6-C14 aryl-S—, heteroaryl-S— having 5 to 14 ring members, heterocycloalkyl having 3 to 8 ring members, heterocycloalkenyl having 3 to 8 ring members, $=O$, $=S$, $-SH$, $-CF_3$, $-CO_2C_1-C_6$ acyclic alkyl group, C1-C6 acyclic alkyl-S—, C1-C6 acyclic alkyl (O=)S— and C1-C6 acyclic alkyl $(O=)_2S-$;

$R^6$ and $R^{6'}$ are each independently selected from the group consisting of hydrogen, C1-C6 acyclic alkyl and C3-C8 cycloalkyl; the above C1-C6 acyclic alkyl and C3-C8 cycloalkyl are optionally substituted by 1 to 3 substituents wherein the substituents are independently selected from the group consisting of hydroxy, halogen, cyano, amino, carboxy, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-0-, C3-C8 cycloalkenyl-O—, C6-C14 aryl-O—, and heteroaryl-O— having 5 to 14 ring members; $R^7$ is selected from the group consisting of hydrogen, C1-C6 acyclic alkyl, C3-C8 cycloalkyl, C1-C6 acyclic alkyl-C(=O)—, and C2-C6 acyclic alkenyl-C(=O)—; wherein the C1-C6 acyclic alkyl, C3-C8 cycloalkyl, C1-C6 acyclic alkyl-C(=O)—, and C2-C6 acyclic alkenyl-C(=O)— are optionally substituted by 1 to 3 substituents, wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, and heteroaryl-O— having 5 to 14 ring members; $R^8$ is selected from the group consisting of hydrogen, C1-C12 acyclic alkyl, C3-C8 cycloalkyl and —OC(O)—C1-C12 acyclic alkyl; wherein the C1-C12 acyclic alkyl, C3-C8 cycloalkyl and OC(O)—C1-C12 acyclic alkyl group are optionally substituted by 1 to 3 substituents, wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-0-, C2-C6 acyclic alkynyl-O—, C3-C8 cycloalkenyl-O—, C6-C14 aryl-O—, and heteroaryl-O-having 5 to 14 ring members; and X is an oxygen atom or a sulfur atom or NH.

In some preferred embodiments of the invention, in Formula I, $R^1$ and $R^2$ are each independently selected from cyano, amino, and unsubstituted C1-C6 acyclic alkyl; or R1 and R2 are taken together to form an optionally substituted cycloalkane ring or heterocycloalkane ring having 3-8 ring members.

In some preferred embodiments of the invention, in Formula I, $R^1$ and $R^2$ are each independently selected from methyl and ethyl; or R1 and R2 are taken together to form a cyclopropane ring, a cyclobutane ring, a cyclohexane ring, a methylcyclohexane ring, a cycloheptane ring, tetrahydrofuran ring or tetrahydropyran ring.

In some preferred embodiments of the invention, in Formula I, $R^3$, $R^4$ and $R^5$ are each independently selected from the group consisting of hydrogen, halogen, hydroxy, carboxy, cyano, amino, C1-C6 acyclic alkyl, C6-C14 aryl, C3-C8 cycloalkyl, C1-C6 acyclic alkyl —O—, and heteroaryl having 5 to 14 ring members; wherein the above C1-C6 acyclic alkyl, C6-C14 aryl, C3-C8 cycloalkyl, C1-C6 acyclic alkyl-O—, and amino are optionally substituted by 1 to 3 substituents, wherein the substituents are independently selected from the group consisting of hydroxyl, halogen, cyano, amino, carboxyl, C6-C14 aryl and C1-C6 acyclic alkyl.

In some preferred embodiments of the invention, in Formula I, $R^3$, $R^4$ and $R^5$ are each independently selected from the group consisting of hydrogen, halogen, hydroxy, carboxy, cyano, amino, methyl, ethyl, propyl, butyl, phenyl, benzyl, tolyl, methoxyphenyl, chlorophenyl, fluorophenyl, bromophenyl, cyclopropyl, cyclobutyl, cyclopentyl, cyclohexyl and pyridyl.

In some preferred embodiments of the invention, in Formula I, $R^6$ and $R^{6'}$ are independently selected from hydrogen, unsubstituted C1-C6 acyclic alkyl, unsubstituted C3-C8 cycloalkyl, and C1-C6 acyclic alkyl substituted by 1-3 halogens.

In some preferred embodiments of the invention, in Formula I, $R^6$ and $R^{6'}$ are independently selected from the group consisting of hydrogen, methyl, ethyl, propyl, cyclopropyl, and cyclobutyl.

In some preferred embodiments of the invention, in Formula I, $R^7$ is selected from the group consisting of hydrogen, unsubstituted C1-C6 acyclic alkyl, unsubstituted C1-C6 acyclic alkyl-C(=O)— and unsubstituted C2-C6 acyclic alkenyl-C(=O)—.

In some preferred embodiments of the invention, in Formula I, $R^7$ is selected from the group consisting of hydrogen, methyl, ethyl, formyl, and acetyl.

In some preferred embodiments of the invention, in Formula I, $R^8$ is selected from the group consisting of hydrogen, C1-C6 acyclic alkyl, and —OC(O)—C1-C12 acyclic alkyl; wherein the C1-C6 acyclic alkyl and —OC(O)—C1-C12 acyclic alkyl are optionally substituted by 1 to 3 substituents, wherein the substituents are independently selected from hydroxy, halo, cyano, amino, carboxy, C1-C6 acyclic alkyl and C1-C6 acyclic alkyl-O—.

In some preferred embodiments of the invention, in Formula I, $R^8$ is selected from the group consisting of hydrogen, methyl, ethyl, propyl, butyl, pentyl, formyloxy, acetoxy, propionyloxy, butyryloxy and pentanoyloxy.

In some preferred embodiments of the invention, in Formula I, X is an oxygen atom.

In the various preferred embodiments above, the preference for each substituent may be combined with one another, and various combinations thereof are within the scope of the invention.

In the most preferred embodiments of the invention, the compound of Formula I is each specific compound shown in Examples 1 to 71 herein.

As used herein, "a compound as shown by Formula I" or "a compound of Formula I" or "a compound of the invention" or "a compound according to the invention" also encompasses any optical isomer, geometric isomer, tautomer or a mixture of various isomers of the compound of Formula I.

The term "an optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, and a Z isomer. A geometric isomer comprises a cis isomers, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state. As used herein, "a compound as shown by Formula I" also encompasses any tautomer of the compound of formula I. Specifically, the inventors have discovered that the compound of Formula I may have the following tautomers:

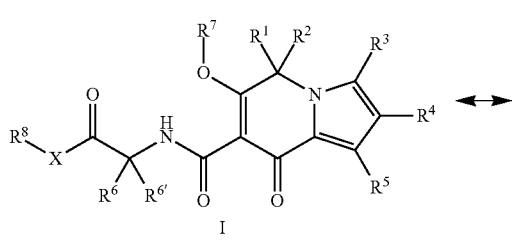

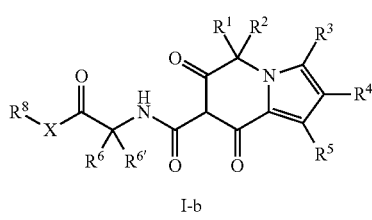 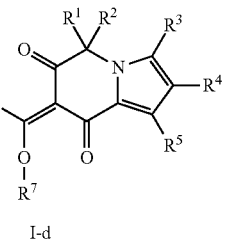

I-b    I-c    I-d

Thus, unless otherwise indicated, reference to "a compound as shown by Formula I" or "a compound of Formula I" or "a compound of the invention" or "a compound according to the invention" herein also encompasses the compound as shown by any of the above Formula Ia, Ib, Ic, or Id. Likewise, a particular compound represented by a particular structural Formula in any example herein also includes tautomers thereof in the form of I-a, I-b, I-c, or I-d.

Unless otherwise indicated, reference to "a compound as shown by Formula I" or "a compound of Formula I" or "a compound of the invention" or "a compound according to the invention" herein also encompasses isotopically-labeled compounds obtained by replacing any atom of the compound with its isotopic atom.

The invention comprises all pharmaceutically acceptable isotopically-labeled compounds of Formula I wherein one or more atoms are replaced by atoms having the same atomic number but different atomic mass or mass number than those normally found in nature.

Examples of isotopes suitable for inclusion in the compounds of the invention include isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulphur, such as $^{35}$S.

Certain isotopically-labelled compounds of formula (I), for example, those incorporating a radioactive isotope, are useful in drug and/or substrate tissue distribution studies. The radioactive isotopes deuterium, i.e. $^2$H, tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, or tritium, i.e. $^3$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Certain compounds of the invention may exist in unsolvated form as well as solvated forms, including hydrated forms. In general, the compounds of formula I, whether present in solvated form or in unsolvated form, are included within the scope of the invention.

Certain compounds of the invention may exist in different crystalline or amorphous forms, and the compounds of Formula I present in any form, are included within the scope of the invention.

To avoid ambiguity, the definitions of the terms used herein are given below. Unless otherwise stated, the meanings of the terms used herein are as follows.

The term "hydroxy" refers to —OH.
The term "halogen" or "halo" refers to —F, —Cl, —Br, or —I.
The term "amino" refers to —NH$_2$.
The term "cyano" refers to —CN.
The term "carboxy" refers to —C(=O)OH.
The term "substituted" means that one or more (preferably 1 to 5, more preferably 1 to 3) hydrogen atoms in a group are independently replaced by a corresponding number of substituents.

The term "independently" means that when the number of substituents is more than one, these substituents may be the same or different.

The term "optional" or "optionally" means that the event described therein may or may not occur. For example, an "optionally substituted" group means that the group may be unsubstituted or substituted.

The term "heteroatom" as used herein refers to oxygen (O), nitrogen (N), or S(O)$_m$ in which m may be 0, 1 or 2, i.e. a sulfur atom S, or a sulfoxide group SO, or a sulfonyl group S(O)$_2$).

The term "alkyl" refers to a group formed by removing a hydrogen atom at any carbon atom from a saturated hydrocarbon consisting solely of two elements, C and H. The "alkyl group" described herein includes an acyclic alkyl group such as a linear alkyl group or a branched alkyl group; and a cycloalkyl group such as a monocyclic alkyl group, a spirocycloalkyl group, a fused cycloalkyl group, or a bridged cycloalkyl group. The alkyl group may be unsubstituted or substituted.

The "alkyl" as used herein includes an optionally substituted acyclic alkyl group which preferably has from 1 to 20 carbon atoms, more preferably from 1 to 12 carbon atoms, and most preferably from 1 to 6 carbon atoms; for example, methyl, ethyl, n-propyl, isopropyl, n-butyl, sec-butyl, isobutyl, tert-butyl, n-pentyl, n-hexyl, chloromethyl, fluoroethyl, trifluoromethyl or 1,1,1-trifluoroethyl and the like.

The "alkyl" as used herein also includes an optionally substituted cycloalkyl (e.g., C3-C20 cycloalkyl or C3-C12 cycloalkyl or C3-C8 cycloalkyl), for example, cyclopropyl, cyclobutyl, cyclopentyl, cyclohexyl, cycloheptyl, cyclooctyl, decalinyl, norbornyl, adamantyl, fluorocyclopropyl, 2-iodocyclobutyl, 2,3-dimethyl cyclopentyl, 2,2-dimethoxycyclohexyl and 3-phenylcyclopentyl and the like.

The "C1-C6 acyclic alkyl", also known as "lower acyclic alkyl", is a subset of alkyl which refers to a linear or branched alkyl group having from 1 to 6 carbon atoms, including, for example, methyl, ethyl, n-propyl, isopropyl, n-butyl, sec-butyl, isobutyl, tert-butyl, n-pentyl, n-hexyl, and the like.

The "alkyl" as used herein is optionally substituted by one or more substituents, wherein the substituents are independently selected from halo, cyano, nitro (—$NO_2$), hydroxy, amino, carboxy, acyl, alkyl, heterocyclyl, alkenyl, alkynyl, aryl, heteroaryl, =O, =S, —SH, $R^{16}$O—, $R^{16}$S—, $R^{16}$(O=)S—, $R^{16}$(O=)$_2$—, wherein $R^{16}$ is alkyl, heterocyclyl, alkenyl, alkynyl, aryl or heteroaryl.

Preferably, the "alkyl" as used herein is optionally substituted with from 1 to 3 substituents, wherein the substituents are independently selected from the group consisting of hydroxy, halo, nitro, cyano, amino, carboxy, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-0-, heteroaryl-O— having 5 to 14 ring members, C1-C6 acyclic alkyl-S—, C3-C8 cycloalkyl-S—, C2-C6 acyclic alkenyl-S—, C2-C6 acyclic alkynyl-S—, C3-C8 cycloalkenyl-S—, C6-C14 aryl-S—, heteroaryl-S— having 5 to 14 ring members, heterocycloalkyl having 3 to 8 ring members, heterocycloalkenyl having 3 to 8 ring members, =O, =S, —SH, —$CF_3$, —$CO_2C_1$-$C_6$ acyclic alkyl group, C1-C6 acyclic alkyl-S—, C1-C6 acyclic alkyl (O=)S— and C1-C6 acyclic alkyl (O=)$_2$S—.

The term "alkenyl" refers to a group formed by removing a hydrogen atom at any carbon atom from a hydrocarbon that consists of only two elements, C and H, and which contains one or more carbon-carbon double bonds without carbon-carbon triple bonds or aromatic bonds. The "alkenyl" as used herein includes an acyclic alkenyl group such as a linear or branched alkenyl group; and also includes a cyclic alkenyl group such as a monocycloalkenyl group, a spirocycloalkenyl group, a fused cycloalkenyl group or a bridged cycloalkenyl group. The alkenyl group may be unsubstituted or substituted.

The "alkenyl" as used herein includes an optionally substituted alkenyl group, preferably having from 2 to 20 carbon atoms, more preferably from 2 to 12 carbon atoms, most preferably from 2 to 6 carbon atoms; for example, vinyl, 1-propenyl, 2-propenyl, 1-butenyl, 2-butenyl, isobutenyl, 1-pentenyl, 2-pentenyl, isopentenyl, 1-hexenyl, 2-hexenyl, 3-hexenyl, isohexenyl, 1-heptenyl, 2-heptenyl, 3-heptenyl, 1-octenyl, 2-octenyl, 3-octenyl, 4-octenyl, 1-decenyl, 1-decenyl, 1-undecenyl, 1-dodecenyl, and the like.

The "alkenyl" as used herein also includes an optionally substituted cycloalkenyl (e.g., C3-C20 cycloalkenyl or C3-C12 cycloalkenyl or C3-C8 cycloalkenyl), for example, cyclobutenyl, cyclopentenyl, cyclohexenyl, cycloheptenyl, cyclobutadienyl, cyclopentadienyl, cycloheptatrienyl, and the like.

The "alkenyl" as used herein is optionally substituted by one or more (e.g., 1-3) substituents, wherein the choice and preference of the substituents are the same as those for the "alkyl".

The term "alkynyl" refers to a group formed by removing a hydrogen atom at any carbon atom from a hydrocarbon that consists of only two elements C and H and which contains one or more carbon-carbon triple bonds without aromatic bonds. The "alkynyl" as used herein includes an acyclic alkynyl group such as a linear or branched alkynyl group, and includes a cycloalkynyl group such as monocycloalkynyl, spirocycloalkynyl, fused cycloalkynyl, or bridged alkynyl. The alkynyl group can optionally contain one or more carbon-carbon double bonds. The alkynyl group may be unsubstituted or substituted.

As used herein, "alkynyl" includes an optionally substituted acylic alkynyl group, preferably having from 2 to 20 carbon atoms, more preferably from 2 to 12 carbon atoms, most preferably from 2 to 6 carbon atoms; for example, acetynyl, propynyl, 1-butynyl, 2-butynyl, isobutynyl, 1-pentynyl, 2-pentynyl, isopenynyl, 3-methyl-3-butynyl, 1-hexynyl, 2-hexynyl, 3-hexynyl, 3-heptynyl, 1-octynyl, 1-nonynyl, 1-decynyl, 1-undecynyl, 1-dodecynyl and the like.

The "alkynyl" as used herein also includes optionally substituted cycloalkynyl (e.g., C8-C18 cycloalkynyl), for example, cyclooctynyl, and the like.

The "alkynyl" as used herein is optionally substituted by one or more (e.g., 1-3) substituents, wherein the choice and preference of the substituents are the same as those for the "alkyl".

The term "heterocyclyl" refers to a group derived from a monocyclic or polycyclic compound that is saturated or contains a carbon-carbon double bond or a carbon-carbon triple bond; which group contains 3 to 20 ring members (preferably 3 to 12 ring members, more preferably 3 to 8 ring members), wherein one or more ring members are selected from heteroatoms, and the remaining ring members are carbon; and any one of the rings has no aromaticity. The "heterocyclyl" as used herein also includes spiroheterocyclyl, fused heterocyclyl and bridged heterocyclyl. The heterocyclyl may be unsubstituted or substituted. The heterocyclyl group may be a heterocycloalkyl group, a heterocycloalkenyl group or a heterocycloalkynyl group. Examples of suitable monocyclic heterocycicyl include, but are not limited to, piperidinyl, pyrrolidinyl, piperazinyl, azetidinyl, azacyclopropyl, morpholinyl, thietanyl, oxacyclopentyl (tetrahydrofuranyl), oxacyclohexyl (tetrahydropyranyl) and the like.

It will be understood that the "heterocyclyl" as used herein is optionally substituted by one or more (e.g., one to three) substituents, wherein the choice and preference of the substituents are the same as those for the "alkyl".

The term "aryl" refers to a group having a conjugated pi-electron system derived from 6 to 14 membered pure carbon monocyclic or fused polycyclic compound. The aryl ring may be fused to a heteroaromatic ring, a heterocyclic ring, cycloalkane, spirocycloalkane, fused cycloalkane, bridged cycloalkane, cycloalkenylene, spirocycloalkene, fused cycloalkene, bridged cycloalkene, cycloalkyne, spirocycloalkyne, fused cycloalkyne or bridged cycloalkyne. The aryl group may be unsubstituted or substituted. Examples thereof include, but are not limited to, phenyl, naphthyl, 2-methylphenyl, 3-methylphenyl, 4-methylphenyl, methoxyphenyl (such as 2-methoxyphenyl, 3-methoxyphenyl, 4-methoxyphenyl), chlorophenyl (such as 2-chlorophenyl, 3-chlorophenyl, 4-chlorophenyl), fluorophenyl (such as 2-fluorophenyl, 3-fluorophenyl, 4-fluorophenyl), bromophenyl (such as 2-bromophenyl, 3-bromophenyl, 4-bromophenyl), 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methyl phenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, and the like.

The "aryl" as used herein are optionally substituted with from 1 to 4 or from 1 to 3 substituents, wherein the choice and preference of the substituents are the same as those for the "alkyl".

The term "heteroaryl" refers to a group derived from an aromatic system containing from 5 to 18 ring members, preferably from 5 to 14 ring members, one or four ring members of which are heteroatoms selected from the group consisting of oxygen, nitrogen and sulfur. The heteroaryl ring may be fused to an aryl ring, a heterocyclic ring, cycloalkane, spirocycloalkane, fused cycloalkane, bridged cycloalkane, cycloalkenylene, spirocycloalkene, fused cycloalkene, bridged cycloalkene, cycloalkyne, spirocycloalkyne, fused cycloalkyne or bridged cycloalkyne. The "heteroaryl" may be unsubstituted or substituted. Examples of heteroaryl groups include, but are not limited to, thienyl, furanyl, pyrrolyl, pyridyl, pyrimidinyl, imidazolyl, pyrazinyl, oxazolyl, thiazolyl, benzothienyl, benzofuranyl, benzoxazolyl, benzimidazolyl, indenyl, quinolyl, isoquinolyl and quinazolinyl, and the like.

The "heteroaryl" as used herein are optionally substituted with from 1 to 4 or from 1 to 3 substituents, wherein the choice and preference of the substituents are the same as those for the "alkyl".

The term "acyl" as used herein refers to RC(=O)—, wherein R is C1-C18 (preferably C1-C12, more preferably C1-C6) alkyl or H. Examples of "acyl" include, but are not limited to, formyl, acetyl, benzoyl, nicotinyl, propionyl, isobutyryl, oxalyl, and the like.

The acyl group RC(=O)— as used herein is optionally substituted by one or more (e.g., 1-3) substituents, wherein the choice and preference of the substituents are the same as those for the "alkyl".

The term "form a ring" as used herein means forming a cyclic structure such as a cycloalkane ring, a cycloalkene ring, a cycloalkyne ring, an aromatic ring, a heterocycloalkane ring, a heterocycloalkene ring, a heterocycloalkyne ring, a heteroaryl ring or the like wherein the cyclic structure may be a monocyclic, bicyclic or polycyclic structure including its fused ring, bridged ring, and spiro ring structure. Particularly, the ring formed by the substituents $R^1$ and $R^2$ herein is preferably a 3- to 12-membered ring, particularly preferably a 3- to 12-membered cycloalkane ring, cycloalkene ring, heterocycloalkane ring, and heterocycloalkene ring, and most preferably a 3- to 8-membered cycloalkane ring, cycloalkene ring, heterocycloalkane ring, and heterocycloalkene ring, such as a cyclopropane ring, a cyclobutane ring, a cyclopentane ring, a cyclohexane ring, a cycloheptane ring, a tetrahydrofuran ring, a tetrahydropyran ring and the like. The ring structure is optionally substituted with one or more (e.g., 1-3) substituents, wherein the choice and preference of the substituents are the same as those for the "alkyl".

Herein, a numerical range relating to the number of substituents, the number of carbon atoms, and the number of ring members represents an enumeration of all integers in the range, and the range is only a simplified representation thereof. For example:

"1-4 substituents" means 1, 2, 3 or 4 substituents;

"1-3 substituents" means a 1, 2 or 3 substituent;

"3 to 12-membered ring" means a 3, 4, 5, 6, 7, 8, 9, 10, 11 or 12-membered ring;

"3 to 8 membered ring" means a 3, 4, 5, 6, 7, or 8 membered ring;

"1-12 carbon atoms" or "C1-C12" means 1(C1), 2 (C2), 3 (C3), 4 (C4), 5 (C5), 6 (C6), 7 (C7), 8 (C8), 9 (C9), 10 (C10), 11 (C11) or 12 (C12) carbon atoms;

"1-6 carbon atoms" or "C1-C6" means 1 (C1), 2 (C2), 3 (C3), 4 (C4), 5 (C5) or 6 (C6) carbon atoms;

"2-6 carbon atoms" or "C2-C6" means 2 (C2), 3 (C3), 4 (C4), 5 (C5) or 6 (C6)carbon atoms;

"C3-C8" means 3 (C3), 4 (C4), 5 (C5), 6 (C6), 7 (C7) or 8 (C8) carbon atoms;

"3 to 8 ring members" means 3, 4, 5, 6, 7, or 8 ring members.

Thus, a numerical range associated with the number of substituents, the number of carbon atoms, and the number of ring members also encompasses any one of its subranges, and each subrange is also considered to be disclosed herein.

2. Application of the Compounds of the Invention

The Inventors have discovered through experimentation that the compounds according to the invention are specific inhibitors of HIF prolyl hydroxylase. The compounds of the present invention provide a synergistic hypoxic response that mimics the organism response to increase erythropoietin and increase hemoglobin levels by inhibiting HIF prolyl hydroxylase. It has been found that the compounds according to the invention are useful for the treatment and/or prophylaxis of diseases associated with HIFs, such as anemia, cardiovascular disease, diabetes, neurological diseases, etc., in particular heart dysfunction, coronary heart disease, angina pectoris, myocardial infarction, stroke, arteriosclerosis, spontaneous hypertension, pulmonary hypertension, malignant hypertension, and peripheral arterial obstructive disease.

In particular, the diseases which are suitable for being treated and/or prevented by the administration of a compound of Formula I include:

Blood-forming diseases such as idiopathic anemia, renal anemia and anemia associated with neoplastic diseases (especially chemotherapy-induced anemia), infectious diseases (especially HIV-infected diseases) or other inflammatory diseases such as rheumatoid arthritis;

Hemorrhagic anemia, iron deficiency anemia, vitamin deficiency anemia (e.g. due to vitamin B12 insufficiency or due to folic acid deficiency), cell hypoplastic and aplastic anemia or hemolytic anemia, anemia caused by iron disease (iron-deficient anemia) or anemia caused by other endocrine diseases (such as hypothyroidosis);

Surgery-related ischemia and its complications after surgery, especially cardiac intervention related to use of cardiopulmonary machines (e.g., bypass surgery, heart valve transplantation), carotid intervention, aortic intervention, and intervention with opening or penetration of skull volume device;

Complications of acute and prolonged cerebral ischemic conditions (e.g. stroke, fetal suffocation);

Cancer and damage to health conditions that occur during cancer treatment, especially those damage to the health conditions that occur after application of cytostatics, antibiotics, and radiation;

Rheumatism and other forms of disease that are considered to be autoimmune diseases, particularly those damage to the health conditions that occur during the course of drug treatment of these diseases;

Eye diseases (e.g. glaucoma), central nervous system diseases (e.g. dementia, chronic pain), chronic kidney disease, renal insufficiency and acute renal failure;

Sexual dysfunction (such as loss of libido);

Diabetes and its complications such as diabetic macroangiopathy and microangiopathy, diabetic nephropathy and neuropathy;

Fibrotic diseases such as fibrosis of heart, lung and liver;

Neurodegenerative diseases such as Alzheimer's disease, Parkinson's disease, bovine spongiform encephalopathy, Creutzfeldt-Jakob disease, Huntington's disease, cerebellar atrophy, and the like; and Ischemic diseases, such as ischemic cerebrovascular disease, ischemicrenaldisease (IRD), ischemic cardiomyopathy (ICM), and the like.

Furthermore, the compounds according to the invention are also suitable for the general treatment and/or prevention during surgery for the purpose of promoting wound healing and reducing recovery time.

The compounds according to the invention are also suitable for in vitro use of increasing hematocrit for the purpose of obtaining blood for pre-operative blood autodonation.

Accordingly, another aspect of the invention relates to a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, for use as a medicament for the treatment and/or prevention of a disease associated with HIFs.

Another aspect of the invention related to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, for the treatment and/or prevention of a disease associated with HIFs.

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for the preparation of a HIF prolyl hydroxylase inhibitor.

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for the manufacture of a medicament for the treatment and/or prophylaxis of a disease associated with HIFs.

Another aspect of the invention relates to a method of treating and/or preventing a disease associated with HIFs, the method comprising administering to a patient in need thereof a therapeutically effective amount of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof.

Another aspect of the invention relates to a method of treating and/or preventing a disease associated with HIFs, the method comprising administering to a patient in need thereof a therapeutically effective amount of a pharmaceutical composition, the pharmaceutical composition comprising a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, and one or more pharmaceutically acceptable carriers, diluents or excipients.

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for wound healing and/or shortening recovery time in surgery.

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for the manufacture of a medicament for use in surgery to accelerate wound healing and/or to reduce recovery time.

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for increasing hematocrit, which use may be for therapeutic purposes, for diagnostic purposes, or for non-therapeutic non-diagnostic purposes (for example, for experimental studies only to increase hematocrit).

Another aspect of the invention relates to a method of obtaining self-donated blood prior to surgery, the method comprising adding a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof to a blood sample.

As used herein, the term "patient" refers to all mammals, including humans. Examples of patients include humans, cows, dogs, cats, goats, sheep, rats, pigs, and rabbits.

As used herein, the term "disease associated with hypoxia-inducible factor" or "disease associated with HIFs" includes, but is not limited to, anemia (such as idiopathic anemia, renal anemia, anemia associated with neoplastic diseases (especially chemotherapy-induced anemia), hemorrhagic anemia, anemia caused by women's menorrhagia, iron deficiency anemia, vitamin deficiency anemia, cell hypoplastic and aplastic anemia, hemolytic anemia, anemia caused by iron disease or anemia caused by hypothyroidism); cardiovascular disease (such as heart dysfunction, coronary heart disease, angina pectoris, myocardial infarction, stroke, arteriosclerosis, spontaneous hypertension, pulmonary hypertension, malignant hypertension, and peripheral arterial obstructive disease), neurological diseases, HIV infections, rheumatoid arthritis, surgery-related ischemia, fetal suffocation, cancer and diseases associated with cancer (such as damage to health conditions that occur after application of cytostatics, antibiotics, and radiation), eye diseases (e.g. glaucoma), central nervous system diseases (e.g. dementia, chronic pain), chronic kidney disease, renal insufficiency and acute renal failure, sexual dysfunction (such as loss of libido), diabetes and its complications such as diabetic macroangiopathy and microangiopathy, diabetic nephropathy, neurodegenerative diseases (such as Alzheimer's disease, Parkinson's disease), ischemic diseases (such as ischemic cerebrovascular disease, ischemicrenaldisease, ischemic cardiomyopathy, and the like) and fibrotic diseases (such as fibrosis of heart, lung and liver).

Preferably, the term "disease associated with hypoxia-inducible factor" refers to anemia, including but not limited to idiopathic anemia, renal anemia, anemia associated with neoplastic diseases (especially chemotherapy-induced anemia), hemorrhagic anemia, iron deficiency anemia, vitamin deficiency anemia, cell hypoplastic and aplastic anemia, hemolytic anemia, anemia caused by iron disease or anemia caused by hypothyroidism and the like; neurodegenerative diseases (such as Alzheimer's disease, Parkinson's disease and the like); ischemic diseases (such as ischemic cerebrovascular disease, ischemicrenaldisease, ischemic cardiomyopathy, and the like) and fibrotic diseases (such as fibrosis of heart, lung and liver).

As used herein, the term "pharmaceutically acceptable salt" of a compound of Formula I refers to an inorganic or organic acid addition salt or an organic or inorganic base addition salt of the compound suitable for use in mammals (i.e., being safe and effective when applied). These salts can be prepared in situ during the final isolation and purification of the compound, or can be obtained by reacting a free form of the pure compound with a suitable organic or inorganic acid or base and then separating the formed salt. Typical salts include hydrobromides, hydrochlorides, sulfates, hydrogen sulfates, nitrates, acetates, oxalates, valerates, oleates, palmitates, stearates, laurates, borates, benzoates, lactates, phosphates, tosylates, citrates, maleates, fumarates, succinates, tartrates, glucoheptonates, lactate, lauryl sulfonate, and the like. These salts may include salts of cations from alkali metals and alkaline earth metals (such as sodium, lithium, potassium, calcium, magnesium, and the like), as well as non-toxic ammonium, quaternary ammonium, and amine cations including, but not limited to, ammonium, tetramethylammonium, tetraethylammonium, methylamine, dimethylamine, trimethylamine, triethylamine, ethylamine, or the like.

As used herein, the term "prodrug" of a compound of Formula I refers to a derivative of the compound suitable for use in mammals (i.e., being safe and effective when applied), which releases the compound of Formula I or a pharmaceutically acceptable salt thereof in vivo after being administered. Examples of prodrugs include amino acid addition salts, esters, amides and the like.

3. Pharmaceutical Compositions and Pharmaceutical Dosage Forms Containing the Compounds of the Invention For therapeutic use, the compounds of Formula I are typically administered to a patient in the form of a pharmaceutical composition comprising at least one of the above compounds as an active ingredient, optionally including a pharmaceutically acceptable adjuvant and/or excipient and/or a pharmaceutically acceptable solid or liquid carrier.

Another aspect of the invention relates to a pharmaceutical composition comprising a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, and one or more pharmaceutically acceptable carriers, adjuvants or excipients.

The present invention also relates to a process for the preparation of the above pharmaceutical composition comprising mixing the compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof with a pharmaceutically acceptable carrier, adjuvant or excipient.

The pharmaceutical compositions of the invention may be formulated as suitable dosage forms for oral, parenteral (including subcutaneous, intramuscular, intradermal and intravenous), bronchial or nasal administration as desire. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula I according to the invention.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The amount of the compound of Formula I in pharmaceutical compositions and dosage forms can be suitably determined by those skilled in the art as needed. For example, the compound of Formula I can be present in a pharmaceutical composition or dosage form in a therapeutically effective amount.

4. Dosage of the Compound of the Invention

As used herein, the term "therapeutically effective amount" is such an amount of the compound of the present invention that, when administered to a patient, effectively delays or eliminates symptoms of the patient or improves health conditions of the patient. The specific application dosage can be determined by doctors according to the specific conditions of patients. The precise dosage to be used depends not only on the route of administration, conditions, severity of conditions to be treated, and various physical factors associated with the subject to be treated, but can also be determined in accordance with the judgment of health care practitioners. In vitro or in vivo tests can be used to help determine the optimal dosage range.

The compounds of the present invention can be administered to a patient at dosage levels in the range of about 0.01 to about 4,000 mg per day or 0.05 to 2000 mg per day, or 0.1 to 1000 mg per day or 0.1 to 500 mg per day. For a normal human adult having a body weight of about 70 kilograms, a dosage may be for example in the range of about 0.001 to about 100 mg per kilogram of body weight per day or in the range of about 0.01 to about 100 mg per kilogram of body weight per day or in the range of about 0.05 to about 50 mg per kilogram of body weight per day. The specific dosage used, however, can vary. The determination of optimum dosages for a particular patient is well-known to those skilled in the art.

The above daily dosages may be administered continuously. For example, it may be administrated every 2 hours, every 6 hours, every 8 hours, every 12 hours, about every 24 hours, or every 2 days, every day, every week every two weeks, every three weeks, every month once or twice a week, or three times a week, or four times a week, or five times a week, or six times a week. The dosage and frequency during the entire course of treatment will be determined based on the judgment of health care practitioners. In one embodiment, the compound of the invention, or a pharmaceutically acceptable salt thereof, is administered concurrently with another therapeutic agent.

In one embodiment, a composition comprising an effective amount of the compound of the invention, or a pharmaceutically acceptable salt thereof, and an effective amount of another therapeutic agent in the same composition can be administered. Effective amounts of other therapeutic agents are known to those skilled in the art. Moreover, determining the range of optimal effective amount of other therapeutic agents is within the skill of the artisan.

5. Method for Preparing the Compound of the Present Invention

The compounds of Formula I of the present invention may be synthesized by a variety of methods familiar to those skilled in the art of organic synthesis. Some exemplary synthetic methods are given below which are well known in the art of synthetic chemistry. The compounds of Formula I are synthesized according to the methods described below, as well as in combination with the methods commonly employed by organic synthetic chemists. The synthetic routes of the compounds in the present invention are not limited to the methods summarized below. The synthesis of certain compounds may require adjustment of operating conditions to meet the requirements of various functional groups. Various protecting groups known to those skilled in the art may be necessary. Purification can be accomplished, if desired, by silica gel column elution with a suitable organic solvent system or by recrystallization. In addition, various specific examples herein also illustrate methods of synthesizing the compounds of the invention.

The compounds of the present invention are mainly synthesized by the following three technical schemes.

Scheme I:

2,5-Dimethyoxytetrahydrofuran is hydrolyzed to 1,4-butanedialdehyde in an acidic aqueous solution at a temperature from room temperature (RT) to 50° C. in which hydrochloric acid is preferably used as acid. And then the resulting mixture is neutralized with a base, preferably with sodium acetate. The neutralized mixture reacts with α,α disubstituted alpha amino acid, preferably at a reaction temperature of from RT to 50° C., thereby obtaining an intermediate I-1. Intermediate I-1 is then reacted with N-hydroxybenzotriazole/DCC to form an activated ester which is then reacted with sodium salt of dimethyl or diethyl malonate to form an intermediate I-2. Intermediate I-1 may also be reacted with CDI, and then further reacted with sodium salt of dimethyl malonate or diethyl ester to form intermediate I-2. Intermediate I-2 is ring-closed under an acidic condition to afford intermediate I-3 in which the preferred acid for this step is methanesulfonic acid, and the preferred temperature is in the range from an ice-water bath temperature to dichloromethane reflux temperature. Intermediate I-3 reacts with glycine or alanine under basic conditions to afford the exemplary compound I-X in which the preferred base is sodium methoxide; and the preferred temperature is in the range from methanol reflux temperature to 150° C.

Scheme II

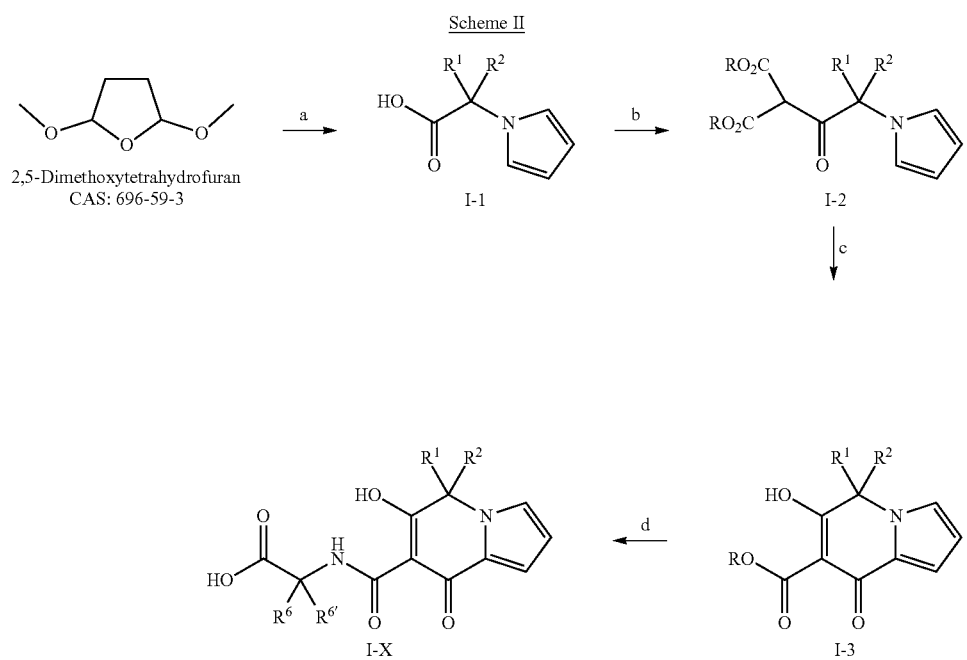

The compound of formula I-4 that is synthesized according to known methods is reacted with an α,α disubstituted α-amino acid under acidic conditions with heating to give intermediate I-5 in which the preferred acid for this step is acetic acid and the preferred temperature for this step is in the range from 80° C. to acetic acid reflux temperature. The conversion of I-5 to I-6 is carried out in a similar manner to the conversion from I-1 to I-2 in Scheme I, and the conversion of I-6 to I-7 is also carried out in a similar manner to the conversion from I-2 to I-3 in Scheme I. The conversion of I-7 to I-Y is also carried out in a similar manner to the conversion from I-3 to I-X.

Scheme III

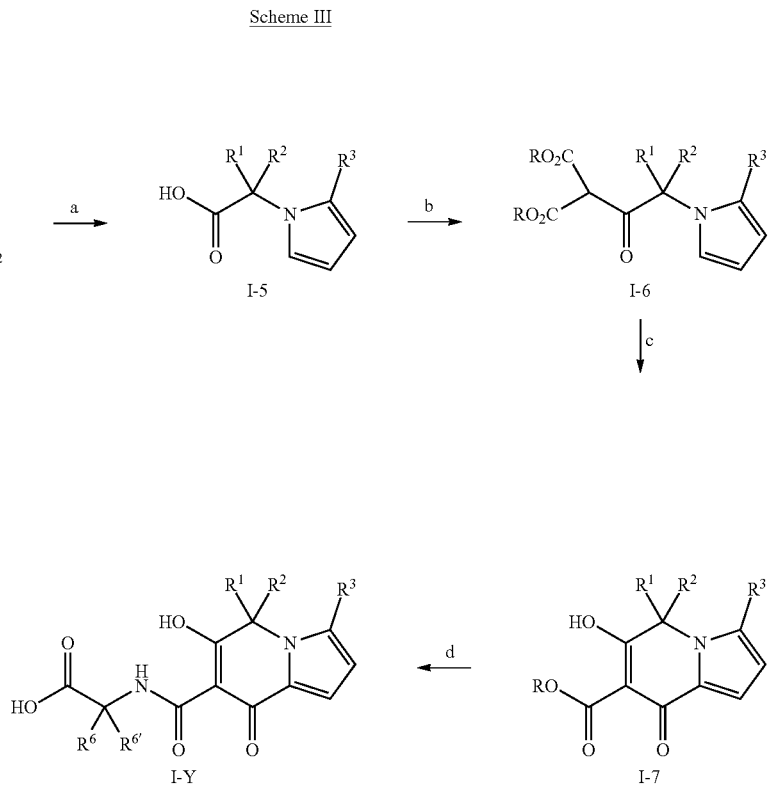

The compound of general formula I-1 reacts with NBS to form a bromide of formula I-8; I-8 then undergoes Suzuki coupling reaction under palladium catalysis to give intermediate I-9; and then conversion of I-9 to I-10 is carried out in a similar manner to the conversion from from I-2 to I-3 in Scheme I. I-10 is ring closed under acidic conditions to give two isomers I-11 and I-12; the conversion of I-11 and of I-12 are carried out in a similar manner to the conversion of I-3 to I-X in Scheme I, to give two isomers of formula I—Z and I-Z', respectively.

deuterated chloroform ($CDCl_3$) and the like were used as solvent, and tetramethylsilane (TMS) was used as an internal standard. LCMS was determined using Shimadzu LCMS-2020 or Thermo UltiMate 3000.

Silica gel plates Huanghai HSGF254 available from Yantai, Shandong, China or plates GF254 from Qingdao, Shandong, China were used as thin-layer chromatography silica gel plates. Generally, Huanghai silica gel with 200 to 300 mesh available from Yantai, Shandong was used as a carrier for column chromatography.

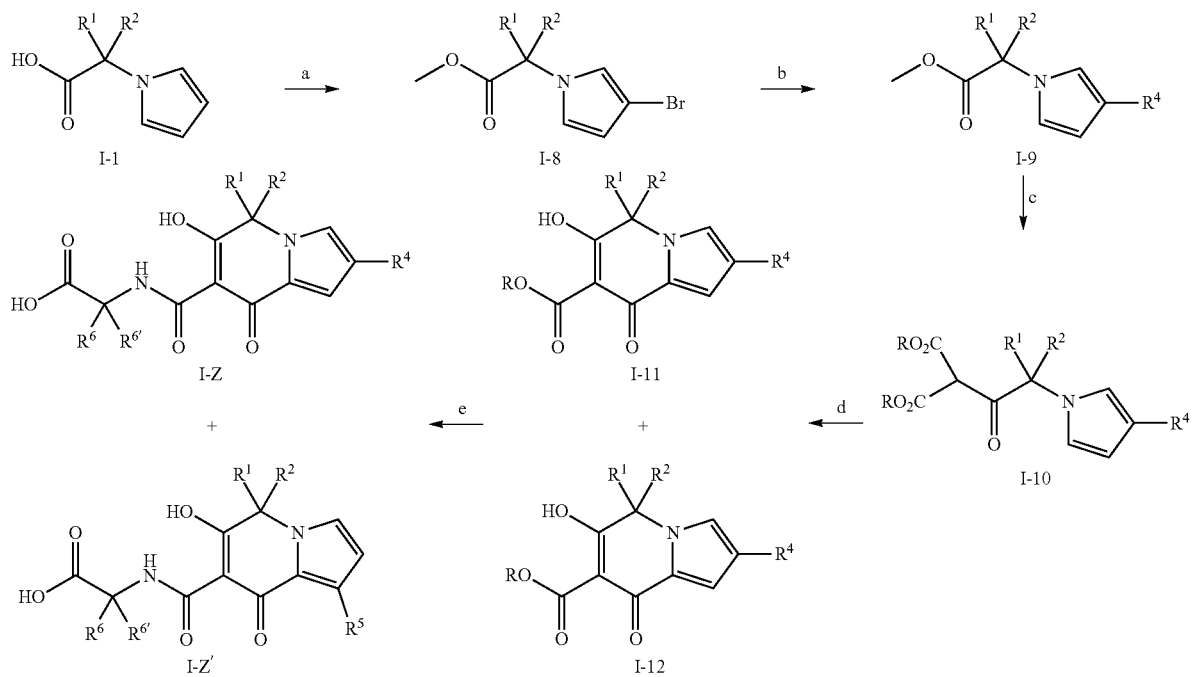

Typical synthetic methods for compounds of I-X, I-Y, I-Z and I-Z' as representative examples of compounds of Formula I are shown above, and those skilled in the art will understand that by appropriately selecting different reactants such as compound I-1 or I-4 having different substituents, and using the same or similar synthetic methods, other compounds of the Formula I with different substituents than that of the I-X, I-Y, I-Z and I-Z' compounds may be obtained.

In addition, particular reaction conditions of the respective steps in the above respective synthesis schemes can be appropriately determined by those skilled in the art in accordance with principles and requirements of conventional chemical reactions. And the reaction conditions given in the following examples of the invention can be used as reference.

DETAILED DESCRIPTION OF EMBODIMENTS

The invention is further illustrated by the following examples; however, these examples do not limit the scope of the invention.

The structures of compounds were determined by liquid chromatography-mass spectrometry (LCMS) or nuclear magnetic resonance (NMR). The NMR chemical shift (δ) is expressed in units of $10^{-6}$ (ppm). The NMR spectra were measured by Bruker-500 nuclear magnetic resonance apparatus in which deuterated dimethyl sulfoxide (dmso-d6), All starting materials used in the present invention were purchased from chemical suppliers or can be synthesized by methods known in literatures.

The abbreviations used in the description of this article are as follows:

DMSO-d6: dimethyl sulfoxide in which six hydrogen atoms are replaced by deuterium $CDCl_3$: Deuterated chloroform CAS: Chemical Abstracts Accession Number NMR: Nuclear Magnetic Resonance LCMS: Liquid Chromatography-Mass Spectrometry ESI: Electrospray ionization ppm: one part per million δ: chemical shift of nuclear magnetic resonance TMS: tetramethylsilane s: nuclear magnetic single peak d: nuclear magnetic double peak t: nuclear magnetic triplet peak br: nuclear magnetic broad peak CDI: carbonyl diimidazole DCC: N,N'-dicyclohexylcarbodiimide NB S: N-bromocyclosuccinimide

Example 1: (6'-Hydroxy-8'-oxo-8'H-spiro[cyclopropane-1,5'-indolizine]-7'-carbonyl) glycine (1)

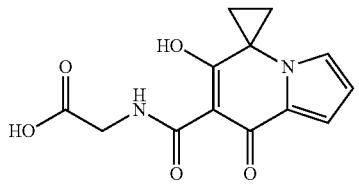

Step 1: 1-(1H-pyrrol-1-yl)cyclopropane-1-carboxylic acid (1a)

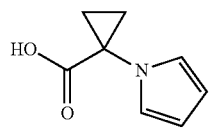

1 ml of concentrated hydrochloric acid was added to a mixture of 2,5-dimethoxytetrahydrofuran (3.16 g, 24 mmol) and 20 ml of water, the resulting mixture was stirred at RT for 1 hour, and then to the reaction mixture sodium acetate solid (3.28 g, 40 mmol) and 1-aminocyclopropane-1-carboxylic acid (2.02 g, 20 mmol) were added successively. The reaction mixture was stirred at RT overnight; then diluted with water, neutralized with 1 M hydrochloric acid to pH 4, and extracted with ethyl acetate. The ethyl acetate layer was separated, and then washed twice with dilute aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 1 g of compound 1a. $^1$H NMR (500 MHz, dmso-d6) δ (ppm): 12.64 (1H, s), 6.78 (2H, t), 5.96 (2H, t), 1.58-1.55 (2H, m), 1.43-1.40 (2H, m).

Step 2: 2-(1-(1H-pyrrol-1-yl)cyclopropane-1-acyl) malonate diethyl ester (1b)

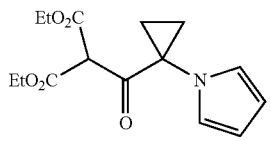

Compound 1a (1.55 g, 10.26 mmol), 1H-benzo[d][1,2,3]triazole-1-ol (1.73 g, 11.29 mmol) and DCC (2.33 g, 11.29 mmol) were mixed in tetrahydrofuran (30 ml) and the resulting mixture was stirred at RT for 16 hours. The solid was removed by filtration, and washed with a small amount of anhydrous tetrahydrofuran. The filtrate and washings were combined.

In a separate reaction flask, diethyl malonate (2.46 g, 15.39 mmol) was dissolved in anhydrous tetrahydrofuran (30 ml), then cooled at an ice water bath, and to this a mixture of mineral oil with purity of 60% and sodium hydride (616 mg) was carefully added under a nitrogen stream and then the resulting reaction mixture was stirred for half an hour. The above combined filtrate and washings were then added to the second reaction flask. The reaction was stirred for 1 hour. The resulting mixture was diluted with water, acidified carefully with 1 M dilute aqueous hydrochloric acid to pH 4, and then extracted with ethyl acetate. The ethyl acetate layer was separated, then washed twice with dilute aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 2.6 g of compound 1b (with a small amount of diethyl malonate). $^1$H NMR (500 MHz, dmso-d6) δ (ppm): 6.84 (2H, t), 6.13 (2H, t), 4.27 (1H, s), 4.12-4.09 (4H, m), 1.70-1.69 (4H, m), 1.19-1.17 (6H, m).

Step 3: Ethyl 6'-Hydroxy-8'-oxo-8'H-spiro[cyclopropane-1,5'-indolizine]-7'-carboxylate (1c)

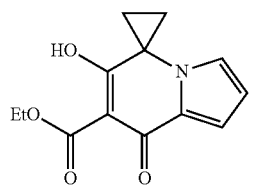

Compound 1b (500 mg) was dissolved in 4 ml of dichloromethane, and 2 ml of methanesulfonic acid was slowly added dropwise at RT. The reaction was stirred for 1 hour. The resulting mixture was extracted with dichloromethane. The dichloromethane layer was separated, then washed twice with diluted aqueous sodium chloride. The separated dichloromethane phase was dried over anhydrous sodium sulfate; filtered to remove the desiccant and then evaporated to dryness on a rotary evaporator. The resulting residue was purified by column chromatograph to yield 240 mg of compound 1c. $^1$H NMR (500 MHz, dmso-d6) δ (ppm): 7.32-7.31 (1H, m), 6.70-6.98 (1H, m), 6.44-6.42 (1H, m), 4.32-4.27 (2H, m), 1.78-1.76 (2H, m), 1.69-1.67 (2H, m), 1.31-1.27 (3H, m).

Step 4: (6'-Hydroxy-8'-oxo-8'H-spiro[cyclopropane-1,5'-indolizine]-7'-carbonyl)glycine (1)

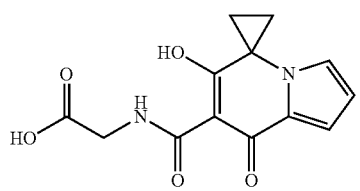

Compound 1c (124 mg), glycine (225 mg) and 0.5 M sodium methoxide solution in methanol (5 mL) were combined and evaporated to dryness. Then, n-propyl alcohol (4 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, and then washed with water; and then dried to give 84 mg of compound 1. $^1$H NMR (500 MHz, dmso-d6) δ (ppm): 18.06 (1H, s), 12.94 (1H, s), 9.99 (1H, s), 7.34 (1H, s), 6.97 (1H, s), 6.44 (1H, s), 4.09-4.08 (2H, d), 1.87 (2H, s), 1.78 (2H, s). LCMS ESI(+): 277 (M+1)$^+$.

Example 2: (6'-Hydroxy-8'-oxo-8'H-spiro[cyclopropane-1,5'-indolizine]-7'-carbonyl)-L-alanine (2)

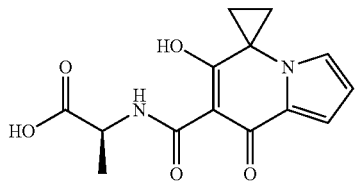

2

Step 1: (6'-Hydroxy-8'-oxo-8'H-spiro[cyclopropane-1,5'-indolizine]-7'-carbonyl)-L-alanine (2)

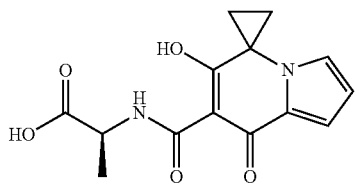

2

Compound 1c (124 mg), L-alanine (250 mg) and 0.5 M sodium methoxide solution in methanol (5 mL) were combined and evaporated to dryness. Then, n-propyl alcohol (4 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, and then washed with water; and then dried to give 98 mg of compound 2. $^1$H NMR (500 MHz, dmso-d6) δ (ppm): 17.99 (1H, s), 13.14 (1H, s), 10.14 (1H, d), 7.36 (1H, s), 6.98 (1H, s), 6.46 (1H, s), 4.53-4.46 (1H, m), 1.89 (2H, s), 1.79 (2H, s), 1.44 (3H, d). LCMS ESI(+): 291 (M+1)$^+$.

Example 3: (6'-Hydroxy-8'-oxo-8'H-spiro[cyclopropane-1,5'-indolizine]-7'-carbonyl)-D-alanine (3)

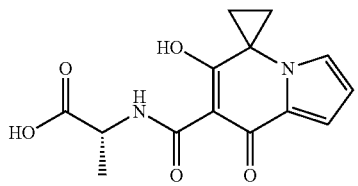

3

Step 1: (6'-Hydroxy-8'-oxo-8'H-spiro[cyclopropane-1,5'-indolizine]-7'-carbonyl)-D-alanine (3)

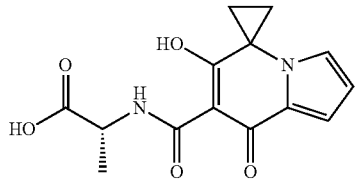

3

Compound 1c (90 mg), D-alanine (192 mg) and 0.5 M sodium methoxide solution in methanol (3.6 mL) were combined and evaporated to dryness. Then, n-propyl alcohol (4 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, washed with water, and then dried to give 98 mg of compound 3. $^1$H NMR (500 MHz, dmso-d6) δ (ppm): 17.99 (1H, s), 13.16 (1H, s), 10.14 (1H, d), 7.35 (1H, s), 6.98 (1H, s), 6.45 (1H, s), 4.51-4.45 (1H, m), 1.88 (2H, s), 1.78 (2H, s), 1.43-1.42 (3H, d). LCMS ESI(+): 291 (M+1)$^+$.

Example 4: (6-Hydroxy-5,5-dimethyl-8-oxo-5,8-dihydroindolizin-7-carbonyl) glycine (4)

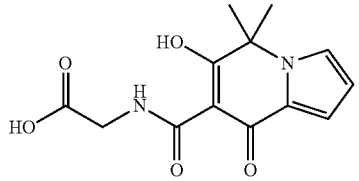

4

Step 1: 2-methyl-2-(1H-pyrrol-1-yl)propionic acid (4)

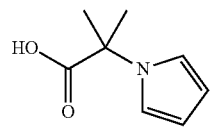

4a 2.9 ml of concentrated hydrochloric acid was added to a mixture of 2,5-dimethoxytetrahydrofuran (7.69 g) and 50 ml of water, the resulting mixture was stirred at RT for 1 hour; and then to the reaction mixture sodium acetate solid (13.2 g) and 2-amino-2-methylpropionic acid (5 g) were added successively. The reaction mixture was stirred at RT overnight; then diluted with water, neutralized with 1 M hydrochloric acid to pH 4; and then extracted with ethyl acetate. The ethyl acetate layer was separated, and then washed twice with dilute aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 5 g of compound 4a. $^1$H NMR (500 MHz, dmso-d6) δ (ppm): 12.78 (1H, s), 6.87 (1H, t), 6.02 (1H, t), 1.68 (6H, s).

Step 2: Dimethyl 2-(2-methyl-2-(1H-pyrrol-1-yl)propanoyl)malonate (4b)

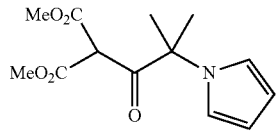

4b

Compound 4a (1.5 g) and CDI (1.9 g) were mixed in tetrahydrofuran (35 ml) and the resulting mixture was stirred at RT for 1 hour. Then dimethyl malonate sodium salt (2.26 g) was added and was stirred for one hour. The resulting mixture was diluted with water and acidified with 1 M diluted hydrochloric acid aqueous solution to pH 4; and then extracted with ethyl acetate. The ethyl acetate layer was separated, and then washed twice with diluted aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 1.03 g of compound 4b. $^1$H NMR (500 MHz, dmso-d6) δ (ppm): 6.89 (2H, t), 6.12 (2H, t), 4.75 (1H, s), 3.60 (6H, s), 1.69 (6H, s).

Step 3: Methyl 6-hydroxy-5,5-dimethyl-8-oxo-5,8-dihydroindolizin-7-carboxylate (4c)

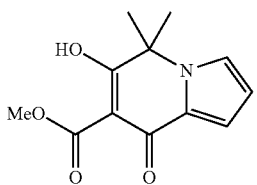

4c

Compound 4b (830 mg) was dissolved in 8 ml of dichloromethane, and 4 ml of methanesulfonic acid was slowly added dropwise at RT. The reaction was stirred for 1 hour. The resulting mixture was extracted with dichloromethane. The dichloromethane layer was separated, then washed twice with diluted aqueous sodium chloride. The separated dichloromethane phase was dried over anhydrous sodium sulfate; filtered to remove the desiccant and then evaporated to dryness on a rotary evaporator. The resulting residue was purified by column chromatography to yield 550 mg of compound 4c. $^1$H NMR (500 MHz, dmso-d6) δ (ppm): 13.97 (1H, br s), 7.73-7.72 (1H, m), 6.70-6.99 (1H, m), 6.47-6.46 (1H, m), 3.81 (3H, s), 1.58 (6H, s).

Step 4: (6-Hydroxy-5,5-dimethyl-8-oxo-5,8-dihydroindolizin-7-carbonyl) glycine (4)

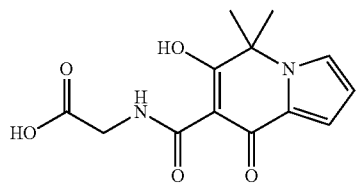

4

Compound 4c (150 mg), glycine (270 mg) and 0.5 M sodium methoxide solution in methanol (6 mL) were combined and evaporated to dryness. Then, n-propyl alcohol (5 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, washed with water, and then dried to give 84 mg of compound 4. $^1$H NMR (500 MHz, dmso-d6) δ (ppm): 18.19 (1H, s), 12.99 (1H, s), 9.99 (1H, s), 7.76 (1H, s), 6.97 (1H, s), 6.48 (1H, s), 4.10 (1H, d), 1.65 (6H, s). LCMS ESI(+): 279 (M+1)$^+$.

Example 5: (6-Hydroxy-5,5-dimethyl-8-oxo-5,8-dihydroindolizin-7-carbonyl)-L-alanine (5)

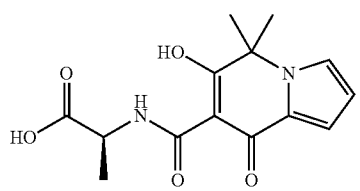

5

Step 1: (6-Hydroxy-5,5-dimethyl-8-oxo-5,8-dihydroindolizin-7-carbonyl)-L-alanine (5)

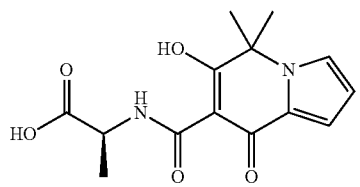

5

Compound 4c (150 mg), L-alanine (320 mg) and 0.5 M sodium methoxide solution in methanol (6 mL) were combined and evaporated to dryness. Then, n-propyl alcohol (5 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, washed with water, and then dried to give 141 mg of compound 5. $^1$H NMR (500 MHz, dmso-d6) δ (ppm): 18.10 (1H, s), 13.19 (1H, s), 10.13

(1H, d), 7.76 (1H, s), 6.97 (1H, s), 6.48 (1H, s), 4.51-4.46 (1H, m), 1.64 (6H, s), 1.45 (3H, d). LCMS ESI(+): 293 (M+1)⁺.

Example 6: (6'-Hydroxy-8'-oxo-8'H-spiro[cyclobutane-1,5'-indolizine]-7'-carbonyl)glycine (6)

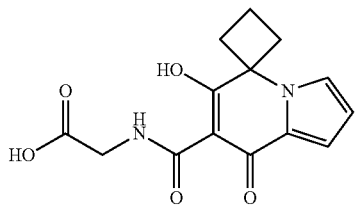

Step 1: 1-(1H-pyrrol-1-yl)cyclobutane-1-carboxylic acid (6a)

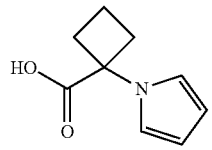

6a 0.8 ml of concentrated hydrochloric acid was added to a mixture of 2,5-dimethoxytetrahydrofuran (2.09 g) and water; the resulting mixture was stirred at RT for 1 hour; and then sodium acetate solid (5.38 g) and 1-amino-cyclobutane-1-carboxylic acid (2 g) were successively added to the reaction mixture. The reaction mixture was stirred at RT overnight; then diluted with water, neutralized with 1 M hydrochloric acid to pH 4; and then extracted with ethyl acetate. The ethyl acetate layer was separated, and then washed twice with dilute aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 2 g of compound 6a. ¹H NMR (500 MHz, dmso-d6) δ (ppm): 12.81 (1H, s), 6.75 (2H, t), 6.03 (2H, t), 2.76-2.71 (2H, m), 2.58-2.51 (2H, m), 2.01-1.93 (2H, m).

Step 2: 2-(1-(1H-pyrrol-1-yl)cyclobutane-1-acyl) malonate dimethyl ester (6b)

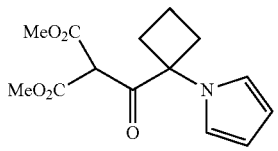

6b

Compound 6a (2 g) and CDI (2.36 g) were mixed in tetrahydrofuran (35 ml) and the resulting mixture was stirred at RT for 1 hour. Then dimethyl malonate sodium salt (2.8 g) was added and was stirred for one hour. The resulting mixture was diluted with water and acidified carefully with 1 M diluted hydrochloric acid aqueous solution to pH 4; and then extracted with ethyl acetate. The ethyl acetate layer was separated, and then washed twice with diluted aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 1.25 g of compound 6b (with a small amount of dimethyl malonate). ¹H NMR (500 MHz, dmso-d6) δ (ppm): 6.80 (2H, t), 6.15 (2H, t), 4.44 (1H, s), 3.59 (6H, s), 2.78-2.72 (2H, m), 2.61-2.55 (2H, m), 1.96-1.90 (2H, m).

Step 3: Ethyl 6'-Hydroxy-8'-oxo-8'H-spiro[cyclobutane-1,5'-indolizine]-7'-carboxylate (6c)

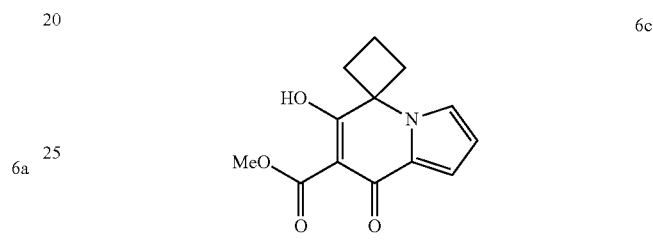

6c

Compound 6b (650 mg) was dissolved in 6 ml of dichloromethane, and 3 ml of methanesulfonic acid was slowly added dropwise at RT. The reaction was stirred for 1 hour. The resulting mixture was extracted with dichloromethane. The dichloromethane layer was separated, then washed twice with diluted aqueous sodium chloride. The separated dichloromethane phase was dried over anhydrous sodium sulfate; filtered to remove the desiccant and then evaporated to dryness on a rotary evaporator. The resulting residue was purified by column chromatograph to yield 300 mg of compound 6c. ¹H NMR (500 MHz, dmso-d6) δ (ppm): 13.93 (1H, s), 7.96-7.95 (1H, m), 6.99-6.98 (1H, m), 6.52-6.50 (1H, m), 3.82 (3H, s), 2.77-2.72 (2H, m), 2.48-2.43 (2H, m), 2.12-2.04 (2H, m).

Step 4: (6'-Hydroxy-8'-oxo-8'H-spiro[cyclobutane-1, 5'-indolizine]-7'-carbonyl)glycine (6)

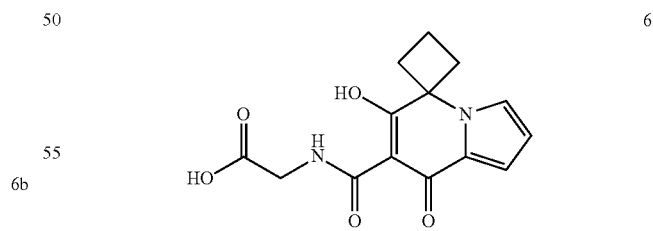

6

Compound 6c (150 mg), glycine (270 mg) and 0.5 M sodium methoxide solution in methanol (6 mL) were combined and evaporated to dryness. Then, n-propyl alcohol (5 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, washed with water, and then dried to give 142 mg of compound 6. $^1$H NMR (500 MHz, dmso-d6) δ (ppm): 18.09 (1H, s), 12.95 (1H, s), 10.07 (1H, s), 7.99 (1H, s), 6.96 (1H, s), 6.52 (1H, s), 4.11 (2H, d), 2.82-2.78 (2H, m), 2.59-2.55 (2H, m), 2.15-2.09 (2H, m). LCMS ESI(+): 291 (M+1)$^+$.

Example 7: (6'-Hydroxy-8'-oxo-8'H-spiro[cyclobutane-1,5'-indolizine]-7'-carbonyl)-L-alanine (7)

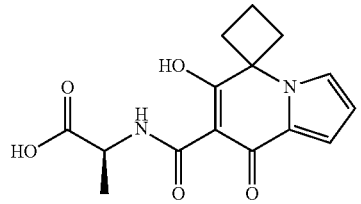

Step 1: (6'-Hydroxy-8'-oxo-8'H-spiro[cyclobutane-1,5'-indolizine]-7'-carbonyl)-L-alanine (7)

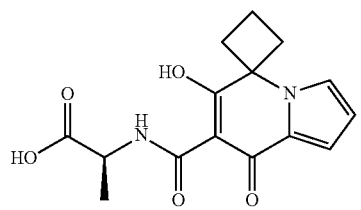

Compound 6c (150 mg), L-alanine (320 mg) and 0.5 M sodium methoxide solution in methanol (6 mL) were combined and evaporated to dryness. Then, n-propyl alcohol (54 ml) was added with refluxing until the reaction was complete. After cooling, the reaction solution was diluted with water, and then carefully acidified to a pH of about 4 with a 1 M diluted aqueous solution of hydrochloric acid. Solid was precipitated, collected by filtration, washed with water, and then dried to give 140 mg of compound 7. $^1$H NMR (500 MHz, dmso-d6) δ (ppm): 18.05 (1H, s), 13.05 (1H, s), 10.21 (1H, d), 7.98 (1H, s), 6.95 (1H, s), 6.52 (1H, s), 4.51-4.46 (1H, m), 2.84 (2H, br s), 2.60-2.54 (2H, m), 2.17-2.10 (2H, m), 1.45 (2H, d). LCMS ESI(+): 305 (M+1)$^+$.

Example 8: (6'-Hydroxy-8'-oxo-8'H-spiro[cyclopentane-1,5'-indolizine]-7'-carbonyl)glycine (a)

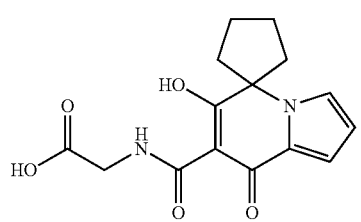

Step 1: 1-(1H-pyrrol-1-yl)cyclopentane-1-carboxylic acid (8a)

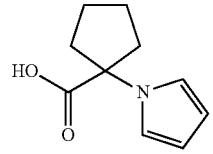

The synthetic route of the first step of Example 6 was repeated, wherein the starting material 1-aminocyclobutane-1-carboxylic acid was replaced with 1-aminocyclopentane-1-carboxylic acid to obtain the compound 8a. $^1$H NMR (500 MHz, dmso-d6) δ (ppm): 6.82 (2H, t, J=3 Hz), 5.99 (2H, t, J=3 Hz), 2.45-2.37 (2H, m), 2.25-2.16 (2H, m), 1.79-1.60 (4H, m).

Step 2: 2-(1-(1H-pyrrol-1-yl)cyclopentan-1-acyl) malonate diethyl ester (8b)

Compound 8a (1.17 g), 1H-benzo[d][1,2,3]triazole-1-ol (1.20 g) and DCC (1.61 g) were mixed in tetrahydrofuran (20 ml) and the resulting mixture was stirred at RT for 1 hour. The solid was removed by filtration, and washed with a small amount of anhydrous tetrahydrofuran. The filtrate and washings were combined.

In a separate reaction flask, diethyl malonate (1.57 g) was dissolved in anhydrous tetrahydrofuran (30 ml), then cooled at an ice water bath, and to this a mixture of mineral oil with purity of 60% and sodium hydride (392 mg) was carefully added under a nitrogen stream and then the resulting reaction mixture was stirred for one hour. The above combined filtrate and washings were then added to the second reaction flask. The reaction was stirred for 1 hour. The resulting mixture was diluted with water, acidified carefully with 1 M dilute aqueous hydrochloric acid to pH 4; and then extracted with ethyl acetate. The ethyl acetate layer was separated, then washed twice with diluted aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield 2.25 g of compound 8b (with a small amount of diethyl malonate). $^1$H NMR (500 MHz, dmso-d6) δ (ppm): 6.845 (2H, t, J=2.5 Hz), 6.12 (2H, t, J=2.5 Hz), 4.51 (1H, s), 4.07-4.00 (4H, m), 2.44-2.34 (2H, m), 2.32-2.25 (2H, m), 1.78-1.63 (4H, m).

Step 3: Ethyl 6'-Hydroxy-8'-oxo-8'H-spiro[cyclopentane-1,5'-indolizine]-7'-carboxylate (8c)

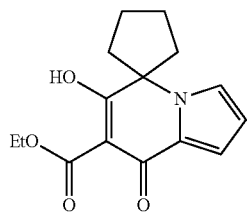

8c

Compound 8b (1.7 g) was dissolved in 6 ml of dichloromethane, and 3.5 ml of methanesulfonic acid was slowly added dropwise at RT. The reaction was stirred for 1 hour. The resulting mixture was extracted with dichloromethane. The dichloromethane layer was separated, then washed twice with diluted aqueous sodium chloride. The separated dichloromethane phase was dried over anhydrous sodium sulfate; filtered to remove the desiccant and then evaporated to dryness on a rotary evaporator. The resulting residue was purified by column chromatograph to yield 373 mg of compound 8c. $^1$H NMR (500 MHz, dmso-d6) δ (ppm): 14.06 (1H, s), 7.57-7.53 (1H, m), 7.03-6.96 (1H, m), 6.47-6.42 (1H, m), 4.29 (2H, q, J=9 Hz), 2.43-2.31 (2H, m), 2.02-1.90 (2H, m), 1.90-1.75 (4H, m), 1.29 (3H, t, J=9 Hz).

Step 4: (6'-Hydroxy-8'-oxo-8'H-spiro[cyclopentane-1,5'-indolizine]-7'-carbonyl) glycine (8)

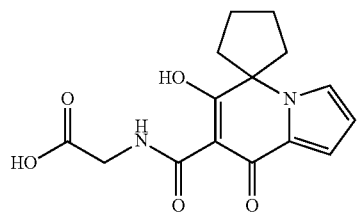

8

The synthetic route of the fourth step of Example 6 was repeated, wherein the starting material 6c was replaced with 8c to afford compound 8. $^1$H NMR (500 MHz, dmso-d6) δ (ppm): 18.12 (1H, s), 12.99 (1H, s), 9.95 (1H, s), 7.59 (1H, s), 6.98 (1H, d, J=6 Hz), 6.47 (1H, s), 4.07 (2H, d, J=6 Hz), 2.45-2.37 (1H, m), 2.05-1.96 (2H, m), 1.94-1.82 (4H, m). LCMS ESI(+): 305 (M+1)$^+$.

Example 9: (6'-Hydroxy-8'-oxo-8'H-spiro[cyclopentane-1,5'-indolizine]-7'-carbonyl)glycine methyl ester (9)

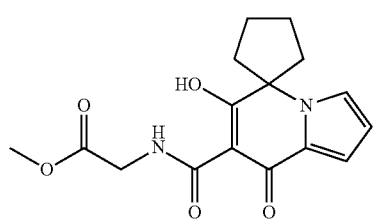

9

Step 1: (6'-Hydroxy-8'-oxo-8'H-spiro[cyclopentane-1,5'-indolizine]-7'-carbonyl) glycine methyl ester (9)

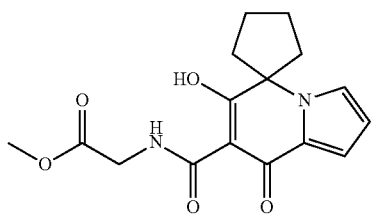

9

Compound 8 (150 mg) was dissolved in 4 mL of methanol, and then to this thionyl chloride (233 mg) was slowly added dropwise. After the addition, the reaction was refluxed for 3 hours. After cooling, the resulting mixture was diluted with water and then extracted with dichloromethane. The organic phase was washed successively with water and diluted aqueous sodium chloride. The organic phase was dried over anhydrous sodium sulfate; filtered and concentrated. The resulting residue was purified by column chromatograph to yield 140 mg of compound 9. $^1$H NMR (500 MHz, dmso-d6) δ (ppm): 17.92 (1H, s), 9.95 (1H, br s), 7.59 (1H, s), 7.00 (1H, s), 6.48 (1H, s), 4.19 (1H, d), 3.70 (3H, s), 2.45-2.39 (2H, m), 2.04-2.00 (2H, m), 1.94-1.85 (4H, m). LCMS ESI(+): 319 (M+1)$^+$.

Example 10 (6'-Hydroxy-8'-oxo-8'H-spiro[cyclopentane-1,5'-indolizine]-7'-carbonyl)glycine ethyl ester (10)

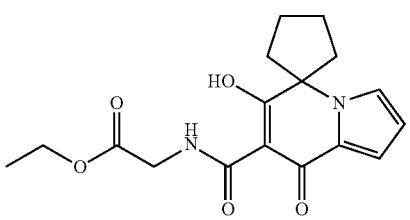

10

Step 1: (6'-Hydroxy-8'-oxo-8'H-spiro[cyclopentane-1,5'-indolizine]-7'-carbonyl)glycine ethyl ester (10)

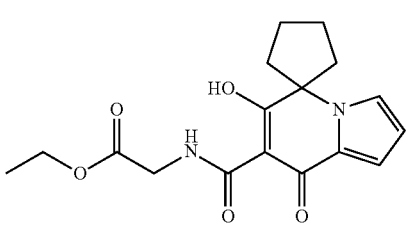

10

The synthetic route of the first step of Example 9, the solvent methanol was replaced with ethanol to afford Compound 10. $^1$H NMR (500 MHz, dmso-d6) δ (ppm): 17.95 (1H, s), 9.96 (1H, br s), 7.59 (1H, s), 7.00 (1H, s), 6.48 (1H, s), 4.18 (1H, d), 2.46-2.39 (2H, m), 2.06-2.02 (2H, m), 1.95-1.90 (4H, m), 1.25-1.21 (3H, m). LCMS ESI(+): 333 (M+1)$^+$.

Example 11: (6'-Hydroxy-8'-oxo-8'H-spiro[cyclopentane-1,5'-indolizine]-7'-carbonyl)-L-alanine (11)

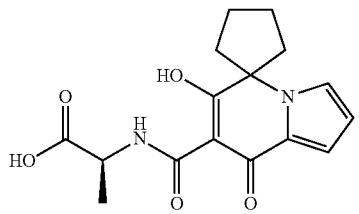

11

Step 1: (6'-Hydroxy-8'-oxo-8'H-spiro[cyclopentane-1,5'-indolizine]-7'-carbonyl)-L-alanine (H)

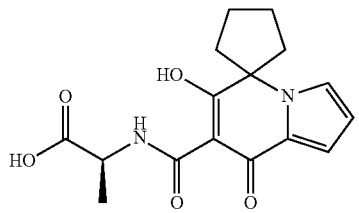

11

The synthetic route of the first step of Example 2 was repeated, wherein the starting material 1c was replaced with 8c to afford Compound 11. $^1$H NMR (500 MHz, dmso-d6) δ (ppm): 18.02 (1H, s), 13.12 (1H, s), 10.09 (1H, d), 7.59 (1H, s), 6.99 (1H, s), 6.48 (1H, s), 4.51-4.46 (1H, m), 2.42-2.37 (2H, m), 2.02 (2H, br s), 1.89 (4H, br s), 1.45 (3H, d). LCMS ESI(+): 319 (M+1)$^+$.

Example 12: (6'-Hydroxy-8'-oxo-8'H-spiro[cyclopentane-1,5'-indolizine]-7'-carbonyl)-D-alanine (12)

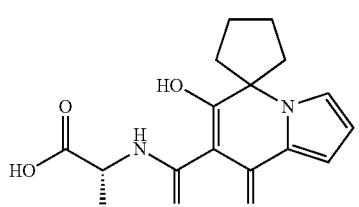

12

Step 1: (6'-Hydroxy-8'-oxo-8'H-spiro[cyclopentane-1,5'-indolizine]-7'-carbonyl)-D-alanine (12)

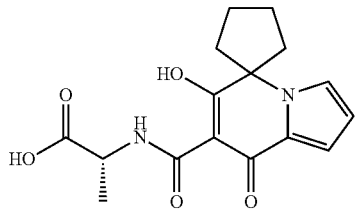

12

The synthetic route of the first step of Example 3 was repeated, wherein the starting material 1c was replaced with 8c to afford Compound 12. $^1$H NMR (500 MHz, dmso-d6) δ (ppm): 18.03 (1H, s), 13.19 (1H, s), 10.09 (1H, d), 7.59 (1H, s), 6.99 (1H, s), 6.48 (1H, s), 4.51-4.46 (1H, m), 2.43-2.38 (2H, m), 2.03-2.01 (2H, m), 1.89 (4H, br s), 1.45 (3H, d). LCMS ESI(+): 319 (M+1)$^+$.

Example 13: (6'-Hydroxy-8'-oxo-8'H-spiro[cyclohexane-1,5'-indolizine]-7'-carbonyl)glycine (13)

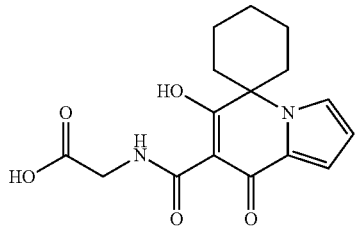

13

Step 1: 1-(1H-pyrrol-1-yl)cyclohexane-1-carboxylic acid (13a)

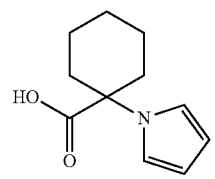

13a

The synthetic route of the first step of Example 6 was repeated, wherein the starting material 1-aminocyclobutane-1-carboxylic acid was replaced with 1-aminocyclohexane-1-carboxylic acid to afford the compound 13a. $^1$H NMR (400 MHz, CDCl$_3$) δ (ppm) 6.87 (t, 2H), 6.22 (t, 2H), 2.40-2.33 (m, 2H), 2.22-2.16 (m, 2H), 1.64-1.58 (m, 4H), 1.54-1.42 (m, 2H).

Step 2: 2-(1-(1H-pyrrol-1-yl)cyclohexane-1-acyl)malonate diethyl ester (13b)

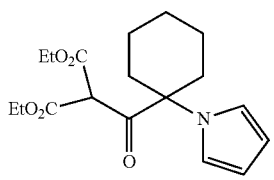

The synthetic route of the second step of Example 8 was repeated, wherein the starting material 8a was replaced with 13a to afford the compound 13b. ¹H NMR (500 MHz, dmso-d6) δ (ppm): 6.92 (t, 2H), 6.15 (t, 2H), 4.49 (s, 1H), 4.06-3.99 (m, 4H), 2.34 (d, 2H), 1.97 (t, 2H), 1.62 (t, 2H), 1.48 (t, 2H), 1.31 (t, 2H), 1.13 (t, 6H).

Step 3: 6'-Hydroxy-8'-oxo-8'H-spiro[cyclohexane-1,5'-indolizine]-7'-carboxylic acid ethyl ester (1)

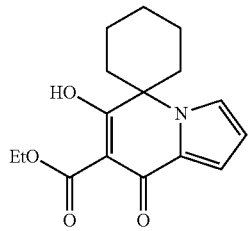

The synthetic route of the third step of Example 8 was repeated, wherein the starting material 8b was replaced with 13b to afford the compound 13c. ¹H NMR (500 MHz, dmso-d6) δ (ppm): 13.78 (s, 1H), 7.75 (dd, 1H), 6.99 (dd, 1H), 6.44 (dd, 1H), 4.29 (q, 2H), 2.00-1.96 (m, 2H), 1.86-1.78 (m, 4H), 1.66-1.61 (m, 3H), 1.44-1.40 (m, 1H), 1.29 (t, 3H).

Step 4: (6'-Hydroxy-8'-oxo-8'H-spiro[cyclohexane-1,5'-indolizine]-7'-carbonyl)glycine (13)

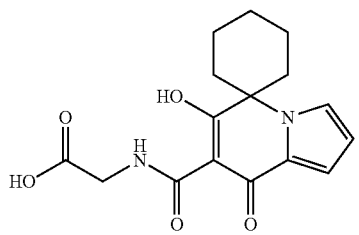

The synthetic route of the fourth step of Example 6 was repeated, wherein the starting material 6c was replaced with 13c to afford the compound 13. ¹H NMR (500 MHz, dmso-d6) δ (ppm): 18.12 (s, 1H), 13.02 (s, 1H), 10.01 (s, 1H), 7.90 (s, 1H), 7.07 (d, 1H), 6.57 (t, 1H), 4.16 (d, 2H), 1.82-1.74 (m, 10H). LCMS ESI(+): 319 (M+1)⁺.

Example 14: (6'-Hydroxy-8'-oxo-8'H-spiro[cyclohexane-1,5'-indolizine]-7'-carbonyl)-L-alanine (14)

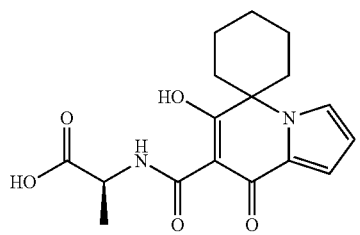

Step 1: (6'-Hydroxy-8'-oxo-8'H-spiro[cyclohexane-1,5'-indolizine]-7'-carbonyl)-L-alanine (14)

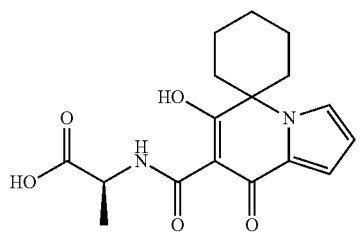

The synthetic route of the first step of Example 2 was repeated, wherein the starting material 1c was replaced with 13c to afford the compound 14. ¹H NMR (500 MHz, dmso-d6) δ (ppm): 18.00 (s, 1H), 13.15 (br, 1H), 10.07 (s, 1H), 7.81 (s, 1H), 6.98 (s, 1H), 6.48 (s, 1H), 4.50~4.44 (m, 1H), 2.04~4.88 (m, 10H), 1.44 (d, 3H). LCMS ESI(+): 333 (M+1)⁺.

Example 15: (3'-Cyclobutyl-6'-hydroxy-8'-oxo-8'H-spiro[cyclopentane-1,5'-indolizine]-7'-carbonyl)glycine (1)

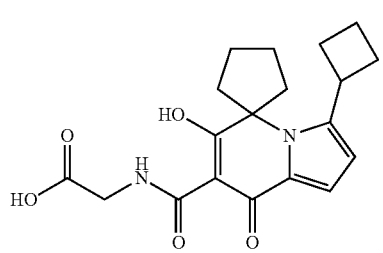

Step 1: 1-(2-cyclobutyl-1H-pyrrol-1-yl)cyclopentane-1-carboxylic acid (15a)

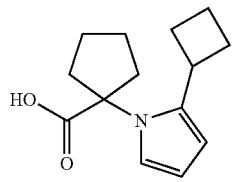

1-cyclobutyl-3-(1,3-dioxan-2-yl)propan-1-one (1 eq.; prepared according to the method described in the patent document WO/2011/042477) and 1-amino-cyclopentane-1-carboxylic acid (1.2 eq.) were suspended in acetic acid (4 vol.) and then stirred under reflux overnight. After cooling, most of acetic acid was evaporated to dryness on a rotary evaporator. The resulting residue was diluted with water, extracted with ethyl acetate. The ethyl acetate layer was separated, then washed twice with diluted aqueous sodium chloride. The separated ethyl acetate phase was dried over anhydrous sodium sulfate; filtered to remove the desiccant and then evaporated to dryness on a rotary evaporator. The resulting residue was purified by column chromatograph to yield compound 15a. LCMS ESI(+): 234 (M+1)$^+$.

Step 2: Dimethyl 2-(1-(2-cyclobutyl-1H-pyrrol-1-yl)cyclopentane-1-carbonyl)malonate (15b)

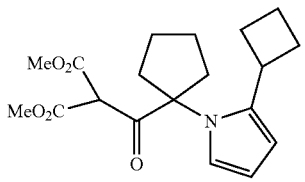

The synthetic route of the second step for compound 8b of Example 8 was repeated, wherein the starting materials 8a and diethyl malonate were respectively replaced with 15a and dimethyl malonate to afford compound 15b. LCMS ESI(+): 348 (M+1)$^+$. $^1$H NMR (500 MHz, DMSO-d6) δ 6.90 (dd, J=3.0, 1.7 Hz, 1H), 6.14 (dd, J=3.6, 1.7 Hz, 1H), 6.06 (t, J=3.3 Hz, 1H), 4.48 (s, 1H), 3.54 (d, J=3.2 Hz, 6H), 2.93-2.82 (m, 1H), 2.17 (dd, J=9.8, 7.2 Hz, 2H), 2.10-1.89 (m, 4H), 1.80-1.69 (m, 4H), 1.59 (s, 2H).

Step 3: 3'-Cyclobutyl-6'-hydroxy-8'-oxo-8'H-spiro[cyclopentane-1,5'-indolizine]-7'-carboxylic acid methyl ester (15c)

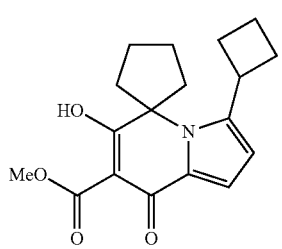

The synthetic route of the third step of Example 8 was repeated, wherein the starting material 8b was replaced with 15b to afford compound 15c. LCMS ESI(+): 316 (M+1)$^+$.

Step 4: (3'-Cyclobutyl-6'-hydroxy-8'-oxo-8'H-spiro[cyclopentane-1,5'-indolizine]-7'-carbonyl)glycine (11)

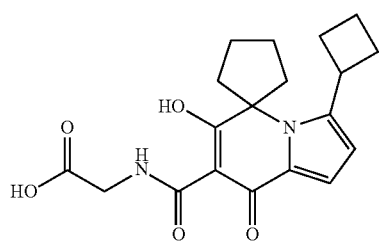

The synthetic route of the fourth step of Example 1 was repeated, wherein the starting material 1c was replaced with 15c to afford compound 15. $^1$H NMR (500 MHz, DMSO-d6) δ 17.79 (s, 1H), 12.96 (s, 1H), 9.90 (t, J=5.6 Hz, 1H), 6.99 (d, J=4.2 Hz, 1H), 6.65 (d, J=4.3 Hz, 1H), 4.05 (d, J=5.5 Hz, 2H), 3.63 (q, J=8.5 Hz, 2H), 2.42-2.30 (m, 6H), 2.23-2.08 (m, 6H), 1.85 (dd, J=10.8, 8.2 Hz, 2H).

Example 16: (3'-Cyclopropyl-6'-hydroxy-8'-oxo-8'H-spiro[cyclopentane-1,5'-indolizine]-7'-carbonyl)glycine (11)

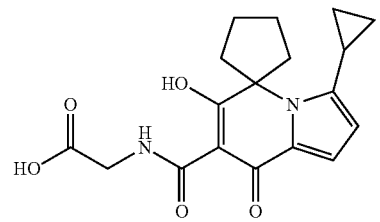

Step 1: 1-(2-cyclopropyl-1H-pyrrol-1-yl)cyclopentane-1-carboxylic acid (16a)

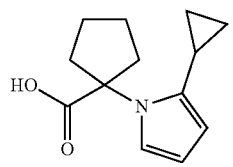

The synthetic route of the first step for compound 15a of Example 15 was repeated, wherein the starting material 1-cyclobutyl-3-(1,3-dioxan-2-yl)propan-1-one was replaced with 1-cyclopropyl-3-(1,3-dioxan-2-yl)propan-1-one which was prepared according to the method described in the patent document WO/2011/042477 to afford compound 16a. LCMS ESI(+): 220 (M+1)$^+$.

Step 2: Dimethyl 2-(1-(2-cyclopropyl-1H-pyrrol-1-yl)cyclopentane-1-carbonyl)malonate

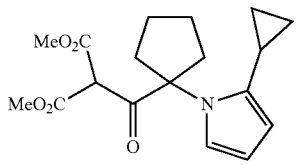

16b

The synthetic route of the second step for compound 15b of Example 15 was repeated, wherein the starting material 15a was replaced with 16a to afford compound 16b. LCMS ESI(+): 334 (M+1)+.

Step 3: Methyl 3'-Cyclopropyl-6'-hydroxy-8'-oxo-8'H-spiro[cyclopentane-1,5'-indolizine]-7'-carboxylate (16c)

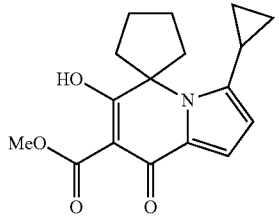

16c

The synthetic route of the third step for compound 15c of Example 15 was repeated, wherein the starting material 16b was used to afford compound 16c. LCMS ESI(+): 302 (M+1)+.

Step 4: (3'-Cyclopropyl-6'-hydroxy-8'-oxo-8'H-spiro[cyclopentane-1,5'-indolizine]-7'-carbonyl)glycine (h)

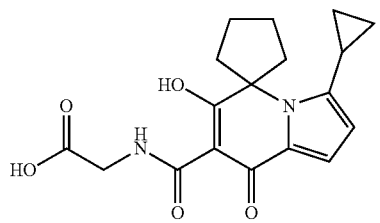

16

The synthetic route of the fourth step for compound 15 of Example 15 was repeated, wherein the starting material 16c was used to afford compound 16. LCMS ESI(+): 345 (M+1)+.

Example 17: (6'-Hydroxy-3'-methyl-8'-oxo-8'H-spiro[cyclopentane-1,5'-indolizine]-7'-carbonyl)glycine (17)

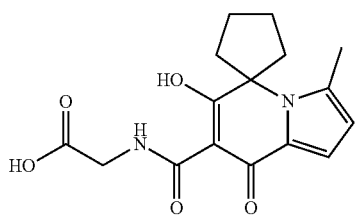

17

Step 1: 1-(2-methyl-1H-pyrrol-1-yl)cyclopentane-1-carboxylic acid (17a)

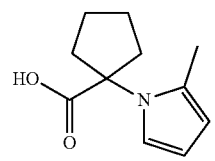

17a

The synthetic route of the first step for compound 15a of Example 15 was repeated, wherein the starting material 1-cyclobutyl-3-(1,3-dioxan-2-yl)propan-1-one was replaced with 4-(1,3-dioxan-2-yl)butan-2-one which was prepared according to the method described in the patent document WO/2011/042477 to afford compound 17a. LCMS ESI(+): 194 (M+1)+.

Step 2: Dimethyl 2-(1-(2-methyl-1H-pyrrol-1-yl)cyclopentane-1-carbonyl)malonate (17b)

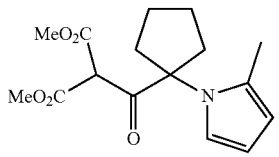

17b

The synthetic route of the second step for compound 15b of Example 15 was repeated, wherein the starting material 15a was replaced with 17a to afford compound 17b. LCMS ESI(+): 308 (M+1)+.

Step 3: Methyl 6'-Hydroxy-3'-methyl-8'-oxo-8'H-spiro[cyclopentane-1,5'-indolizine]-7'-carboxylate (1')

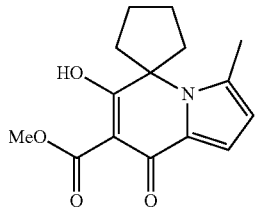
17c

The synthetic route of the third step for compound 15c of Example 15 was repeated, wherein the starting material 17b was used to afford compound 17c. LCMS ESI(+): 276 (M+1)$^+$. $^1$H NMR (500 MHz, dmso-d6) δ (ppm): 13.90 (1H, s), 6.94 (1H, d, J=3.5 Hz), 6.29 (1H, d, J=4.0 Hz), 3.80 (3H, s), 2.48 (3H, s), 2.25-2.32 (2H, m), 2.05-2.11 (3H, m), 1.92-1.98 (2H, m), 1.68-1.75 (1H, m).

Step 4: (3'-Methyl-6'-hydroxy-8'-oxo-8'H-spiro[cyclopentane-1,5'-indolizine]-7'-carbonyl)glycine (17)

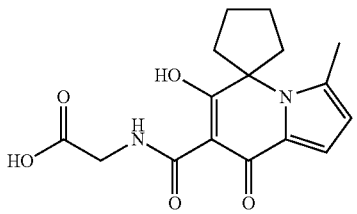
17

The synthetic route of the fourth step for compound 15 of Example 15 was repeated, wherein the starting material 17c was used to afford compound 17. LCMS ESI(+): 319 (M+1)$^+$. $^1$H NMR (500 MHz, dmso-d6) δ (ppm): 17.78 (1H, s) 12.92 (1H, s), 9.92 (1H, t, J=5.5 Hz), 6.93 (1H, d, J=4.0 Hz), 6.31 (1H, d, J=4.0 Hz), 4.06 (2H, d, J=6.0 Hz), 2.49 (3H, s), 2.28-2.39 (4H, m), 2.13-2.19 (2H, m), 2.01-2.08 (2H, m).

Example 18: (3'-(tert-butyl)-6'-hydroxy-8'-oxo-8'H-spiro[cyclopentane-1,5'-indolizine]-7'-carbonyl)glycine (18)

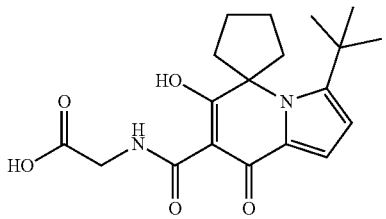
18

Step 1: 1-(2-(tert-butyl)-1H-pyrrol-1-yl)cyclopentane-1-carboxylic acid (18a)

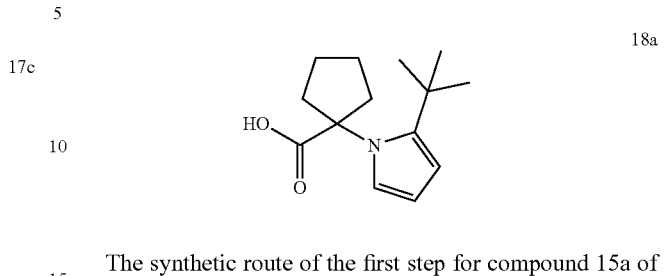
18a

The synthetic route of the first step for compound 15a of Example 15 was repeated, wherein the starting material 1-cyclobutyl-3-(1,3-dioxan-2-yl)propan-1-one was replaced with 1-(1,3-dioxan-2-yl)-4,4-dimethylpentan-3-one which was prepared according to the method described in the patent document WO/2011/042477 to afford compound 18a. LCMS ESI(+): 236 (M+1)$^+$.

Step 2: Dimethyl 2-(1-(2-(tert-butyl)-1H-pyrrol-1-yl)cyclopentane-1-carbonyl)malonate

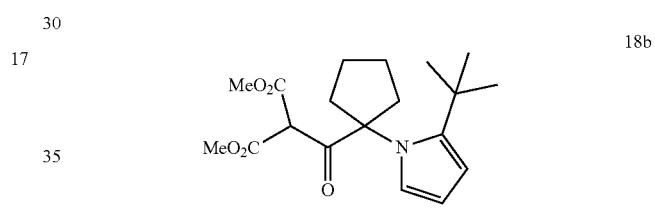
18b

The synthetic route of the second step for compound 15b of Example 15 was repeated, wherein the starting material 15a was replaced with 18a to afford compound 18b. LCMS ESI(+): 350 (M+1)$^+$.

Step 3: Methyl 3'-(tert-Butyl)-6'-hydroxy-8'-oxo-8'H-spiro[cyclopentane-1,5'-indolizine]-7'-carboxylate (18c)

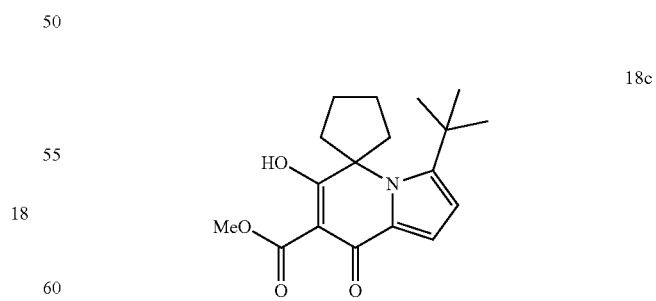
18c

The synthetic route of the third step for compound 15c of Example 15 was repeated, wherein the starting material 18b was used to afford compound 18c. LCMS ESI(+): 318 (M+1)$^+$.

Step 4: (3'-(tert-butyl)-6'-hydroxy-8'-oxo-8'H-spiro[cyclopentane-1,5'-indolizine]-7'-carbonyl)glycine (18)

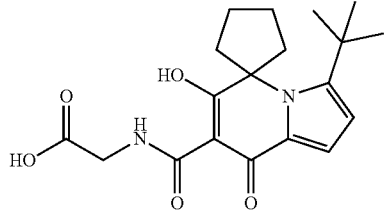

The synthetic route of the fourth step for compound 15 of Example 15 was repeated, wherein the starting material 18c was used to afford compound 18. LCMS ESI(+): 361 (M+1)⁺.

Example 19: (3'-Cyclopentyl-6'-hydroxy-8'-oxo-8'H-spiro[cyclopentane-1,5'-indolizine]-7'-carbonyl)glycine (1)

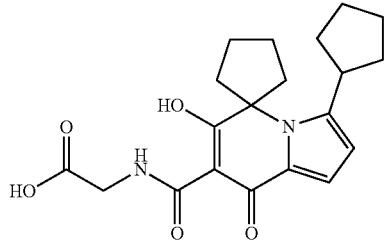

Step 1: 1-(2-cyclopentyl-1H-pyrrol-1-yl)cyclopentane-1-carboxylic acid (19a)

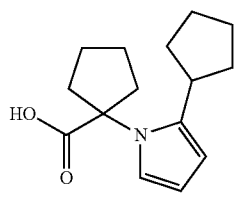

The synthetic route of the first step for compound 15a of Example 15 was repeated, wherein the starting material 1-cyclobutyl-3-(1,3-dioxan-2-yl)propan-1-one was replaced with 1-cyclopentyl-3-(1,3-dioxan-2-yl)-propan-3-one which was prepared according to the method described in the patent document WO/2011/042477 to afford compound 19a. LCMS ESI(+): 248 (M+1)⁺.

Step 2: Dimethyl 2-(1-(2-cyclopentyl-1H-pyrrol-1-yl)cyclopentane-1-carbonyl)malonate (19b)

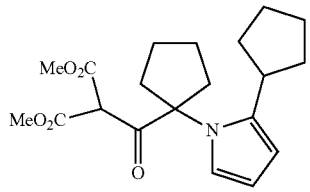

The synthetic route of the second step for compound 15b of Example 15 was repeated, wherein the starting material 15a was replaced with 19a to afford compound 19b. LCMS ESI(+): 362 (M+1)⁺.

Step 3: Methyl 3'-Cyclopentyl-6'-hydroxy-8'-oxo-8'H-spiro[cyclopentane-1,5'-indolizine]-7'-carboxylate (19c)

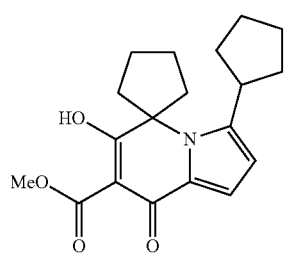

The synthetic route of the third step for compound 15c of Example 15 was repeated, wherein the starting material 19b was used to afford compound 19c. LCMS ESI(+): 330 (M+1)⁺.

Step 4: (3'-Cyclopentyl-6'-hydroxy-8'-oxo-8'H-spiro[cyclopentane-1,5'-indolizine]-7'-carbonyl)glycine (12)

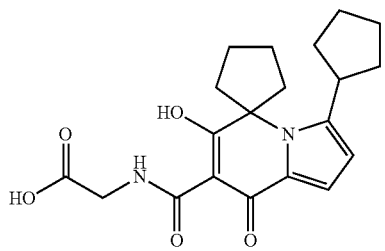

The synthetic route of the fourth step for compound 15 of Example 15 was repeated, wherein the starting material 19c was used to afford compound 19. LCMS ESI(+): 373 (M+1)⁺.

Example 20: (3'-Cyclohexyl-6'-hydroxy-8'-oxo-8'H-spiro[cyclopentane-1,5'-indolizine]-7'-carbonyl)glycine (20)

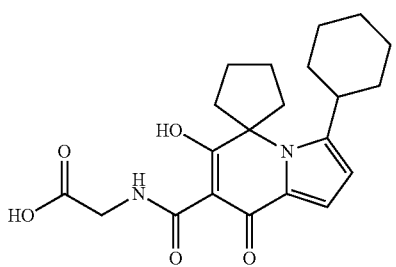

Step 1: 1-(2-cyclohexyl-1H-pyrrol-1-yl)cyclopentane-1-carboxylic acid (20a)

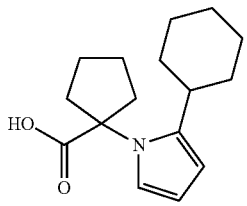

The synthetic route of the first step for compound 15a of Example 15 was repeated, wherein the starting material 1-cyclobutyl-3-(1,3-dioxan-2-yl)propan-1-one was replaced with 1-cyclohexyl-3-(1,3-dioxocyclo-2-yl)propan-1-one, which was prepared according to the method described in the patent document WO/2011/042477 and exhibited the following NMR data: $^1$H NMR (500 MHz, DMSO-d6) δ 4.47 (t, J=5.1 Hz, 1H), 4.0-3.93 (m, 2H), 3.70-3.61 (m, 2H), 2.48 (d, J=7.5 Hz, 2H), 2.39-2.32 (m, 1H), 1.88-1.77 (m, 1H), 1.77-1.71 (m, 2H), 1.71-1.62 (m, 4H), 1.61-1.55 (m, 1H), 1.34-1.26 (m, 2H), 1.26-1.16 (m, 4H), to afford compound 20a. LCMS ESI(+): 262 (M+1)$^+$.

Step 2: Dimethyl 2-(1-(2-cyclohexyl-1H-pyrrol-1-yl)cyclopentane-1-carbonyl)malonate (20b)

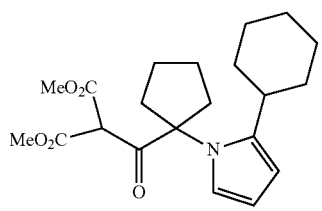

The synthetic route of the second step for compound 15b of Example 15 was repeated, wherein the starting material 15a was replaced with 20a to afford compound 20b. LCMS ESI(+): 376 (M+1)$^+$.

Step 3: Methyl 3'-Cyclohexyl-6'-hydroxy-8'-oxo-8'H-spiro[cyclopentane-1,5'-indolizine]-7'-carboxylate (211c)

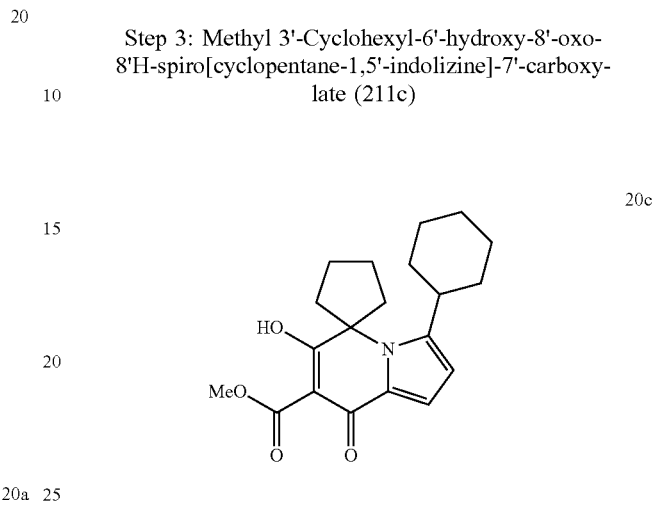

The synthetic route of the third step for compound 15c of Example 15 was repeated, wherein the starting material 20b was used to afford compound 20c. LCMS ESI(+): 344 (M+1)$^+$. $^1$H NMR (500 MHz, DMSO-d6) δ 13.90 (s, 1H), 7.00 (d, J=4.2 Hz, 1H), 6.43 (d, J=4.2 Hz, 1H), 3.80 (s, 3H), 2.72 (m, 1H), 2.44-2.37 (m, 2H), 2.08-1.96 (m, 4H), 1.94-1.87 (m, 2H), 1.84-1.78 (m, 4H), 1.73-1.69 (m, 1H), 1.50-1.43 (m, 2H), 1.34-1.26 (m, 3H).

Step 4: (3'-Cyclohexyl-6'-hydroxy-8'-oxo-8'H-spiro[cyclopentane-1,5'-indolizine]-7'-carbonyl)glycine (20)

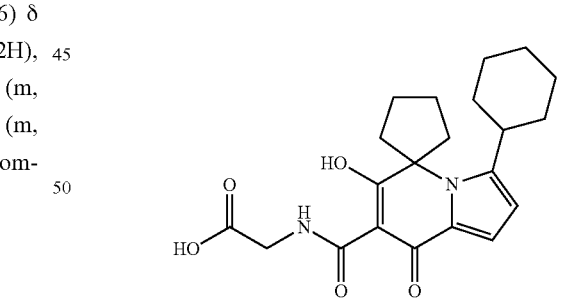

The synthetic route of the fourth step for compound 15 of Example 15 was repeated, wherein the starting material 20c was used to afford compound 20. LCMS ESI(+): 387 (M+1)$^+$. $^1$H NMR (500 MHz, DMSO-d6) δ 12.92 (s, 1H), 9.91 (t, J=6 Hz, 1H), 6.97 (d, J=4.2 Hz, 1H), 6.42 (d, J=4.2 Hz, 1H), 4.06 (d, J=5.6 Hz, 2H), 2.73 (t, J=11.7 Hz, 1H), 2.48-2.38 (m, 2H), 2.17-2.04 (m, 4H), 2.03-1.93 (m, 2H), 1.88-1.78 (m, 4H), 1.74-1.68 (m, 1H), 1.52-1.42 (m, 2H), 1.34-1.26 (m, 3H).

Example 21: (6'-Hydroxy-8'-oxo-8'H-spiro[cyclopentane-1,5'-indolizine]-7'-carbonyl)-L-alanine ethyl ester (21)

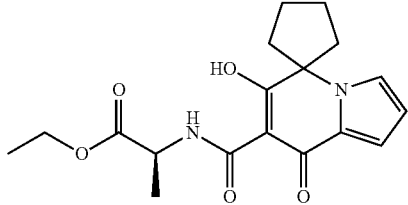

Step 1: (6'-Hydroxy-8'-oxo-8'H-spiro[cyclopentane-1,5'-indolizine]-7'-carbonyl)-L-alanine ethyl ester (21)

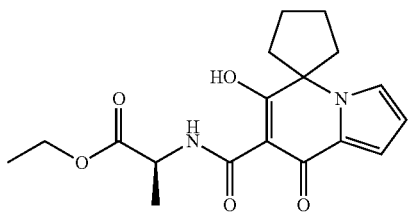

The synthetic route of the first step of Example 9, the solvent methanol was replaced with ethanol and the starting material was replaced with 11 to afford compound 21. LCMS ESI(+): 347 (M+1)+. 1H NMR (500 MHz, dmso-d6) δ (ppm): 17.82 (1H, s), 10.05 (1H, d), 7.61 (1H, s), 7.00 (1H, s), 6.48 (1H, s), 4.58-4.52 (1H, m), 4.18-4.16 (2H, m), 2.42-2.37 (2H, m), 2.03-2.01 (2H, m), 1.89-1.88 (4H, m), 1.45 (3H, d), 1.22 (3H, d).

Example 22: ((((6'-hydroxy-8'-oxo-8'H-spiro[cyclohexane-1,5'-indolizine]-7'-carbonyl)glycyloxy) methyl) pivalate (22)

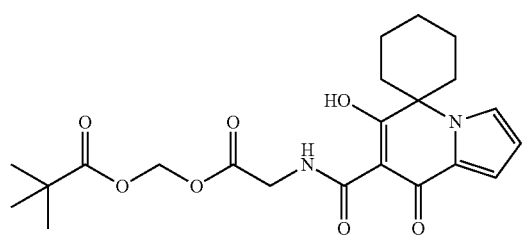

Step 1: ((((6'-hydroxy-8'-oxo-8'H-spiro[cyclohexane-1,5'-indolizine]-7'-carbonyl)glycyloxy) methyl) pivalate (22)

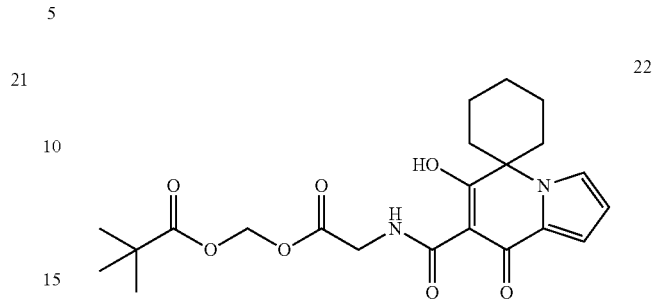

Compound 13 (515 mg) was dissolved in N,N-dimethylformamide (8 ml), and then to this potassium carbonate (560 mg) and chloromethyl pivalate (488 mg) were added successively. The reaction was stirred at RT for 2 days. Then, the resulting mixture was diluted with water and ethyl acetate, and acidified with 2 M hydrochloric acid. The organic phase was separated, washed twice with diluted aqueous sodium chloride solution, and then dried over anhydrous sodium sulfate. After filtration, the filtrate was concentrated and purified by column chromatography to afford compound 22 (70 mg). 1H NMR (500 MHz, dmso-d6) δ (ppm): 17.77 (s, 1H), 9.92 (t, J=6.0 Hz, 1H), 7.82 (t, J=2.0 Hz, 1H), 6.99 (dd, J=4.0 Hz, 1.5 Hz, 1H), 6.49 (t, 1H), 5.76 (s, 2H), 4.20 (d, J=6.0 Hz, 2H), 2.05-1.60 (m, 10H), 1.15 (s, 9H). LCMS ESI(+): 433 (M+1)+.

Example 23: (6'-Hydroxy-8'-oxo-3'-(pyridin-3-yl)-8'H-spiro[cyclopentane-1,5'-indolizine]-7'-carbonyl) glycine (23)

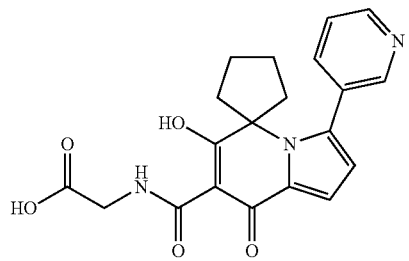

Step 1: 1-(2-(pyridin-3-yl)-1H-pyrrol-1-yl)cyclopentane-1-carboxylic acid

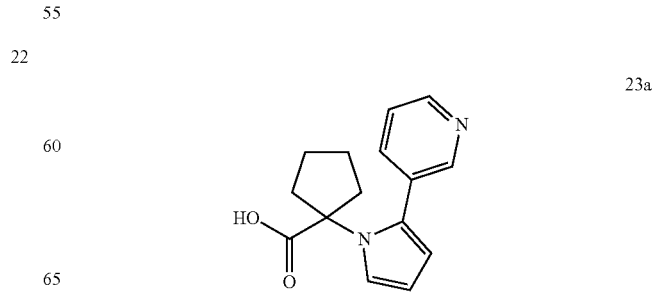

The synthetic route of the first step for compound 15a of Example 15 was repeated, wherein the starting material 1-cyclobutyl-3-(1,3-dioxan-2-yl)propan-1-one was replaced with 3-(1,3-dioxan-2-yl)-1-(pyridin-3-yl)propan-1-one which was prepared according to the method described in the patent document WO/2011/042477 to afford compound 23a. LCMS ESI(+): 257 (M+1)⁺.

Step 2: Dimethyl 2-(1-(2-(pyridin-3-yl)-1H-pyrrol-1-yl)cyclopentane-1-carbonyl)malonate (23b)

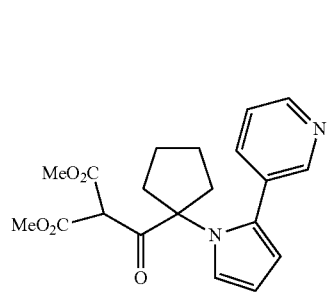

23b

The synthetic route of the second step for compound 15b of Example 15 was repeated, wherein the starting material 15a was replaced with 23a to afford compound 23b. LCMS ESI(+): 371 (M+1)⁺.

Step 3: Methyl 6'-Hydroxy-8'-oxo-3'-(pyridin-3-yl)-8'H-spiro[cyclopentane-1,5'-indolizine]-7'-carboxylate (

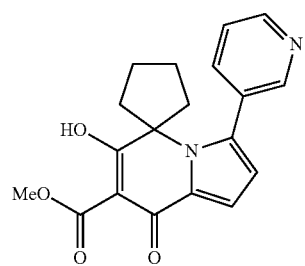

23c

The synthetic route of the third step for compound 15c of Example 15 was repeated, wherein the starting material 23b was used to afford compound 23c. LCMS ESI(+): 339 (M+1)⁺.

Step 4: (6'-Hydroxy-8'-oxo-3 (pyridin-3-yl)-8'H-spiro[cyclopentane-1,5'-indolizine]-7'-carbonyl)glycine (23)

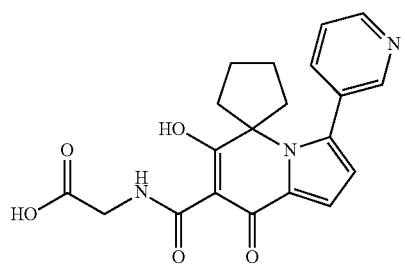

23

The synthetic route of the fourth step for compound 15 of Example 15 was repeated, wherein the starting material 23c was used to afford compound 23.

Example 24: (6'-Hydroxy-8'-oxo-3'-phenyl-8'H-spiro[cyclopentane-1,5'-indolizine]-7'-carbonyl)glycine (24)

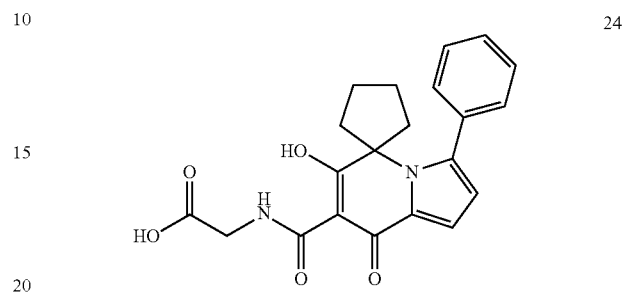

24

Step 1: 1-(2-phenyl-1H-pyrrol-1-yl)cyclopentane-1-carboxylic acid (24a)

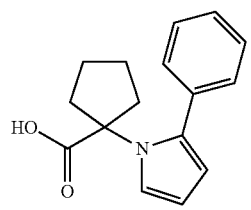

24a 3-(1,3-dioxan-2-yl)-1-phenylpropan-1-one which was prepared according to the method described in the patent document WO/2011/042477 (500 mg) and 1-amino-cyclopentane-1-carboxylic acid (421 mg) were refluxed in 8 mL of acetic acid for 16 hours. After cooling, acetic acid was evaporated to dryness on a rotary evaporator. The resulting residue was diluted with water and ethyl acetate. The organic phase was separated, then washed twice with diluted aqueous sodium chloride solution until water phase was close to neutral. The separated ethyl acetate phase was dried over anhydrous sodium sulfate; filtered, concentrated and then purified by column chromatograph to yield compound 24a. LCMS ESI(+): 256 (M+1)⁺. ¹H NMR (500 MHz, DMSO-d6) δ (ppm): 12.95 (br, s, 1H), 7.35-7.33 (m, 3H), 7.25-7.22 (m, 2H), 7.00-6.99 (m, 1H), 6.04 (m, 1H), 5.95 (m, 1H), 2.14-2.11 (m, 2H), 2.01-1.97 (m, 2H), 1.60-1.57 (m, 4H).

Step 2: Dimethyl 2-(1-(2-phenyl-1H-pyrrol-1-yl)cyclopentane-1-carbonyl)malonate (24b)

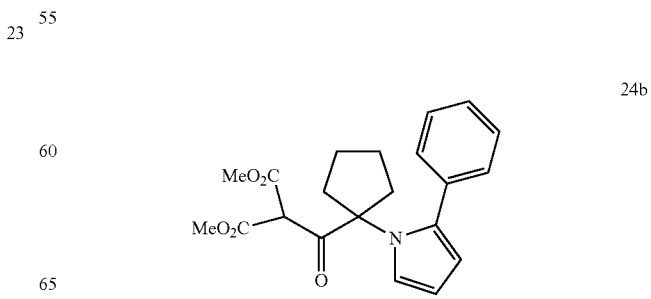

24b

The synthetic route of the second step for compound 15b of Example 15 was repeated, wherein the starting material 15a was replaced with 24a to afford compound 24b. LCMS ESI(+): 370 (M+1)+. 1H NMR (500 MHz, DMSO-d6) δ 7.28-7.22 (m, 3H), 7.20-7.15 (m, 2H), 7.11 (dd, J=3.2, 1.8 Hz, 1H), 6.15 (t, J=3.3 Hz, 1H), 5.93 (dd, J=3.5, 1.7 Hz, 1H), 5.13 (s, 1H), 3.56 (s, 6H), 2.06 (d, J=8.0 Hz, 2H), 1.59 (t, J=12.2 Hz, 2H), 1.33 (s, 2H), 1.16 (s, 2H).

Step 3: Methyl 6'-Hydroxy-8'-oxo-3'-phenyl-8'H-spiro[cyclopentane-1,5'-indolizine]-7'-carboxylate (24c)

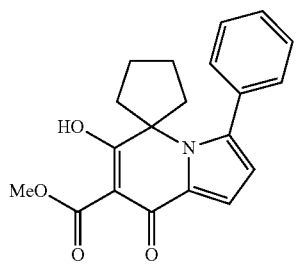

24c

The synthetic route of the third step for compound 15c of Example 15 was repeated, wherein the starting material 15b was replaced with 24b to afford compound 24c. LCMS ESI(+): 338 (M+1)+. 1H NMR (500 MHz, DMSO-d6) δ 13.84 (s, 1H), 7.54-7.43 (m, 5H), 7.09 (d, J=4.0 Hz, 1H), 6.35 (d, J=4.0 Hz, 1H), 3.81 (s, 3H), 2.30-2.21 (m, 2H), 2.10-2.01 (m, 2H), 1.48-1.38 (m, 2H), 1.00-0.89 (m, 2H).

Step 4: (6'-Hydroxy-8'-oxo-3'-phenyl-8'H-spiro[cyclopentane-1,5'-indolizine]-7'-carbonyl)glycine (24)

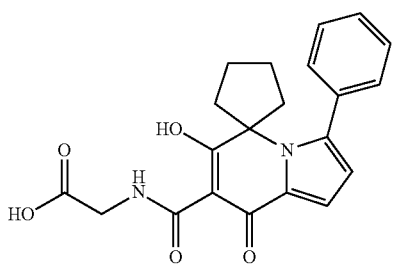

24

The synthetic route of the fourth step for compound 15 of Example 15 was repeated, wherein the starting material 15c was replaced with 24c to afford compound 24. LCMS ESI(+): 381 (M+1)+. 1H NMR (500 MHz, DMSO-d6) δ (ppm) 17.96 (s, 1H), 12.97 (s, 1H), 9.89-9.87 (d, J=5.5 Hz, 1H), 7.53-7.46 (m, 5H), 7.08-7.07 (d, 1H), 6.37-6.36 (d, 1H), 4.08-4.07 (d, J=5.5 Hz, 2H), 2.35-2.20 (m, 2H), 2.18-2.10 (m, 2H), 1.60-1.46 (m, 2H), 0.98-0.85 (m, 2H).

Example 25: (3'-(4-Fluorophenyl)-6'-hydroxy-8'-oxo-8'H-spiro[cyclopentane-1,5'-indolizine]-7'-carbonyl) glycine (25)

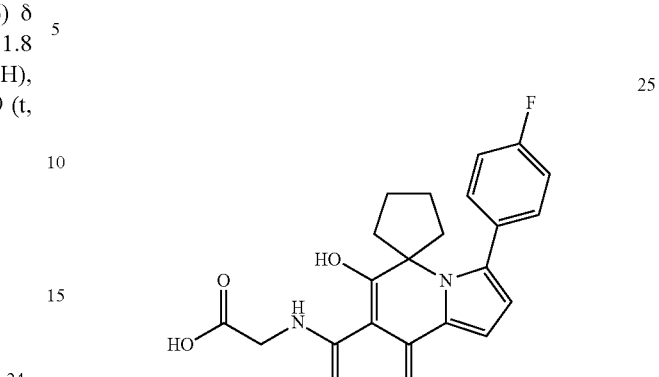

Step 1: 1-(2-(4-Fluorophenyl)-1H-pyrrol-1-yl)cyclopentane-1-carboxylic Acid (25a)

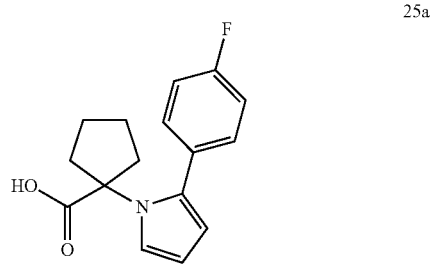 [SMILES: O=C(O)C1(n2cccc2-c2ccc(F)cc2)CCCC1]

The synthetic route of the first step for compound 24a of Example 24 was repeated, wherein the starting material 3-(1,3-dioxan-2-yl)-1-phenylpropan-1-one was replaced by 3-(1,3-dioxan-2-yl)-1-(4-fluorophenyl)propan-1-one which was prepared according to the method described in the patent document WO/2011/042477 to afford compound 25a. LCMS ESI(+): 274 (M+1)+. 1H NMR (500 MHz, dmso-d6) δ (ppm): 12.90 (s, 1H), 7.28-7.24 (m, 2H), 7.20-7.15 (m, 2H), 6.99 (dd, J=1.8, 3.0 Hz, 1H), 6.03 (t, J=3.0 Hz, 1H), 5.95 (dd, J=1.8, 3.0 Hz, 1H), 2.18-2.09 (m, 2H), 1.64-1.55 (m, 4H).

Step 2: Dimethyl 2-(1-(2-(4-fluorophenyl)-1H-pyrrol-1-yl)cyclopentane-1-carbonyl)malonate (25b)

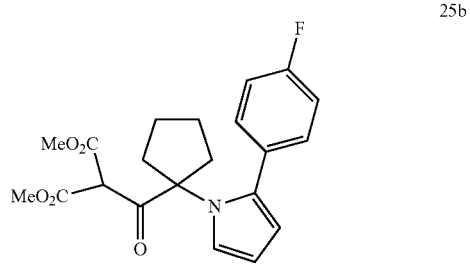 [SMILES: COC(=O)C(C(=O)OC)C(=O)C1(n2cccc2-c2ccc(F)cc2)CCCC1]

The synthetic route of the second step for compound 15b of Example 15 was repeated, wherein the starting material 15a was replaced with 25a to afford compound 25b. LCMS ESI(+): 388 (M+1)$^+$. $^1$H NMR (500 MHz, dmso-d6) δ (ppm): 7.28-7.24 (m, 2H), 7.22-7.13 (m, 3H), 6.16 (t, J=3.3 Hz, 1H), 6.03 (dd, J=1.8, 3.6 Hz, 1H), 5.26 (s, 1H), 3.59 (s, 6H), 2.34-2.26 (m, 2H), 1.90-1.80 (m, 2H), 1.65-1.55 (m, 2H), 1.44-1.36 (m, 2H).

Step 3: Methyl 3'-(4-Fluorophenyl)-6'-hydroxy-8'-oxo-8'H-spiro[cyclopentane-1,5'-indolizine]-7'-carboxylate (25c)

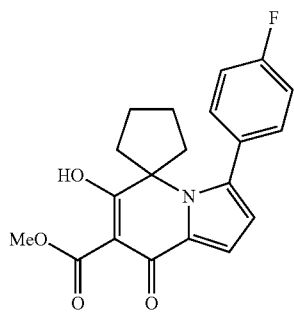

25c

The synthetic route of the third step for compound 15c of Example 15 was repeated, wherein the starting material 15b was replaced with 25b to afford compound 25c. LCMS ESI(+): 356 (M+1)$^+$. $^1$H NMR (500 MHz, dmso-d6) δ (ppm): 7.55-7.50 (m, 2H), 7.28-7.24 (m, 2H), 6.79 (d, J=3.9 Hz, 1H), 6.18 (d, J=3.9 Hz, 1H), 3.67 (s, 3H), 2.28-2.20 (m, 2H), 1.99-1.93 (m, 2H), 1.50-1.43 (m, 2H), 0.93-0.84 (m, 2H).

Step 4: (3'-(4-Fluorophenyl)-6'-hydroxy-8'-oxo-8'H-spiro[cyclopentane-1,5'-indolizine]-7'-carbonyl) glycine (25)

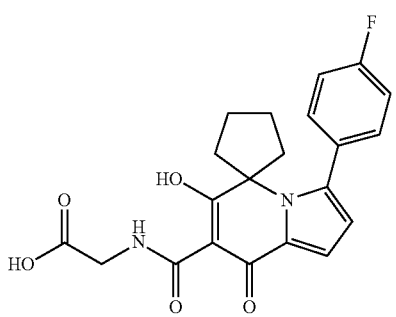

25

The synthetic route of the fourth step for compound 15 of Example 15 was repeated, wherein the starting material 15c was replaced with 25 c to afford compound 25. LCMS ESI(+): 399 (M+1)$^+$. $^1$H NMR (500 MHz, dmso-d6) δ (ppm): 18.00 (s, 1H), 13.00 (s, 1H), 9.89 (s, 1H), 7.63-7.55 (m, 2H), 7.36-7.26 (m, 2H), 7.07 (m, 1H), 6.37 (m, 1H), 4.07 (d, J=5.6 Hz, 2H), 2.35-2.26 (m, 2H), 2.16-2.06 (m, 2H), 1.63-1.50 (m, 2H), 1.00-0.90 (m, 2H).

Example 26: (3'-(4-Chlorophenyl)-6'-hydroxy-8'-oxo-8'H-spiro[cyclopentane-1,5'-indolizine]-7'-carbonyl) glycine (26)

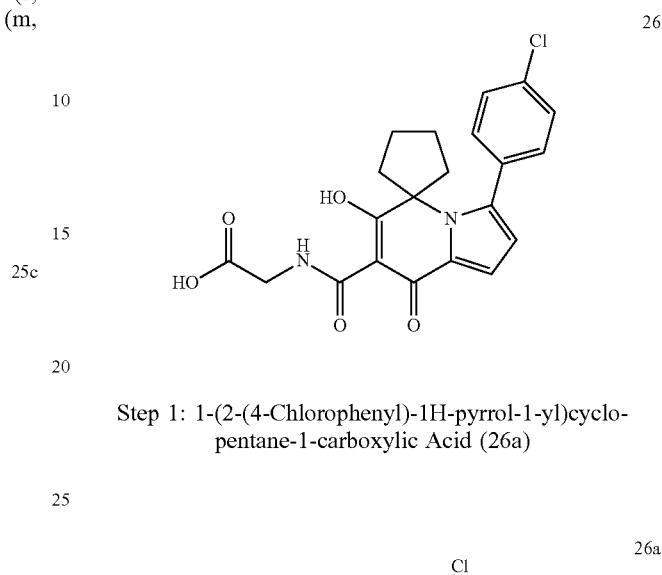

26

Step 1: 1-(2-(4-Chlorophenyl)-1H-pyrrol-1-yl)cyclopentane-1-carboxylic Acid (26a)

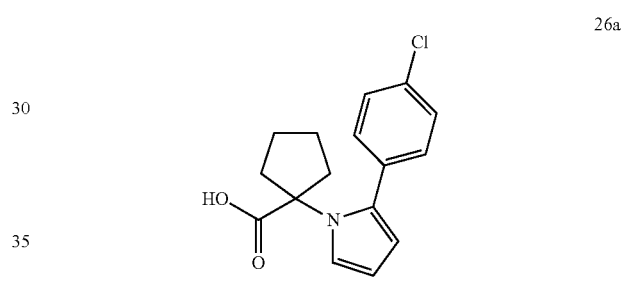

26a

The synthetic route of the first step for compound 24a of Example 24 was repeated, wherein the starting material 3-(1,3-dioxan-2-yl)-1-phenylpropan-1-one was replaced by 3-(1,3-dioxan-2-yl)-1-(4-chlorophenyl)propan-1-one which was prepared according to the method described in the patent document WO/2011/042477 to afford compound 26a. LCMS ESI(+): 290 (M+1)$^+$. $^1$H NMR (500 MHz, dmso-d6) δ (ppm): 12.97 (1H, s), 7.42-7.39 (2H, m), 7.27-7.24 (2H, m), 7.02-7.01 (1H, m), 6.05 (1H, t, J=3.5 Hz), 5.98-5.97 (1H, m), 2.19-2.13 (2H, m), 1.99-1.96 (2H, m), 1.62-1.60 (4H, m).

Step 2: Dimethyl 2-(1-(2-(4-chlorophenyl)-1H-pyrrol-1-yl)cyclopentane-1-carbonyl)malonate (13)

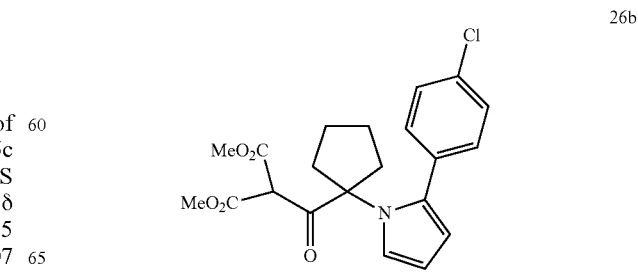

26b

The synthetic route of the second step for compound 15b of Example 15 was repeated, wherein the starting material 15a was replaced with 26a to afford compound 26b. LCMS ESI(+): 404 (M+1)+. 1H NMR (500 MHz, dmso-d6) δ (ppm): 7.42-7.40 (2H, m), 7.25-7.24 (3H, m), 6.17 (1H, t, J=3.0 Hz), 6.06-6.05 (1H, m), 5.39 (1H, s), 3.58 (6H, s), 2.35 (2H, br, s), 1.83 (2H, br s), 1.63-1.60 (2H, m), 1.41-1.39 (2H, m).

Step 3: Methyl 3'-(4-chlorophenyl)-6'-hydroxy-8'-oxo-8'H-spiro[cyclopentane-1,5'-indolizine]-7'-carboxylate (26c)

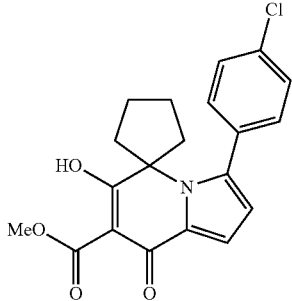

The synthetic route of the third step for compound 15c of Example 15 was repeated, wherein the starting material 15b was replaced with 26b to afford compound 26c. LCMS ESI(+): 372 (M+1)+. 1H NMR (500 MHz, dmso-d6) δ (ppm): 13.85 (1H, s), 7.55 (4H, s), 7.09 (1H, d, J=4.0 Hz), 6.37 (1H, d, J=4.0 Hz), 3.82 (3H, s), 2.30-2.25 (2H, m), 2.03-1.97 (2H, m), 1.50-1.46 (2H, m), 1.01-0.97 (2H, m).

Step 4: (3'-(4-Chlorophenyl)-6'-hydroxy-8'-oxo-8'H-spiro[cyclopentane-1,5'-indolizine]-7'-carbonyl) glycine (26)

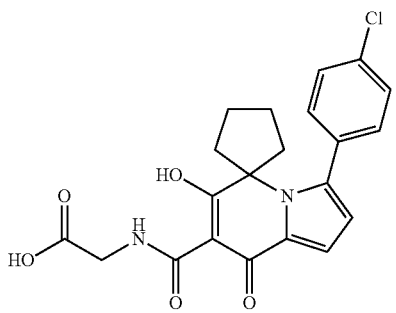

The synthetic route of the fourth step for compound 15 of Example 15 was repeated, wherein the starting material 15c was replaced with 26c to afford compound 26. LCMS ESI(+): 415 (M+1)+. 1H NMR (500 MHz, dmso-d6) δ (ppm): 17.99 (1H, s), 13.03 (1H, br s), 9.87 (1H, s), 7.58-7.54 (4H, m), 7.07 (1H, d, J=2.5 Hz), 6.37 (1H, d, J=3.0 Hz), 4.08 (1H, d, J=5.0 Hz), 2.37-2.30 (2H, m), 2.10-2.09 (2H, m), 1.58 (2H, br, s), 1.02-0.97 (2H, m).

Example 27: (3'-(4-Chlorophenyl)-6'-hydroxy-8'-oxo-8'H-spiro[cyclopentane-1,5'-indolizine]-7'-carbonyl)-L-alanine (Z)

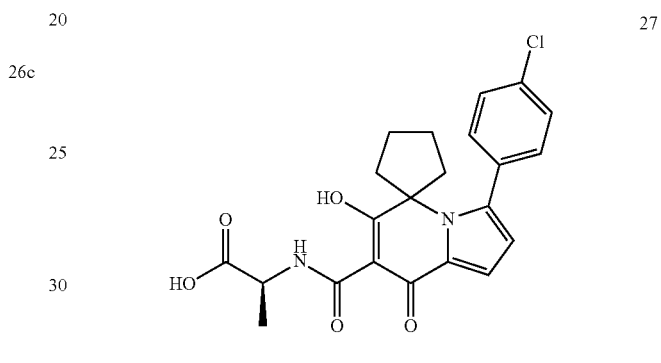

Step 1: (3'-(4-Chlorophenyl)-6'-hydroxy-8'-oxo-8'H-spiro[cyclopentane-1,5'-indolizine]-7'-carbonyl)-L-alanine (27)

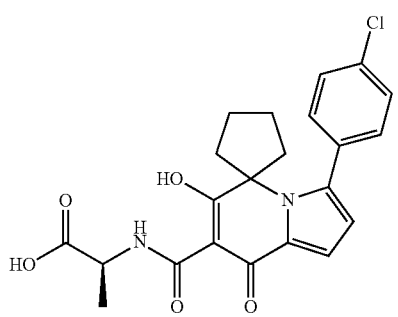

The synthetic route of the fourth step for compound 26 of Example 26 was repeated, wherein the starting material glycine was replaced with L-alanine to afford compound 27. LCMS ESI(+): 429 (M+1)+. 1H NMR (500 MHz, dmso-d6) δ (ppm): 17.88 (1H, s), 13.14 (1H, br s), 9.99 (1H, s), 7.57-7.53 (4H, m), 7.06 (1H, s), 6.36 (1H, d, J=3.0 Hz), 4.51-4.45 (1H, m), 2.36-2.31 (2H, m), 2.12-2.08 (2H, m), 1.58 (2H, br, s), 1.43 (2H, d, J=7.0 Hz), 1.02-0.97 (2H, m).

Example 28: (6'-Hydroxy-3'-(4-methoxyphenyl)-8'-oxo-8'H-spiro[cyclopentane-1,5'-indolizine]-7'-carbonyl glycine (28)

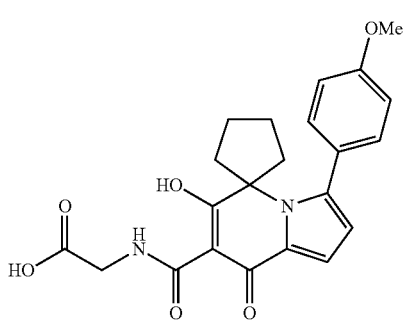

Step 1: 1-(2-(4-methoxyphenyl)-1H-pyrrol-1-yl)cyclopentane-1-carboxylic acid (28a)

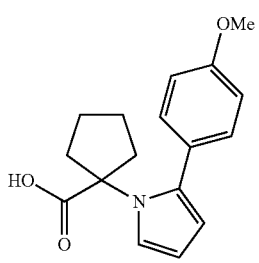

The synthetic route of the first step for compound 24a of Example 24 was repeated, wherein the starting material 3-(1,3-dioxan-2-yl)-1-phenylpropan-1-one was replaced by 3-(1,3-dioxan-2-yl)-1-(4-methoxyphenyl)propan-1-one which was prepared according to the method described in the patent document WO/2011/042477 to afford compound 28a. LCMS ESI(+): 286 (M+1)$^+$. $^1$H NMR (500 MHz, dmso-d6) δ (ppm): 12.55 (1H, s), 7.14 (2H, d, J=9.0 Hz), 6.87-6.95 (3H, m), 5.99-6.00 (1H, m), 5.87-5.88 (1H, m), 2.10-2.15 (2H, m), 1.96-1.99 (2H, m), 1.57-1.61 (4H, m).

Step 2: Dimethyl 2-(1-(2-(4-methoxyphenyl)-1H-pyrrol-1-yl)cyclopentane-1-carbonyl)malonate (28b)

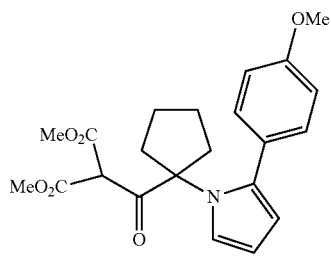

The synthetic route of the second step for compound 15b of Example 15 was repeated, wherein the starting material 15a was replaced with 28a to afford compound 28b. LCMS ESI(+): 400 (M+1)$^+$. $^1$H NMR (500 MHz, dmso-d6) δ (ppm): 7.12-7.15 (3H, m), 6.88 (2H, d, J=9.0 Hz), 6.14 (1H, t, J=9.0 Hz), 5.97-6.98 (1H, m), 3.77 (3H, s), 3.59 (6H, s), 2.24-2.33 (2H, m), 1.77-1.84 (2H, m), 1.58-1.63 (2H, m), 1.35-1.43 (2H, m).

Step 3: Methyl 6'-Hydroxy-3'-(4-methoxyphenyl)-8'-oxo-8'H-spiro[cyclopentane-1,5'-indolizine]-7'-carboxylate (28c)

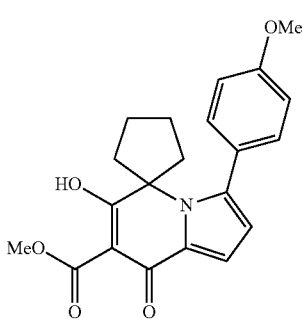

The synthetic route of the third step for compound 15c of Example 15 was repeated, wherein the starting material 15b was replaced with 28b to afford compound 28c. LCMS ESI(+): 368 (M+1)$^+$. $^1$H NMR (500 MHz, dmso-d6) δ (ppm): 13.88 (1H, s), 7.40 (2H, d, J=8.5 Hz), 7.07 (1H, d, J=4.0 Hz), 7.00 (1H, d, J=8.5 Hz), 6.31 (1H, d, J=4.0 Hz), 3.81 (6H, s), 2.22-2.27 (2H, m), 2.00-2.07 (2H, m), 1.41-1.49 (2H, m), 0.95-1.02 (2H, m).

Step 4: (6'-Hydroxy-3'-(4-methoxyphenyl)-8'-oxo-8'H-spiro[cyclopentane-1,5'-indolizine]-7'-carbonyl glycine (28)

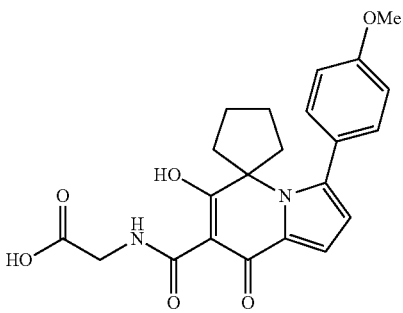

The synthetic route of the fourth step for compound 15 of Example 15 was repeated, wherein the starting material 15c was replaced with 28c to afford compound 28. LCMS ESI(+): 411 (M+1)$^+$. $^1$H NMR (500 MHz, dmso-d6) δ (ppm): 17.97 (1H, s) 12.94 (1H, s), 9.89 (1H, s), 7.42 (2H, d, J=8.5 Hz), 7.04 (1H, s), 7.01 (2H, d, J=8.5 Hz), 6.30 (1H, d, J=3.5 Hz) 4.07 (2H, d, J=5.5 Hz), 2.28-2.31 (2H, m), 2.15 (2H, s), 1.50-1.60 (2H, m), 0.94-1.02 (2H, m).

Example 29: (6'-Hydroxy-8'-oxo-3'-(4-methylphenyl)-8'H-spiro[cyclopentane-1,5'-indolizine]-7'-carbonyl) glycine (29)

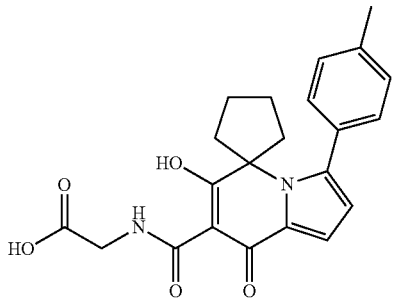

Step 1: 1-(2-(4-methylphenyl)-1H-pyrrol-1-yl)cyclopentane-1-carboxylic Acid (29a)

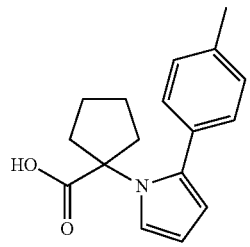

The synthetic route of the first step for compound 24a of Example 24 was repeated, wherein the starting material 3-(1,3-dioxan-2-yl)-1-phenylpropan-1-one was replaced by 3-(1,3-dioxan-2-yl)-1-(4-methylphenyl)propan-1-one which was prepared according to the method described in the patent document WO/2011/042477 to afford compound 29a. LCMS ESI(+): 270 (M+1)$^+$.

Step 2: Dimethyl 2-(1-(2-(4-methylphenyl)-1H-pyrrol-1-yl)cyclopentane-1-carbonyl)malonate (29b)

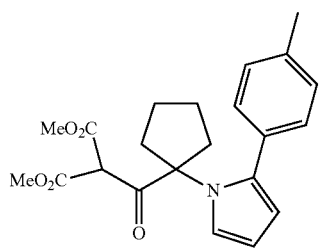

The synthetic route of the second step for compound 15b of Example 15 was repeated, wherein the starting material 15a was replaced with 29a to afford compound 29b. LCMS ESI(+): 384 (M+1)$^+$.

Step 3: Methyl 6'-hydroxy-8'-oxo-3'-(4-methylphenyl)-8'H-spiro[cyclopentane-1,5'-indolizine]-7'-carboxylate (29c)

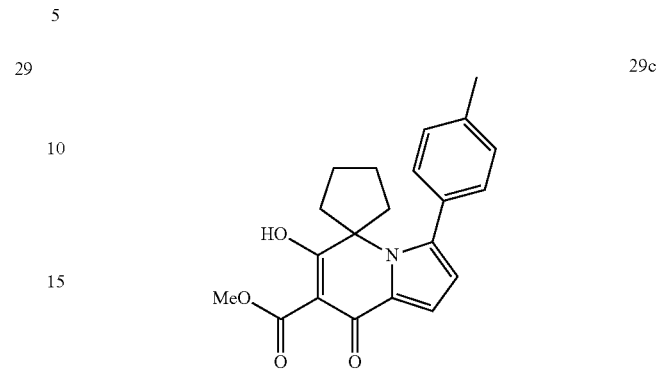

The synthetic route of the third step for compound 15c of Example 15 was repeated, wherein the starting material 15b was replaced with 29b to afford compound 29c. LCMS ESI(+): 352 (M+1)$^+$.

Step 4: (6'-Hydroxy-8'-oxo-3'-(4-methylphenyl)-8'H-spiro[cyclopentane-1,5'-indolizine]-7'-carbonyl) glycine (29)

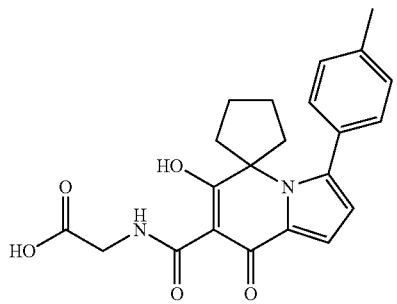

The synthetic route of the fourth step for compound 15 of Example 15 was repeated, wherein the starting material 15c was replaced with 29c to afford compound 29. LCMS ESI(+): 395 (M+1)$^+$.

Example 30: (3'-Cyclopropyl-6'-hydroxy-8'-oxo-8'H-spiro[cyclohexane-1,5'-indolizine]-7'-carbonyl) glycine (M)

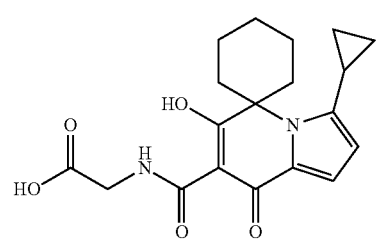

Step 1: 1-(2-cyclopropyl-1H-pyrrol-1-yl)cyclohexane-1-carboxylic Acid (30a)

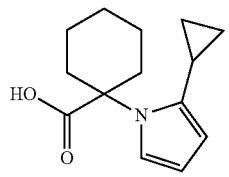
30a

The synthetic route of the first step for compound 24a of Example 24 was repeated, wherein the starting materials 3-(1,3-dioxan-2-yl)-1-phenylpropan-1-one and 1-amino-cyclopentane-1-carboxylic acid were respectively replaced by 1-cyclopentyl-3-(1,3-dioxan-2-yl) propan-1-one, which was prepared according to the method described in the patent document WO/2011/042477, and 1-amino-cyclohexane-1-carboxylic acid to afford compound 30a. LCMS ESI(+): 234 (M+1)+. 1H NMR (500 MHz, DMSO-d6) δ 12.35 (s, 1H), 6.84 (dd, 1H), 5.82 (t, 1H), 5.66 (dd, 1H), 2.39~2.35 (m, 2H), 2.14~2.09 (m, 2H), 1.73~1.69 (m, 1H), 1.62~1.56 (m, 4H), 1.39~1.36 (m, 2H), 0.79~0.74 (m, 2H), 0.55~0.52 (m, 2H).

Step 2: Dimethyl 2-(1-(2-cyclopropyl-1H-pyrrol-1-yl)cyclohexane-1-carbonyl)malonate (30b)

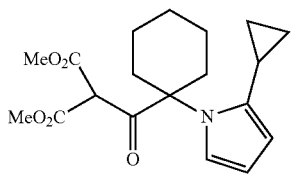
30b

The synthetic route of the second step for compound 15b of Example 15 was repeated, wherein the starting material 15a was replaced with 30a to afford compound 30b. LCMS ESI(+): 348 (M+1)+. 1H NMR (500 MHz, CDCl3) δ 6.86 (td, 1H), 6.16 (t, 1H) 5.85-5.84 (m, 1H), 4.27 (s, 1H), 3.68 (s, 6H), 2.60-2.57 (m, 2H), 2.21 (t, 2H), 1.69-1.67 (m, 1H), 1.50-1.42 (m, 2H), 1.39-1.30 (m, 2H), 1.18-1.07 (m, 2H), 0.82-0.80 (m, 2H), 0.69-0.66 (m, 2H).

Step 3: Methyl 3'-Cyclopropyl-6'-hydroxy-8'-oxo-8'H-spiro[methylcyclo-1,5'-indolizine]-7'-carboxylate (311c)

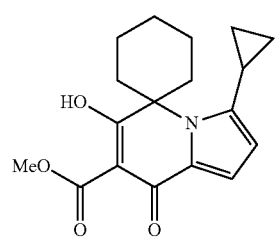
30c

The synthetic route of the third step for compound 15c of Example 15 was repeated, wherein the starting material 15b was replaced with 30b to afford compound 30c. LCMS ESI(+): 316 (M+1)+. 1H NMR (500 MHz, CDCl3) δ 14.20 (s, 1H), 6.98 (d, 1H), 6.01 (d, 1H), 3.95 (s, 3H), 2.59~2.56 (m, 2H), 2.20~2.18 (m, 2H), 1.85~1.82 (m, 1H), 1.50~1.45 (m, 2H), 1.34~1.30 (m, 2H), 1.16~1.12 (m, 2H), 0.88 (dd, 2H), 0.82 (dd, 2H).

Step 4: (6'-Hydroxy-3'-cyclopropyl-8'-oxo-8'H-spiro[cyclohexane-1,5'-indolizine]-7'-carbonyl)glycine (30)

30

The synthetic route of the fourth step for compound 15 of Example 15 was repeated, wherein the starting material 15c was replaced with 30c to afford compound 30. LCMS ESI(+): 359 (M+1)+. 1H NMR (500 MHz, DMSO-d6) δ 17.81 (s, 1H), 12.94 (s, 1H), 9.90 (s, 1H), 6.88 (d, 1H), 6.15 (d, 1H), 4.02 (br, 2H), 2.59-2.57 (m, 2H), 2.25-2.24 (m, 2H), 2.07-2.04 (m, 2H), 1.96-1.91 (m, 2H), 1.76-1.71 (m, 3H), 1.14 (dt, 2H), 0.85 (dt, 2H).

Example 31: (3'-tert-Butyl-6'-hydroxy-8'-oxo-8'H-spiro[cyclohexane-1,5'-indolizine]-7'-carbonyl)glycine (31)

31

Step 1: 1-(2-tert-Butyl-1H-pyrrol-1-yl)cyclohexane-1-carboxylic Acid (31a)

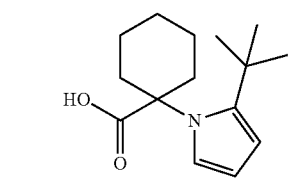
31a

The synthetic route of the first step for compound 30a of Example 30 was repeated, wherein the starting material 1-cyclopropyl-3-(1,3-dioxan-2-yl)propan-1-one was replaced by 1-(1,3-dioxan-2-yl)-4,4-dimethylpentan-3-one which was prepared according to the method described in the patent document WO/2011/042477 to afford compound 31a. LCMS ESI(+): 250 (M+1)+.

Step 2: Dimethyl 2-(1-(2-tert-butyl-1H-pyrrol-1-yl)cyclohexane-1-carbonyl)malonate (31b)

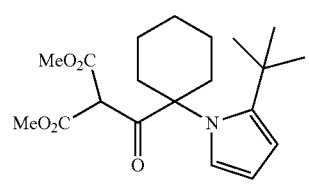

31b

The synthetic route of the second step for compound 15b of Example 15 was repeated, wherein the starting material 15a was replaced with 31a to afford compound 31b. LCMS ESI(+): 364 (M+1)+.

Step 3: Methyl 3'-tert-Butyl-6'-hydroxy-8'-oxo-8'H-spiro[cyclohexane-1,5'-indolizine]-7'-carboxylate (31c)

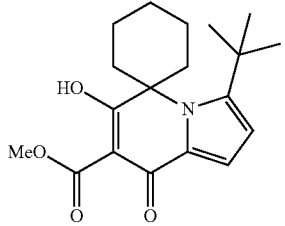

31c

The synthetic route of the third step for compound 15c of Example 15 was repeated, wherein the starting material 15b was replaced with 31b to afford compound 31c. LCMS ESI(+): 332 (M+1)+.

Step 4: (6'-Hydroxy-3'-tert-butyl-8'-oxo-8'H-spiro[cyclohexane-1,5'-indolizine]-7'-carbonyl)glycine (31)

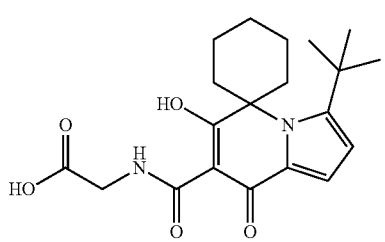

31

The synthetic route of the fourth step for compound 15 of Example 15 was repeated, wherein the starting material 15c was replaced with 31c to afford compound 31. LCMS ESI(+): 375 (M+1)+.

Example 32: (6'-Hydroxy-3'-methyl-8'-oxo-8'H-spiro[cyclohexane-1,5'-indolizine]-7'-carbonyl)glycine (32)

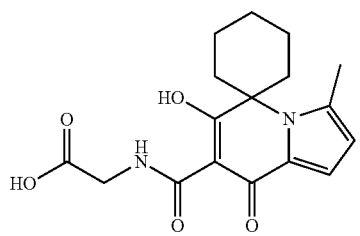

32

Step 1: 1-(2-methyl-1H-pyrrol-1-yl)cyclohexane-1-carboxylic Acid (32a)

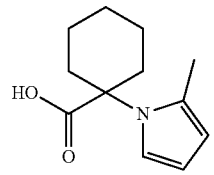

32a

The synthetic route of the first step for compound 30a of Example 30 was repeated, wherein the starting material 1-cyclopropyl-3-(1,3-dioxan-2-yl)propan-1-one was replaced by 4-(1,3-dioxan-2-yl)butan-2-one which was prepared according to the method described in the patent document WO/2011/042477 to afford compound 32a. LCMS ESI(+): 208 (M+1)+. $^1$H NMR (500 MHz, dmso-d6) δ (ppm): 12.90 (1H, s), 6.85 (1H, t, J=3.0 Hz), 5.86 (1H, t, J=3.0 Hz), 5.76 (1H, s), 2.25-2.32 (2H, m), 2.16 (3H, s), 1.50-1.61 (6H, m), 1.29-1.38 (2H, m).

Step 2: Dimethyl 2-(1-(2-methyl-1H-pyrrol-1-yl)cyclohexane-1-carbonyl)malonate (32b)

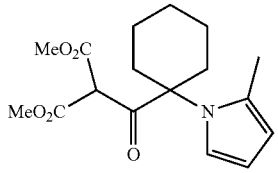

32b

The synthetic route of the second step for compound 15b of Example 15 was repeated, wherein the starting material 15a was replaced with 32a to afford compound 32b. LCMS ESI(+): 322 (M+1)+. 1H NMR (500 MHz, dmso-d6) δ (ppm): 6.97 (1H, t, J=2.5 Hz), 6.03 (1H, t, J=3.0 Hz), 5.86 (1H, s), 4.97 (1H, s), 2.16 (3H, s), 3.56 (6H, s), 2.20-2.30 (2H, m), 2.02-2.12 (2H, m), 1.55-1.63 (2H, m), 1.40-1.55 (4H, m).

Step 3: Methyl 6'-Hydroxy-3'-methyl-8'-oxo-8'H-spiro[methylcyclo-1,5'-indolizine]-7'-carboxylate (32c)

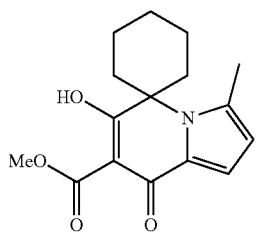

The synthetic route of the third step for compound 15c of Example 15 was repeated, wherein the starting material 15b was replaced with 32b to afford compound 32c. LCMS ESI(+): 290 (M+1)+. 1H NMR (500 MHz, dmso-d6) δ (ppm): 13.73 (1H, s), 6.95 (1H, d, J=4.0 Hz), 6.28 (1H, d, J=4.0 Hz), 3.80 (3H, s), 3.80 (3H, s), 2.10-2.18 (2H, m), 1.84-1.93 (4H, m), 1.60-1.74 (4H, m).

Step 4: (6'-Hydroxy-3'-methyl-8'-oxo-8'H-spiro[cyclohexane-1,5'-indolizine]-7'-carbonyl)glycine (32)

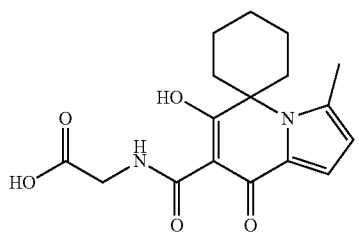

The synthetic route of the fourth step for compound 15 of Example 15 was repeated, wherein the starting material 15c was replaced with 32c to afford compound 32. LCMS ESI(+): 333 (M+1)+. 1H NMR (500 MHz, dmso-d6) δ (ppm): 17.78 (1H, s) 12.92 (1H, s), 9.89 (1H, s), 6.92 (1H, d, J=4.0 Hz), 6.30 (1H, d, J=4.0 Hz), 4.05 (2H, d, J=5.0 Hz), 2.63 (3H, s), 2.16-2.24 (2H, m), 1.96-2.05 (4H, m), 1.65-1.78 (4H, m), 1.41-1.46 (1H, m).

Example 33: (3'-(4-Chlorophenyl)-6'-hydroxy-8'-oxo-8'H-spiro[cyclopentane-1,5'-indolizine]-7'-carbonyl)-D-alanine (33)

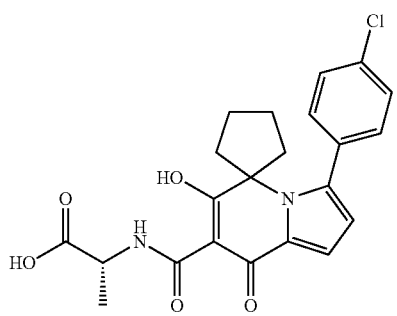

Step 1: (3'-(4-Chlorophenyl)-6'-hydroxy-8'-oxo-8'H-spiro[cyclopentane-1,5'-indolizine]-7'-carbonyl)-D-alanine (33)

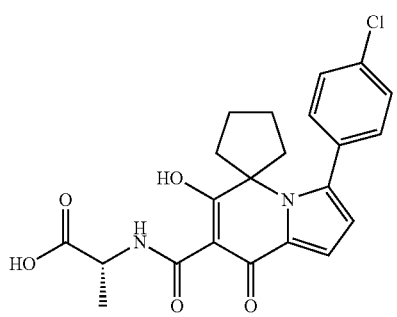

The synthetic route of the first step for compound 27 of Example 27 was repeated, wherein the starting material L-alanine was replaced by D-alanine to afford compound 33. LCMS ESI(+): 429 (M+1)+. 1H NMR (500 MHz, dmso-d6) δ (ppm): 17.89 (1H, s), 13.14 (1H, br s), 10.00 (1H, s), 7.57-7.53 (4H, m), 7.06 (1H, s), 6.37 (1H, d, J=3.0 Hz), 4.51-4.45 (1H, m), 2.36-2.31 (2H, m), 2.12-2.08 (2H, m), 1.58 (2H, br s), 1.43 (2H, d, J=7.0 Hz), 1.02-0.97 (2H, m).

Example 34: (3'-Cyclobutyl-6'-hydroxy-8'-oxo-8'H-spiro[cyclohexane-1,5'-indolizine]-7'-carbonyl)glycine (34)

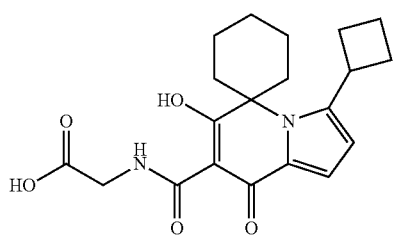

Step 1: 1-(2-Cyclobutyl-1H-pyrrol-1-yl)cyclohexane-1-carboxylic Acid (34a)

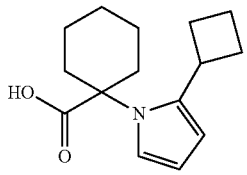

The synthetic route of the first step for compound 30a of Example 30 was repeated, wherein the starting material 1-cyclopropyl-3-(1,3-dioxan-2-yl)propan-1-one was replaced by 1-cyclobutyl-3-(1,3-dioxan-2-yl)propan-2-one which was prepared according to the method described in the patent document WO/2011/042477 to afford compound 34a. LCMS ESI(+): 248 (M+1)$^+$.

Step 2: Dimethyl 2-(1-(2-cyclobutyl-1H-pyrrol-1-yl)cyclohexane-1-carbonyl)malonate (34b)

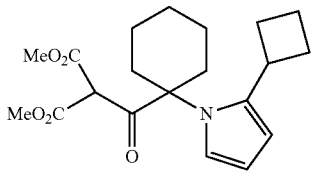

The synthetic route of the second step for compound 15b of Example 15 was repeated, wherein the starting material 15a was replaced with 34a to afford compound 34b. LCMS ESI(+): 362 (M+1)$^+$. $^1$H NMR (500 MHz, DMSO-d6) δ 6.98 (dd, J=3.1, 1.8 Hz, 1H), 6.17 (dd, J=3.7, 1.7 Hz, 1H), 6.12 (t, J=3.3 Hz, 1H), 4.36 (s, 1H), 3.54 (d, J=2.1 Hz, 6H), 2.95 (m, J=8.2 Hz, 1H), 2.27-2.13 (m, 4H), 2.04-1.91 (m, 4H), 1.78 (dtd, J=16.4, 8.6, 3.5 Hz, 2H), 1.65-1.56 (m, 2H), 1.43 (d, 4H).

Step 3: Methyl 3'-Cyclobutyl-6'-hydroxy-8'-oxospiro[cyclohexane-1,5'-indolizine]-7'-carboxylate (34c)

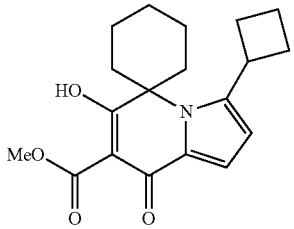

The synthetic route of the third step for compound 15c of Example 15 was repeated, wherein the starting material 15b was replaced with 34b to afford compound 34c. LCMS ESI(+): 330 (M+1)$^+$.

Step 4: (3'-Cyclobutyl-6'-hydroxy-8'-oxo-8'H-spiro[cyclohexane-1,5'-indolizine]-7'-carbonyl)glycine (34)

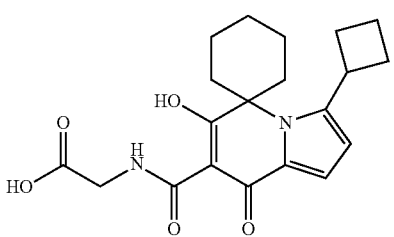

The synthetic route of the fourth step for compound 15 of Example 15 was repeated, wherein the starting material 15c was replaced with 34c to afford compound 34. LCMS ESI(+): 373 (M+1)$^+$. $^1$H NMR (500 MHz, DMSO-d$_6$) δ 17.77 (s, 1H), 12.93 (s, 1H), 9.88 (s, 1H), 6.98 (d, J=4.3 Hz, 1H), 6.67 (d, J=4.3 Hz, 1H), 4.05 (d, J=5.4 Hz, 2H), 3.95 (t, J=8.6 Hz, 1H), 2.44-2.38 (m, 2H), 2.17 (t, J=9.9 Hz, 2H), 2.07-1.93 (m, 6H), 1.88-1.74 (m, 4H), 1.51 (s, 2H).

Example 35: (6'-Hydroxy-8'-oxo-3'-phenyl-8'H-spiro[cyclohexane-1,5'-indolizine]-7'-carbonyl)glycine (35)

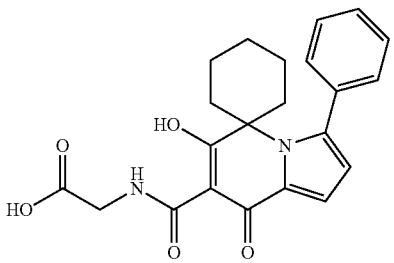

Step 1: 1-(2-phenyl-1H-pyrrol-1-yl)cyclohexane-1-carboxylic Acid (35a)

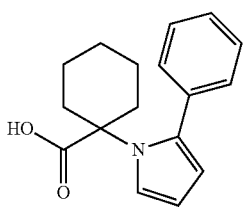

The synthetic route of the first step for compound 30a of Example 30 was repeated, wherein the starting material 1-cyclopropyl-3-(1,3-dioxan-2-yl)propan-1-one was replaced by 3-(1,3-dioxan-2-yl)-1-phenylpropan-1-one which was prepared according to the method described in the patent document WO/2011/042477 to afford compound 35a. LCMS ESI(+): 270 (M+1)$^+$. $^1$H NMR (500 MHz, DMSO-d6) δ (ppm): 12.92 (1H, s) 7.34-7.30 (3H, m), 7.25-7.21 (2H, m), 7.04 (1H, m), 6.07 (1H, t), 5.92 (1H, dd), 2.05-1.23 (10H, m).

Step 2: Dimethyl 2-(1-(2-phenyl-1H-pyrrol-1-yl) cyclohexane-1-carbonyl)malonate (35b)

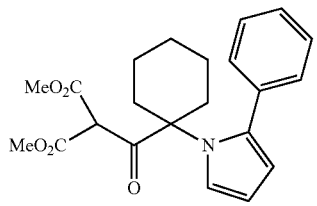

35b

The synthetic route of the second step for compound 15b of Example 15 was repeated, wherein the starting material 15a was replaced with 35a to afford compound 35b. LCMS ESI(+): 384 (M+1)⁺. ¹H NMR (500 MHz, dmso-d6) δ (ppm): 7.33-7.30 (m, 3H), 7.24-7.22 (m, 2H), 7.18-7.17 (m, 1H), 6.22-6.20 (t, 1H), 5.98-6.00 (m, 1H), 5.19 (s, 1H), 3.62 (s, 6H), 2.13-1.22 (m, 10H).

Step 3: Methyl 6'-Hydroxy-8'-oxo-3'-phenyl-8'H-spiro[methylcyclo-1,5'-indolizine]-7'-carboxylate (35c)

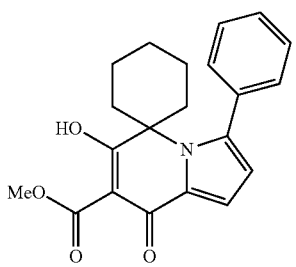

35c

The synthetic route of the third step for compound 15c of Example 15 was repeated, wherein the starting material 15b was replaced with 35b to afford compound 35c. LCMS ESI(+): 352 (M+1)⁺. ¹H NMR (500 MHz, DMSO-d6) δ (ppm): 13.53 (1H, s), 7.49-7.44 (5H, m), 7.10-7.09 (1H, d), 6.30-6.31 (1H, d), 3.81 (3H, s), 2.0-1.3 (10H, m).

Step 4: (6'-Hydroxy-8'-oxo-3'-phenyl-8'H-spiro[cyclohexane-1,5'-indolizine]-7'-carbonyl)glycine (35)

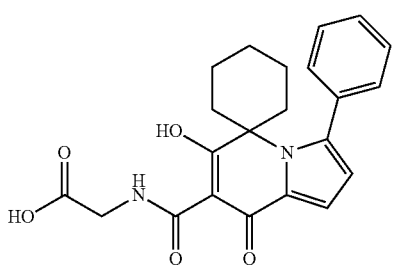

35

The synthetic route of the fourth step for compound 15 of Example 15 was repeated, wherein the starting material 15c was replaced with 35c to afford compound 35. LCMS ESI(+): 395 (M+1)⁺. ¹H NMR (500 MHz, DMSO-d6) δ (ppm): 12.92 (1H, s, OH), 9.79 (1H, t, NH), 7.51-7.47 (5H, m), 7.09-7.08 (1H, d), 6.34-6.33 (1H, d), 4.07-4.06 (2H, d), 2.14-1.79 (10H, m).

Example 36: (3'-(4-Chlorophenyl)-6'-hydroxy-8'-oxo-8'H-spiro[cyclohexane-1,5'-indolizine]-7'-carbonyl) glycine (36)

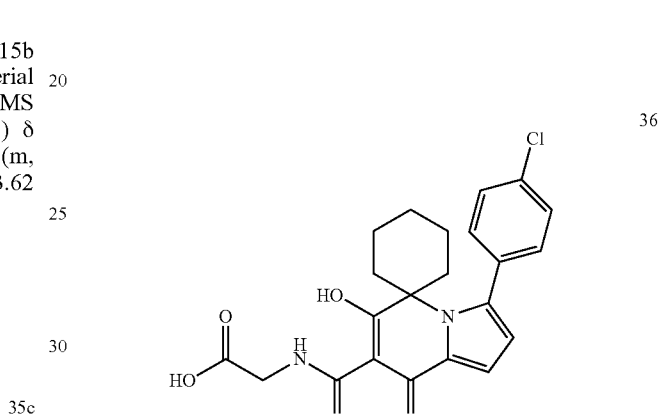

36

Step 1: 1-(2-(4-Chlorophenyl)-1H-pyrrol-1-yl)cyclohexane-1-carboxylic Acid

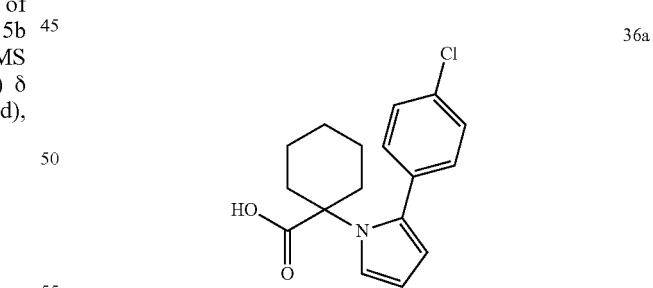

36a

The synthetic route of the first step for compound 30a of Example 30 was repeated, wherein the starting material 1-cyclopropyl-3-(1,3-dioxan-2-yl)propan-1-one was replaced by 3-(1,3-dioxan-2-yl)-1-(4-chlorophenyl)propan-1-one which was prepared according to the method described in the patent document WO/2011/042477 to afford compound 36a. LCMS ESI(+): 304 (M+1)⁺.

Step 2: Dimethyl 2-(1-(2-(4-chlorophenyl)-1H-pyrrol-1-yl)cyclohexane-1-carbonyl)malonate (36b)

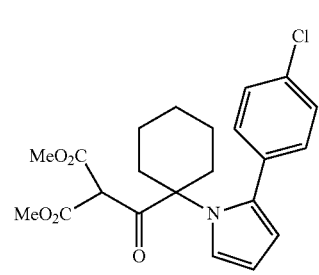

36b

The synthetic route of the second step for compound 15b of Example 15 was repeated, wherein the starting material 15a was replaced with 36a to afford compound 36b. LCMS ESI(+): 418 (M+1)$^+$.

Step 3: Methyl 3'-(4-Chlorophenyl)-6'-hydroxy-8'-oxo-8'H-spiro[cyclohexane-1,5'-indolizine]-7'-carboxylate (36c)

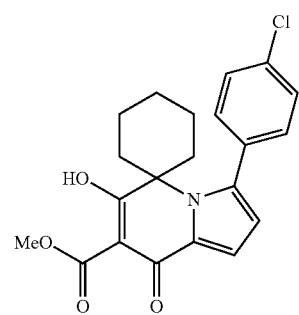

36c

The synthetic route of the third step for compound 15c of Example 15 was repeated, wherein the starting material 15b was replaced with 36b to afford compound 36c. LCMS ESI(+): 386 (M+1)$^+$.

Step 4: (3'-(4-Chlorophenyl)-6'-hydroxy-8'-oxo-8'H-spiro[cyclohexane-1,5'-indolizine]-7'-carbonyl) glycine (36)

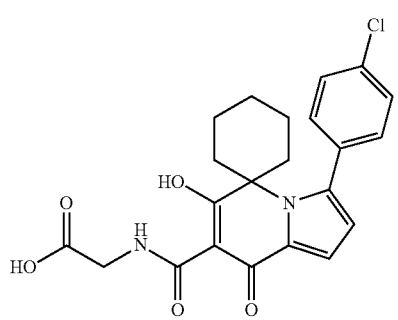

36

The synthetic route of the fourth step for compound 15 of Example 15 was repeated, wherein the starting material 15c was replaced with 36c to afford compound 36. LCMS ESI(+): 429 (M+1)$^+$.

Example 37: (3'-(4-Fluorophenyl)-6'-hydroxy-8'-oxo-8'H-spiro[cyclohexane-1,5'-indolizine]-7'-carbonyl) glycine (37)

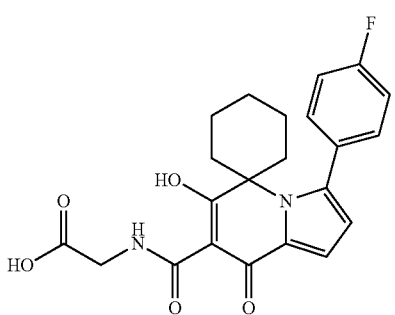

37

Step 1: 1-(2-(4-Fluorophenyl)-1H-pyrrol-1-yl)cyclohexane-1-carboxylic Acid (37a)

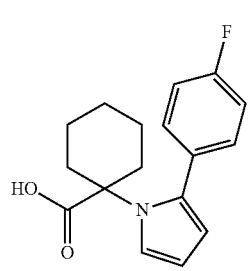

37a

The synthetic route of the first step for compound 30a of Example 30 was repeated, wherein the starting material 1-cyclopropyl-3-(1,3-dioxan-2-yl)propan-1-one was replaced by 3-(1,3-dioxan-2-yl)-1-(4-fluorophenyl)propan-1-one which was prepared according to the method described in the patent document WO/2011/042477 to afford compound 37a. LCMS ESI(+): 288 (M+1)$^+$.

Step 2: Dimethyl 2-(1-(2-(4-fluorophenyl)-1H-pyrrol-1-yl)cyclohexane-1-carbonyl)malonate (37b)

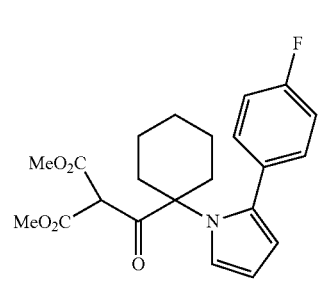

37b

The synthetic route of the second step for compound 15b of Example 15 was repeated, wherein the starting material 15a was replaced with 37a to afford compound 37b. LCMS ESI(+): 402 (M+1)+.

Step 3: Methyl 3'-(4-Fluorophenyl)-6'-hydroxy-8'-oxo-8'H-spiro[methylcyclo-1,5'-indolizine]-7'-carboxylate (37c)

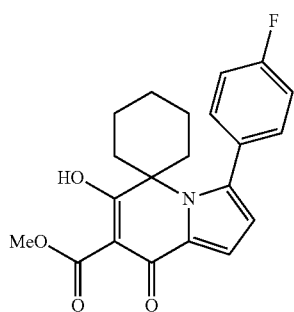

37c

The synthetic route of the third step for compound 15c of Example 15 was repeated, wherein the starting material 15b was replaced with 37b to afford compound 37c. LCMS ESI(+): 370 (M+1)+.

Step 4: (3'-(4-Fluorophenyl)-6'-hydroxy-8'-oxo-8'H-spiro[cyclohexane-1,5'-indolizine]-7'-carbonyl) glycine (37)

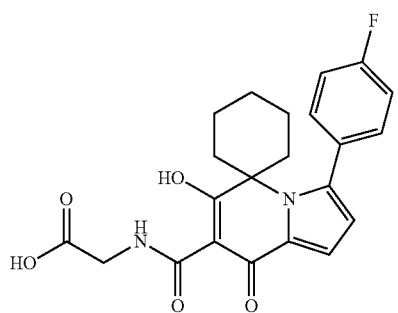

37

The synthetic route of the fourth step for compound 15 of Example 15 was repeated, wherein the starting material 15c was replaced with 37c to afford compound 37. LCMS ESI(+): 413 (M+1)+.

Example 38: (6'-Hydroxy-3'-(4-methoxyphenyl)-8'-oxo-8'H-spiro[cyclohexane-1,5'-indolizine]-7'-carbonyl glycine (38)

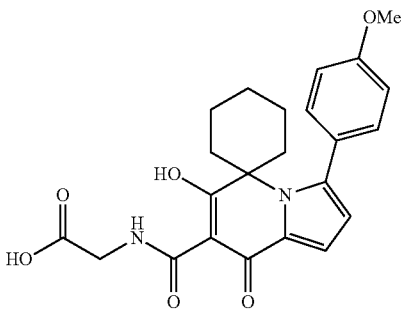

38

Step 1: 1-(2-(4-methoxyphenyl)-1H-pyrrol-1-yl) cyclohexane-1-carboxylic Acid (38a)

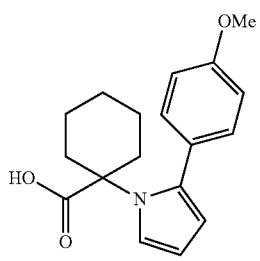

38a

The synthetic route of the first step for compound 30a of Example 30 was repeated, wherein the starting material 1-cyclopropyl-3-(1,3-dioxan-2-yl)propan-1-one was replaced by 3-(1,3-dioxan-2-yl)1-(4-methoxyphenyl)propan-1-one which was prepared according to the method described in the patent document WO/2011/042477 to afford compound 38a. LCMS ESI(+): 300 (M+1)+.

Step 2: Dimethyl 2-(1-(2-(4-methoxyphenyl)-1H-pyrrol-1-yl)cyclohexane-1-carbonyl)malonate (38b)

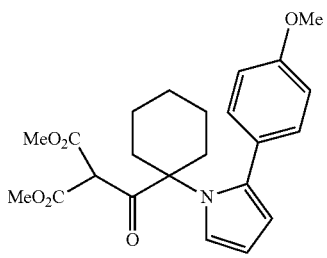

38b

The synthetic route of the second step for compound 15b of Example 15 was repeated, wherein the starting material 15a was replaced with 38a to afford compound 38b. LCMS ESI(+): 414 (M+1)+.

Step 3: Methyl 6'-Hydroxy-3'-(4-methoxyphenyl)-8'-oxo-8'H-spiro[cyclohexane-1,5'-indolizine]-7'-carboxylate (38c)

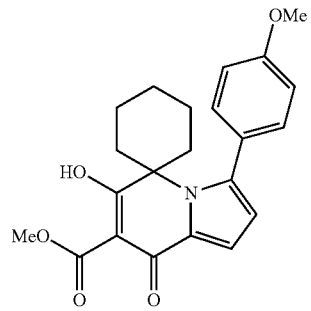
38c

The synthetic route of the third step for compound 15c of Example 15 was repeated, wherein the starting material 15b was replaced with 38b to afford compound 38c. LCMS ESI(+): 382 (M+1)⁺.

Step 4: (6'-Hydroxy-3 (4-methoxyphenyl)-8'-oxo-8'H-spiro[cyclohexane-1,5'-indolizine]-7'-carbonyl glycine (38)

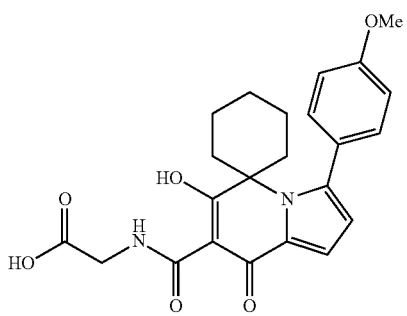
38

The synthetic route of the fourth step for compound 15 of Example 15 was repeated, wherein the starting material 15c was replaced with 38c to afford compound 38. LCMS ESI(+): 425 (M+1)⁺.

Example 39: (6'-Hydroxy-8'-oxo-3'-phenyl-8'H-spiro[cyclobutane-1,5'-indolizine]-7'-carbonyl)glycine (39)

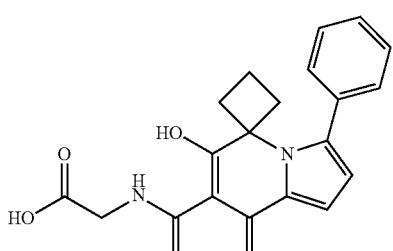
39

Step 1: 1-(2-phenyl-1H-pyrrol-1-yl)cyclobutane-1-carboxylic Acid (39a)

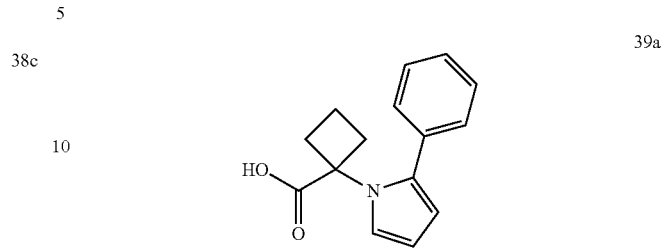
39a

The synthetic route of the first step for compound 24a of Example 24 was repeated, wherein the starting material 1-amino-cyclopentane-1-carboxylic acid was replaced by 1-amino-cyclobutane-1-carboxylic acid to afford compound 39a. LCMS ESI(+): 242 (M+1)⁺.

Step 2: Dimethyl 2-(1-(2-phenyl-1H-pyrrol-1-yl)cyclobutane-1-carbonyl)malonate (39b)

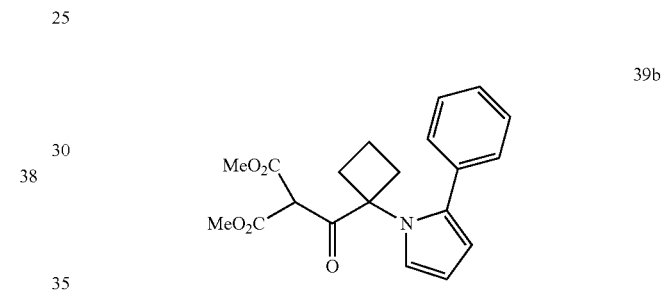
39b

The synthetic route of the second step for compound 15b of Example 15 was repeated, wherein the starting material 15a was replaced with 39a to afford compound 39b. LCMS ESI(+): 356 (M+1)⁺. ¹H NMR (500 MHz, DMSO-d6) δ 7.36-7.28 (m, 3H), 7.23-7.16 (m, 2H), 7.08 (dd, J=3.0, 1.9 Hz, 1H), 6.19 (t, J=3.2 Hz, 1H), 6.13 (dd, J=3.5, 1.8 Hz, 1H), 5.14 (s, 1H), 3.59 (s, 6H), 2.45 (s, 2H), 2.31 (s, 2H), 1.78-1.59 (m, 2H).

Step 3: Methyl 6'-Hydroxy-8'-oxo-3'-phenyl-8'H-spiro[cyclobutane-1,5'-indolizine]-7'-carboxylate (39c)

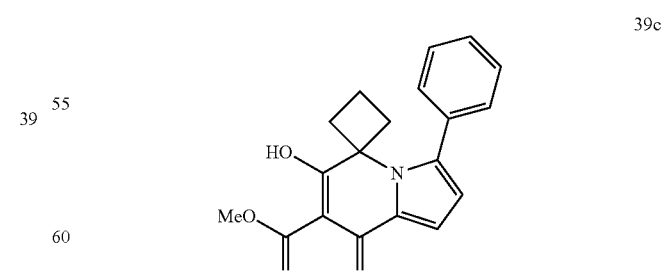
39c

The synthetic route of the third step for compound 15c of Example 15 was repeated, wherein the starting material 15b was replaced with 39b to afford compound 39c. LCMS ESI(+): 324 (M+1)⁺.

Step 4: (6'-Hydroxy-8'-oxo-3'-phenyl-8'H-spiro[cyclobutane-1,5'-indolizine]-7'-carbonyl)glycine (39)

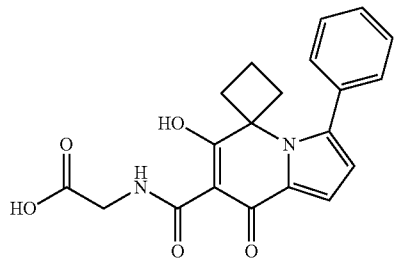

The synthetic route of the fourth step for compound 15 of Example 15 was repeated, wherein the starting material 15c was replaced with 39c to afford compound 39. LCMS ESI(+): 367 (M+1)$^+$. $^1$H NMR (500 MHz, DMSO-d$_6$) δ 17.92 (s, 1H), 12.99 (s, 1H), 9.98 (d, J=6.9 Hz, 1H), 7.68-7.62 (m, 2H), 7.55-7.50 (m, 3H), 7.08 (d, J=4.0 Hz, 1H), 6.41 (d, J=4.1 Hz, 1H), 4.09 (d, J=5.5 Hz, 2H), 2.59 (td, J=18.7, 18.3, 6.3 Hz, 4H), 1.71 (q, J=9.4 Hz, 1H), 1.09-0.99 (m, 1H).

Example 40: (6'-Hydroxy-8'-oxo-3'-phenyl-8'H-spiro[cyclopropane-1,5'-indolizine]-7'-carbonyl)glycine (40)

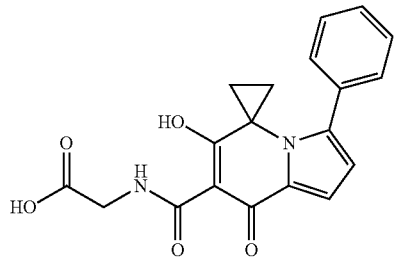

Step 1: 1-(2-phenyl-1H-pyrrol-1-yl)cyclopropane-1-carboxylic Acid (40a)

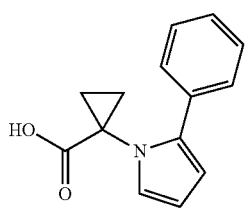

The synthetic route of the first step for compound 24a of Example 24 was repeated, wherein the starting material 1-amino-cyclopentane-1-carboxylic acid was replaced by 1-amino-cyclopropane-1-carboxylic acid to afford compound 40a. LCMS ESI(+): 228 (M+1)$^+$. $^1$H NMR (500 MHz, DMSO-d6) δ 12.97 (s, 1H), 7.40-7.35 (m, 4H), 7.30-7.26 (m, 1H), 6.93 (dd, 1H), 6.13 (dd, 1H), 6.06 (t, 1H), 1.90-1.85 (m, 4H).

Step 2: Dimethyl 2-(1-(2-phenyl-1H-pyrrol-1-yl)cyclopropane-1-carbonyl)malonate (40b)

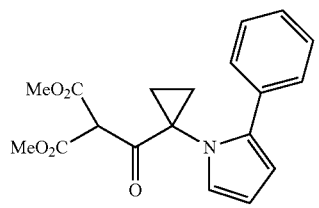

The synthetic route of the second step for compound 15b of Example 15 was repeated, wherein the starting material 15a was replaced with 40a to afford compound 40b. LCMS ESI(+): 342 (M+1)$^+$. $^1$H NMR (500 MHz, DMSO-d6) δ 7.41-7.29 (m, 5H), 6.84 (dd, 1H), 6.33 (dd, 1H), 6.20 (t, 1H), 4.51 (s, 1H), 3.71 (s, 3H), 3.60 (s, 3H), 1.90-1.85 (m, 4H).

Step 3: Methyl 6'-Hydroxy-8'-oxo-3'-phenyl-8'H-spiro[cyclopropane-1,5'-indolizine]-7'-carboxylate (40c)

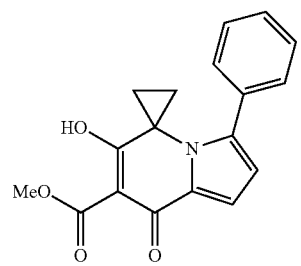

The synthetic route of the third step for compound 15c of Example 15 was repeated, wherein the starting material 15b was replaced with 40b to afford compound 40c. LCMS ESI(+): 310 (M+1)$^+$. $^1$H NMR (500 MHz, DMSO-d6) δ 13.91 (s, 1H), 7.52-7.12 (m, 5H), 6.33 (s, 1H), 6.32 (d, 1H), 3.80 (s, 3H), 1.40~1.32 (m, 4H).

Step 4: (6'-Hydroxy-8'-oxo-3'-phenyl-8'H-spiro[cyclopropane-1,5'-indolizine]-7'-carbonyl)glycine (40)

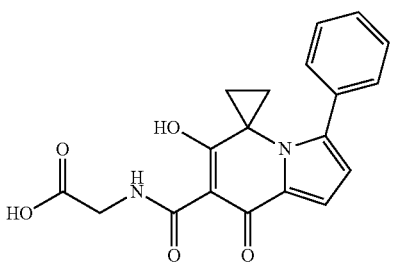

The synthetic route of the fourth step for compound 15 of Example 15 was repeated, wherein the starting material 15c was replaced with 40c to afford compound 40. LCMS ESI(+): 353 (M+1)+. $^1$H NMR (500 MHz, DMSO-d6) δ 17.95 (s, 1H), 12.96 (s, 1H), 9.92 (s, 1H), 7.54-7.44 (m, 5H), 7.10 (s, 1H), 6.33 (s, 1H), 4.07 (d, 2H), 1.50-1.46 (m, 4H).

Example 41: (6-Hydroxy-5,5-dimethyl-8-oxo-3-phenyl-5,8-dihydroindolizin-7-carbonyl)glycine (41)

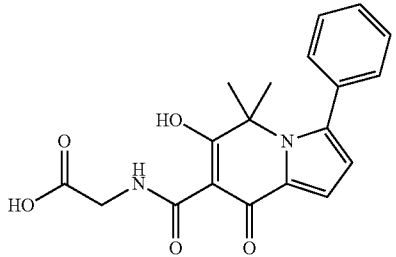

41

Step 1: 2-methyl-2-(2-phenyl-1H-pyrrol-1-yl)propionic Acid (41a)

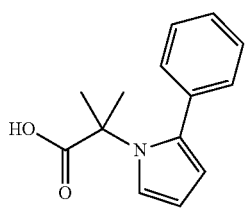

41a

The synthetic route of the first step for compound 24a of Example 24 was repeated, wherein the starting material 1-amino-cyclopentane-1-carboxylic acid was replaced by 2-amino-isobutane-1-carboxylic acid to afford compound 41a. LCMS ESI(+): 230 (M+1)+.

Step 2: Dimethyl 2-(2-methyl-2-(2-phenyl-1H-pyrrol-1-yl)propanoyl)malonate (41b)

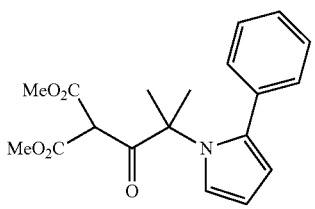

41b

The synthetic route of the second step for compound 15b of Example 15 was repeated, wherein the starting material 15a was replaced with 41a to afford compound 41b. LCMS ESI(+): 344 (M+1)+. $^1$H NMR (500 MHz, DMSO-d$_6$) δ 7.33 (dt, J=4.6, 2.9 Hz, 3H), 7.23 (dd, J=6.5, 3.0 Hz, 2H), 7.00 (dd, J=3.0, 1.9 Hz, 1H), 6.15 (t, J=3.3 Hz, 1H), 6.00 (dd, J=3.5, 1.8 Hz, 1H), 5.04 (s, 1H), 3.63 (s, 6H), 1.49 (s, 6H).

Step 3: Methyl 6-hydroxy-5,5-dimethyl-8-oxo-3-phenyl-5,8-dihydroindolizin-7-carboxylate (41c)

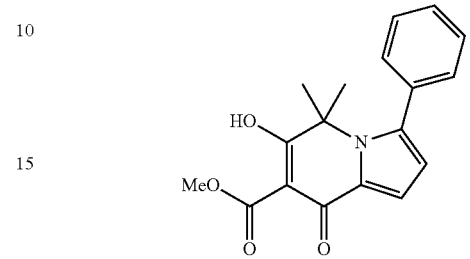

41c

The synthetic route of the third step for compound 15c of Example 15 was repeated, wherein the starting material 15b was replaced with 41b to afford compound 41c. LCMS ESI(+): 312 (M+1)+.

Step 4: (6-Hydroxy-5,5-dimethyl-8-oxo-3-phenyl-5,8-dihydroindolizin-7-carbonyl)glycine (41)

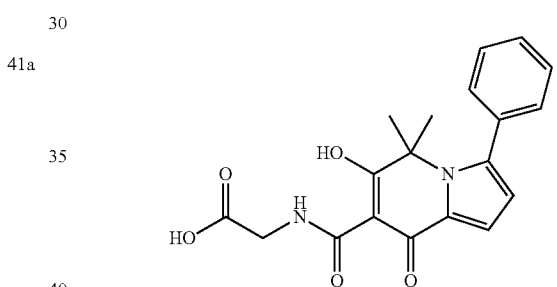

41

The synthetic route of the fourth step for compound 15 of Example 15 was repeated, wherein the starting material 15c was replaced with 41c to afford compound 41. LCMS ESI(+): 355 (M+1)+. $^1$H NMR (500 MHz, DMSO-d$_6$) δ 18.02 (s, 1H), 12.97 (s, 1H), 9.90 (t, J=5.6 Hz, 1H), 7.55-7.43 (m, 5H), 7.14-7.04 (m, 1H), 6.34 (d, J=4.1 Hz, 1H), 4.09 (d, J=5.5 Hz, 2H), 1.46 (s, 6H).

Example 42: (6'-Hydroxy-8'-oxo-3'-phenyl-8'H-spiro[cyclopentane-1,5'-indolizine]-7'-carbonyl)-L-alanine (42)

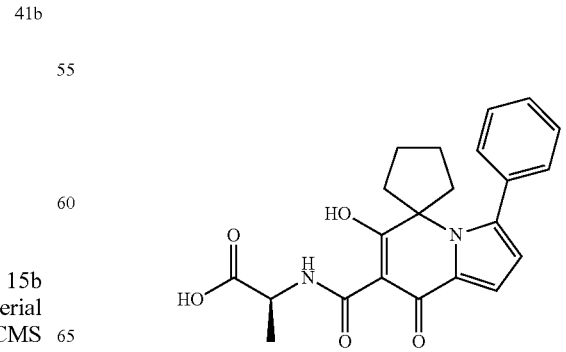

42

Step 1: (6'-Hydroxy-8'-oxo-3'-phenyl-8'H-spiro[cyclopentane-1,5'-indolizine]-7'-carbonyl)-L-alanine (42)

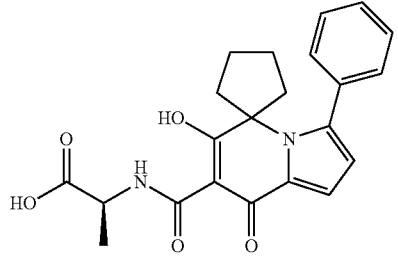

The synthetic route of the first step for compound 24 of Example 15 was repeated, wherein the starting material glycine was replaced with L-alanine to afford compound 42. LCMS ESI(+): 395 (M+1)$^+$. $^1$H NMR (500 MHz, dmso-d6) δ ppm 17.96-17.79 (m, 1H), 13.11 (s, 1H), 9.99 (s, 1H), 7.49 (tdd, J=8.4, 6.2, 3.2 Hz, 5H), 7.07 (d, J=3.8 Hz, 1H), 6.35 (d, J=3.8 Hz, 1H), 4.47 (q, J=7.1 Hz, 1H), 2.29 (s, 2H), 2.14 (s, 2H), 1.53 (s, 2H), 1.43 (d, J=7.2 Hz, 3H), 0.91 (dt, J=12.1, 6.4 Hz, 2H).

Example 43: (6-Hydroxy-8-oxo-3-phenyl-2',3',5',6'-tetrahydro-8H-spiro[indolizin-5,4'-pyran]-7-carbonyl)glycine (43)

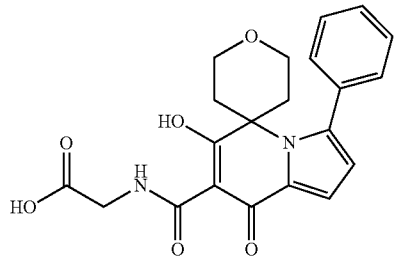

Step 1: 4-(2-phenyl-1H-pyrrol-1-yl)tetrahydro-2H-pyran-4-carboxylic Acid (43a)

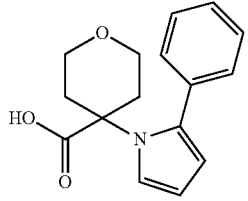

The synthetic route of the first step for compound 24a of Example 24 was repeated, wherein the starting material 1-amino-cyclopentane-1-carboxylic acid was replaced by 4-aminotetrahydro-2H-pyran-4-carboxylic acid to afford compound 43a. LCMS ESI(+): 272 (M+1)$^+$.

Step 2: dimethyl 2-(4-(2-phenyl-1H-pyrrol-1-yl)tetrahydro-2H-pyran-4-carbonyl) malonate (43b)

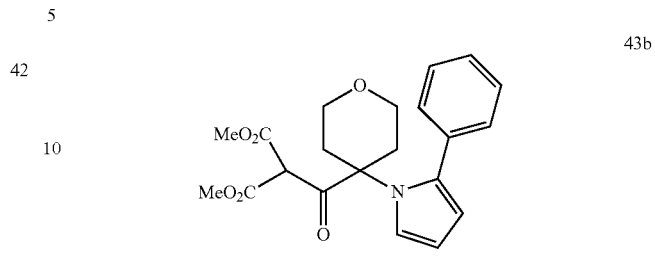

The synthetic route of the second step for compound 15b of Example 15 was repeated, wherein the starting material 15a was replaced with 43a to afford compound 43b. LCMS ESI(+): 386 (M+1)$^+$.

Step 3: Methyl 6-Hydroxy-8-oxo-3-phenyl-2',3',5',6'-tetrahydro-8H-spiro[indolizin-5,4'-pyran]-7-carboxylate (43c)

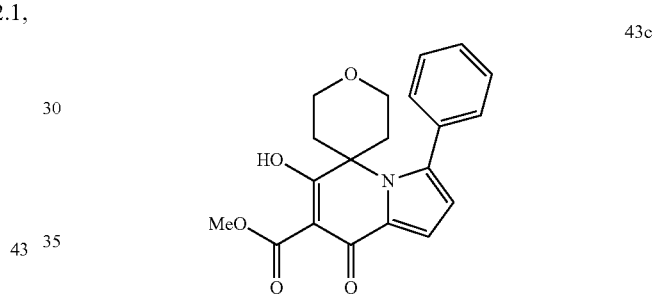

The synthetic route of the third step for compound 15c of Example 15 was repeated, wherein the starting material 15b was replaced with 43b to afford compound 43c. LCMS ESI(+): 354 (M+1)$^+$.

Step 4: (6-Hydroxy-8-oxo-3-phenyl-2',3',5',6'-tetrahydro-8H-spiro[indolizin-5,4'-pyran]-7-carbonyl)glycine (43)

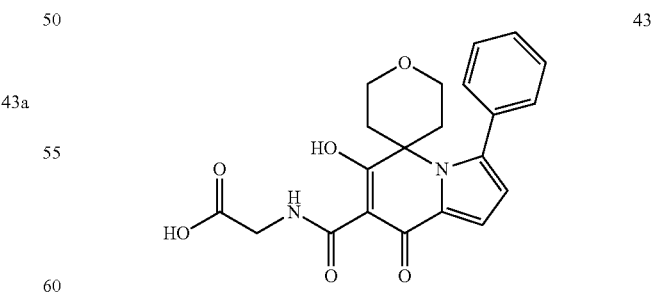

The synthetic route of the fourth step for compound 15 of Example 15 was repeated, wherein the starting material 15c was replaced with 43c to afford compound 43. LCMS ESI(+): 397 (M+1)$^+$. $^1$H NMR (500 MHz, DMSO-d$_6$) δ 17.88 (s, 1H), 12.95 (s, 1H), 9.74 (t, J=5.4 Hz, 1H), 7.49 (s, 5H), 7.13 (d, J=4.0 Hz, 1H), 6.36 (d, J=4.0 Hz, 1H), 4.08 (d,

Example 44: (6'-Hydroxy-8'-oxo-3'-phenyl-8'H-spiro[cyclopentane-1,5'-indolizine]-7'-carbonyl)-D-alanine (44)

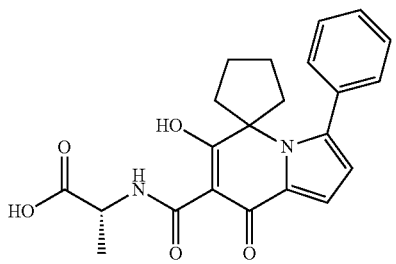

Step 1: (6'-Hydroxy-8'-oxo-3'-phenyl-8'H-spiro[cyclopentane-1,5'-indolizine]-7'-carbonyl)-D-alanine (44)

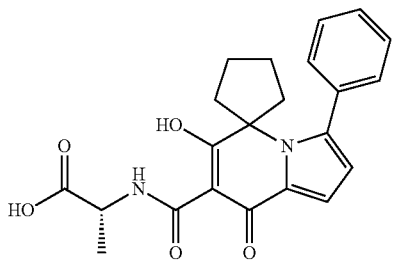

The synthetic route of the first step for compound 24 of Example 24 was repeated, wherein the starting material glycine was replaced with D-alanine to afford compound 44. LCMS ESI(+): 395 (M+1)$^+$. $^1$H NMR (500 MHz, dmso-d6) δ (ppm): 17.85 (br s, 1H), 13.11 (s, 1H), 9.99 (s, 1H), 7.49 (m, J=8.4, 6.2, 3.2 Hz, 5H), 7.07 (d, J=3.8 Hz, 1H), 6.35 (d, J=3.8 Hz, 1H), 4.47 (q, J=7.1 Hz, 1H), 2.29 (br s, 2H), 2.14 (br s, 2H), 1.53 (s, 2H), 1.43 (d, J=7.2 Hz, 3H), 0.91 (m, 2H).

Example 45: (6-Hydroxy-8-oxo-2',3',5',6'-tetrahydro-8H-spiro[indolizin-5,4'-pyran]-7-carbonyl)glycine (45)

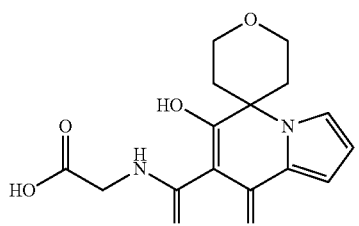

Step 1: 4-(1H-pyrrol-1-yl)tetrahydro-2H-pyran-4-carboxylic Acid (45a)

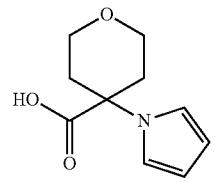

The synthetic route of the first step of Example 6 was repeated, wherein the starting material 1-aminocyclobutane-1-carboxylic acid was replaced with 4-aminotetrahydro-2H-pyran-4-carboxylic acid to afford compound 45a. LCMS ESI(+): 196 (M+1)$^+$.

Step 2: Dimethyl 2-(4-(1H-pyrrol-1-yl)tetrahydro-2H-pyran-4-carbonyl) malonate (45b)

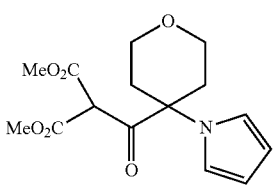

The synthetic route of the second step of Example 8 was repeated, wherein the starting materials diethyl malonate and 8a were replaced with dimethyl malonate and 45a to afford compound 45b. $^1$H NMR (500 MHz, dmso-d6) δ (ppm): 6.98 (t, J=2.2 Hz, 2H), 6.18 (t, J=2.2 Hz, 2H), 4.71 (s, 1H), 3.75 (dt, J=11.8, 4.2 Hz, 2H), 3.42-3.38 (m, 2H), 2.40-2.34 (m, 2H), 2.22 (ddd, J=14.1, 9.6, 4.0 Hz, 2H). LCMS ESI(+): 319 (M+1)$^+$.

Step 3: Methyl 6-Hydroxy-8-oxo-2',3',5',6'-tetrahydro-8H-spiro[indolizin-5,4'-pyran]-7-carboxylate (45c)

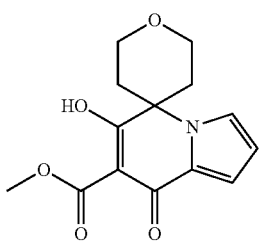

The synthetic route of the third step of Example 8 was repeated, wherein the starting material 8b was replaced with 45b to afford compound 45c. LCMS ESI(+): 278 (M+1)$^+$.

(J=5.6 Hz, 2H), 3.83 (td, J=11.8, 2.5 Hz, 2H), 3.57 (dd, J=11.3, 5.7 Hz, 2H), 2.33 (td, J=13.1, 5.9 Hz, 2H), 1.88 (d, J=13.7 Hz, 2H).

Step 4: (6-Hydroxy-8-oxo-2',3',5',6'-tetrahydro-8H-spiro[indolizin-5,4'-pyran]-7-carbonyl)glycine (45)

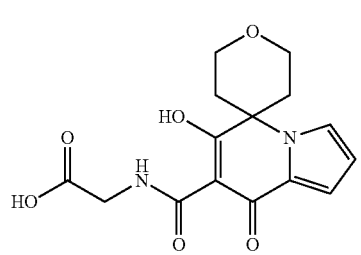

The synthetic route of the fourth step of Example 6 was repeated, wherein the starting material 6c was replaced with 45c to afford compound 45. $^1$H NMR (500 MHz, dmso-d6) δ (ppm): 18.14 (s, 1H), 12.97 (s, 1H), 9.89 (s, 1H), 7.84 (s, 1H), 7.07-6.97 (m, 1H), 6.51 (t, J=3.3 Hz, 1H), 4.13-4.00 (m, 4H), 3.87 (ddd, J=12.0, 5.2, 2.5 Hz, 2H), 2.17-2.01 (m, 4H). LCMS ESI(+): 321 (M+1)$^+$.

Example 46: (6'-Hydroxy-8'-oxo-8'H-spiro[cyclohexane-1,5'-indolizine]-7'-carbonyl)glycine ethyl ester (46)

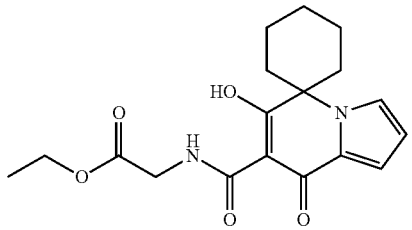

Step 1: (6'-Hydroxy-8'-oxo-8'H-spiro[cyclohexane-1,5'-indolizine]-7'-carbonyl)glycine ethyl ester (46)

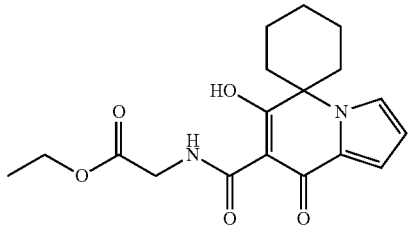

The synthetic route of the first step of Example 10 was repeated, wherein the starting material 8 was replaced with 13 to afford compound 46. LCMS ESI(+): 347 (M+1)$^+$. $^1$H NMR (500 MHz, dmso-d6) δ (ppm): 17.90 (s, 1H), 9.93 (t, J=5.7 Hz, 1H), 7.82 (s, 1H), 6.99 (dd, J=1.5, 4.2 Hz, 1H), 6.51-6.46 (m, 1H), 4.19-4.10 (m, 4H), 2.05-1.83 (m, 6H), 1.74-1.61 (m, 3H), 1.55-1.43 (m, 1H), 1.21 (t, J=7.1 Hz, 3H).

Example 47: (3'-(4-Fluorophenyl)-6'-hydroxy-8'-oxo-8'H-spiro[cyclopentane-1,5'-indolizine]-7'-carbonyl)glycine Ethyl ester (47)

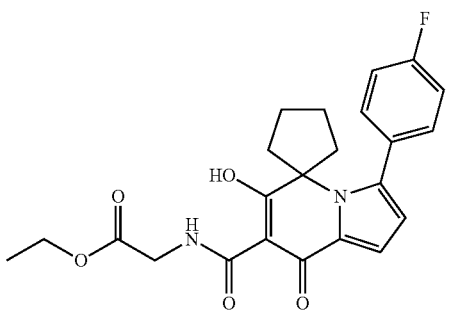

Step 1: (3'-(4-Fluorophenyl)-6'-hydroxy-8'-oxo-8'H-spiro[cyclopentane-1,5'-indolizine]-7'-carbonyl)glycine Ethyl ester (47)

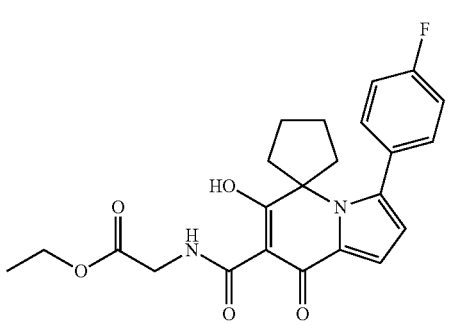

The synthetic route of the first step of Example 46 was repeated, wherein the starting material 13 was replaced with 25 to afford compound 47. LCMS ESI(+): 427 (M+1)$^+$. $^1$H NMR (500 MHz, dmso-d6) δ (ppm): 17.82 (s, 1H), 9.88 (s, 1H), 7.63-7.54 (m, 2H), 7.35-7.28 (m, 2H), 7.07 (d, J=4.0 Hz, 1H), 6.37 (d, J=4.1 Hz, 1H), 4.20-4.08 (m, 4H), 2.34-2.23 (m, 2H), 2.16-2.05 (m, 2H), 1.63-1.49 (m, 2H), 1.21 (t, J=7.1 Hz, 3H), 1.02-0.90 (m, 2H).

Example 48: (6'-Hydroxy-8'-oxo-3'-phenyl-8'H-spiro[cyclohexane-1,5'-indolizine]-7'-carbonyl)glycine-2,2-dideuterium (48)

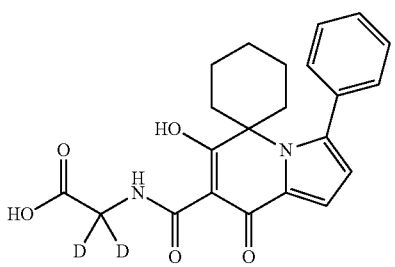

Step 1: (6'-Hydroxy-8'-oxo-3'-phenyl-8'H-spiro[cyclohexane-1,5'-indolizine]-7'-carbonyl)glycine-2,2-dideuterium (48)

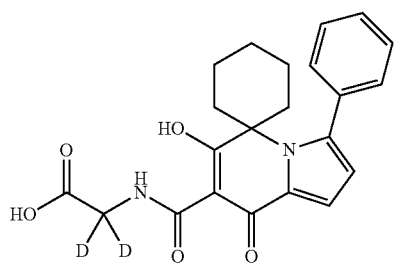

The synthetic route of the fourth step of Example 35 was repeated, wherein the starting material glycine was replaced with glycine-2,2-dideuterium to afford compound 48. LCMS ESI(+): 397 (M+1)⁺. ¹H NMR (500 MHz, DMSO-d6) δ (ppm): 12.9 (1H, s), 9.8 (1H, t, NH), 7.5-7.4 (5H, m), 7.09 (1H, d), 6.34-6.33 (1H, d), 2.14-1.79 (10H, m).

Example 49: (6'-Hydroxy-8'-oxo-3'-(phenyl-4-deuterium)-8'H-spiro[cyclohexane-1,5'-indolizine]-7'-carbonyl) glycine (49)

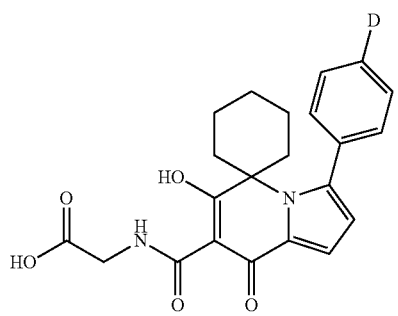

Step 1: (6'-Hydroxy-8'-oxo-3'-(phenyl-4-deuterium)-8'H-spiro[cyclohexane-1,5'-indolizine]-7'-carbonyl) glycine (49)

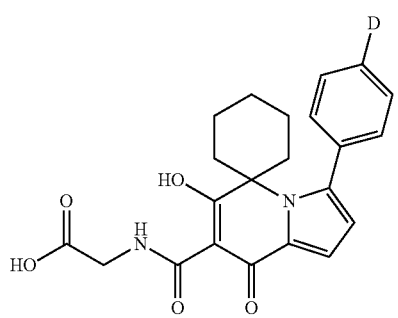

For the synthesis of compound 49, reference can be made to the literature (Org. Lett. 2004, vol 6, 3521): A 100 ml round bottom flask filled with atmospheric pressure of hydrogen was charged with a mixture of heavy water (3 ml) and 10% palladium on carbon (7.4 mg). The mixture was stirred at RT for 24 hours to which a solution of compound 36 (0.5 mmol) and triethylamine (0.6 mmol) in tetrahydrofuran (5 mL) was then added. The reaction was stirred at RT for further 24 hours. The reaction mixture was diluted with ethyl acetate and water, acidified with 2 mol/L of hydrochloric acid. The ethyl acetate phase was separated; washed twice with diluted aqueous sodium chloride solution, dried over anhydrous sodium sulfate, filtered and concentrated. The residue was purified by column chromatography to afford Compound 49. LCMS ESI(+): 396 (M+1)⁺.

Example 50: (3'-(4-Chlorophenyl)-6'-hydroxy-8'-oxo-8'H-spiro[cyclopentane-1,5'-indolizine]-7'-carbonyl) glycine methyl ester (50)

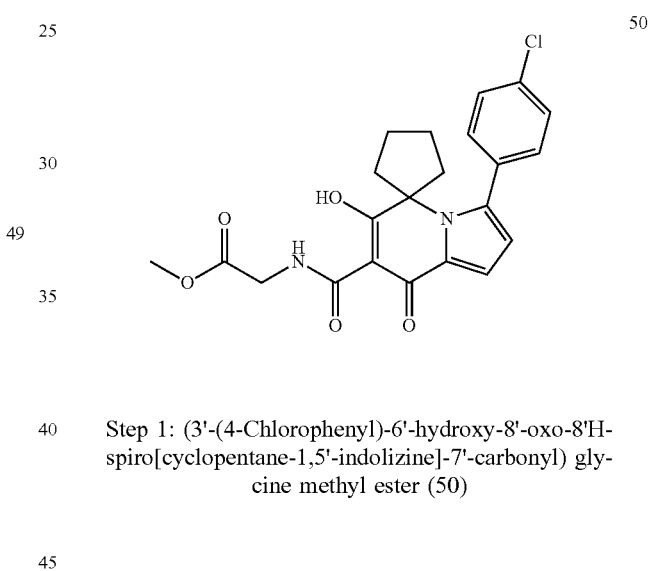

Step 1: (3'-(4-Chlorophenyl)-6'-hydroxy-8'-oxo-8'H-spiro[cyclopentane-1,5'-indolizine]-7'-carbonyl) glycine methyl ester (50)

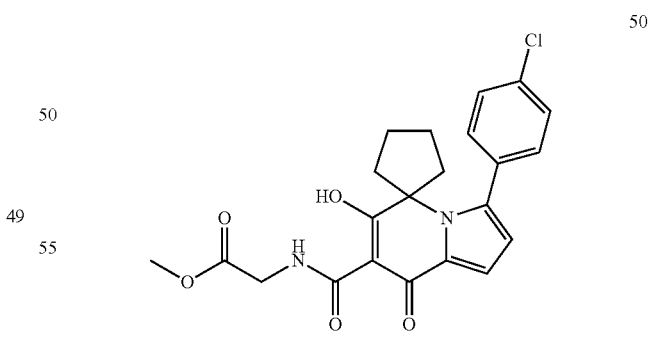

Compound 26 (50 mg) was suspended in MeOH (2 mL) to which thionyl chloride (0.2 ml) was added carefully dropwise. The reaction was allowed to continue with refluxing until the reaction was complete. It was cooled to RT naturally and then cooled with an ice water bath. The solid was collected by filtration and washed with cold methanol to give Compound 50. LCMS ESI(+): 429 (M+1)⁺.

Example 51: (3'-(4-Fluorophenyl)-6'-hydroxy-8'-oxo-8'H-spiro[cyclopentane-1,5'-indolizine]-7'-carbonyl) glycine methyl ester (51)

Examples 52 and 53: (1'-Cyclopropyl-6'-hydroxy-8'-oxo-8'H-spiro[cyclohexane-1,5'-indolizine]-7'-carbonyl)glycine (52) and (2'-Cyclopropyl-6'-hydroxy-8'-oxo-8'H-spiro[cyclohexane-1,5'-indolizine]-7'-carbonyl)glycine (53)

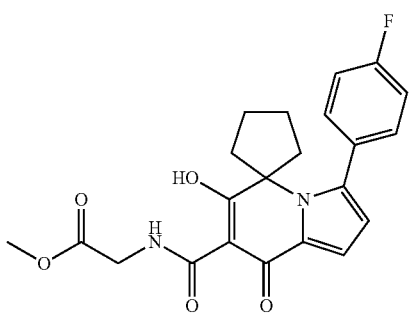

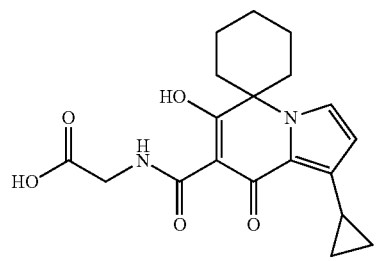

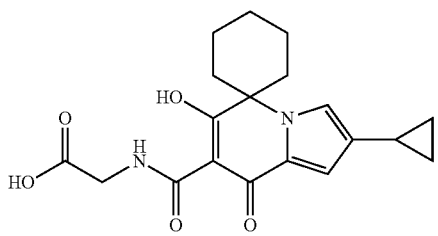

Step 1: (3'-(4-Fluorophenyl)-6'-hydroxy-8'-oxo-8'H-spiro[cyclopentane-1,5'-indolizine]-7'-carbonyl) glycine methyl ester (51)

Step 1: 1-(3-bromo-1H-pyrrole-1-yl)cyclohexane-1-carboxylic acid (52-Br)

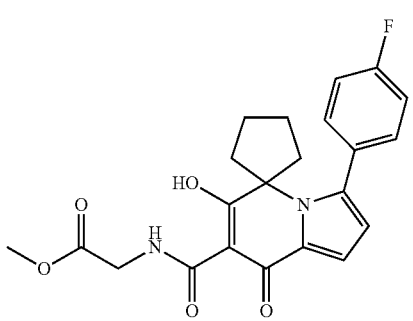

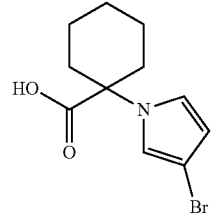

Compound 25 (50 mg) was suspended in MeOH (2 mL) to which thionyl chloride (0.2 ml) was added carefully dropwise. The reaction was allowed to continue with refluxing until the reaction was complete. It was cooled to RT naturally and then cooled with an ice water bath. The solid was collected by filtration and washed with cold methanol to give Compound 51. LCMS ESI(+): 413 (M+1)$^+$. $^1$H NMR (500 MHz, DMSO-d6) δ 17.78 (s, 1H), 9.88 (t, J=5.7 Hz, 1H), 7.63-7.55 (m, 2H), 7.34-7.28 (m, 2H), 7.08 (d, J=4.0 Hz, 1H), 6.37 (d, J=4.0 Hz, 1H), 4.16 (d, J=5.8 Hz, 2H), 3.68 (s, 3H), 2.35-2.27 (m, 2H), 2.16-2.06 (m, 2H), 1.60-1.52 (m, 2H), 1.01-0.92 (m, 2H).

Compound 52-Br was prepared according to the procedure similar to those in the literature of Synlett, 2002, (7), 1152-1154: Compound 13a (1 eq.) was dissolved in tetrahydrofuran (5 vol.) and cooled to −78° C. with dry ice acetone bath to which phosphorus tribromide (0.05 eq.) was added. With stirring, ground solid N-bromosuccinimide (1.15 eq.) was added and the resulting mixture was stirred at −78° C. for 2 hr then stirred at RT overnight. The reaction solution was diluted with water and extracted with ethyl acetate. The ethyl acetate layer was separated, and then washed twice with diluted aqueous sodium chloride solution. The ethyl acetate phase was dried over anhydrous sodium sulfate and spin-dried on an evaporator. The residue was purified by column chromatography to afford product 52-Br. LCMS ESI(+): 272 (M+1)$^+$.

Step 2: 1-(3-cyclopropyl-1H-pyrrol-1-yl)cyclohexane-1-carboxylic acid (52a)

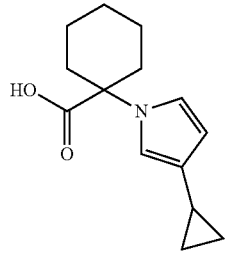

52a

Compound 52a was prepared by Suzuki coupling reaction: compound 52-Br (1 eq.), cyclopropylborate (1.5 eq.), Pd(OAc)$_2$ (0.05 eq.), 2',6'-methoxybiphenyl-dicyclohexyl phosphine (CAS #: 657408-07-6, 0.1 eq.) and potassium phosphate (3 eq.) were mixed in toluene (10 vol.) and refluxed overnight under nitrogen. After cooling, the reaction solution was diluted with water, acidified with diluted aqueous hydrochloric acid, and extracted with ethyl acetate. The ethyl acetate layer was separated, washed twice with dilute aqueous sodium chloride, dried over anhydrous sodium sulfate, and filtered to remove the desiccant and then dried on a rotary evaporator. The residue was purified by column chromatography to afford product 52a. LCMS ESI (+): 234 (M+1)$^+$. $^1$H NMR (500 MHz, dmso-d6) δ (ppm): 12.80 (1H, br s), 6.73 (1H, t), 6.67 (1H, t), 5.75-5.74 (1H, m), 2.24-2.10 (3H, m), 1.67-1.62 (1H, m), 1.48-1.44 (7H, m), 0.73-0.69 (2H, dd), 0.41-0.38 (2H, dd).

Step 3: Dimethyl 2-(1-(3-cyclopropyl-1H-pyrrol-1-yl)cyclohexane-1-carbonyl)malonate (52b)

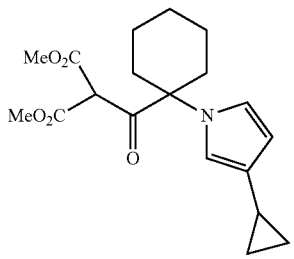

52b

The synthetic route of the second step for compound 15b of Example 15 was repeated, wherein the starting material 15a was replaced with 52a to afford compound 52b. LCMS ESI(+): 348 (M+1)$^+$. $^1$H NMR (500 MHz, dmso-d6) δ (ppm): 6.77 (1H, t), 6.67 (1H, t), 4.57 (1H, s), 3.63 (6H, s), 2.32-2.29 (2H, m), 1.92-1.86 (2H, m), 1.67-1.65 (1H, m), 1.61-1.58 (2H, m), 1.48-1.47 (2H, m), 0.75-0.73 (2H, dd), 0.44-0.43 (2H, dd).

Step 4: Methyl 1'-Cyclopropyl-6'-hydroxy-8'-oxo-8'H-spiro[cyclohexane-1,5'-indolizine]-7'-carboxylate (52c1) and Methyl 2'-Cyclopropyl-6'-hydroxy-8'-oxo-8'H-spiro[cyclohexane-1,5'-indolizine]-7'-carboxylate (52c2)

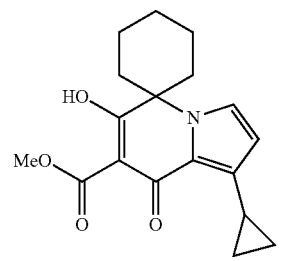

52c1

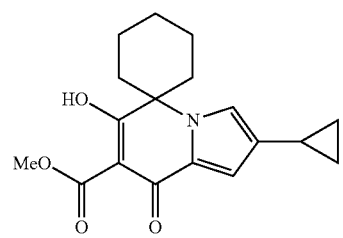

52c2

Compounds 52c1 and 52c2 were obtained via purification by column chromatography of two isomers obtained by cyclization of 52b as a starting material with methanesulfonic acid, under the conditions similar to those for the preparation of compound 1c. 52c1: LCMS ESI(+): 316 (M+1)$^+$; $^1$H NMR (500 MHz, dmso-d6) δ (ppm): 14.48 (1H, s), 7.66 (1H, d), 6.03 (1H, d), 3.81 (3H, s), 2.02-1.96 (8H, m), 1.62-1.60 (3H, m), 0.98-0.97 (2H, dd), 0.66-0.65 (2H, dd). 52c2: LCMS ESI(+): 316 (M+1)$^+$.

Step 5: (1'-Cyclopropyl-6'-hydroxy-8'-oxo-8'H-spiro[cyclohexane-1,5'-indolizine]-7'-carbonyl)glycine (52)

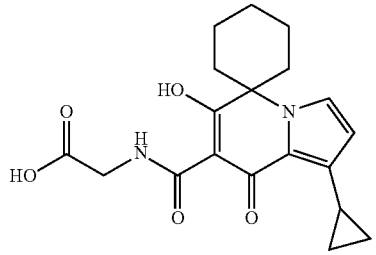

52

The synthetic route of the fourth step for compound 15 of Example 15 was repeated, wherein the starting material 15c was replaced with 52c1 to afford compound 52. LCMS ESI(+): 359 (M+1)$^+$. $^1$H NMR (500 MHz, dmso-d6) δ (ppm): 18.40 (1H, s), 12.96 (1H, s), 10.04 (1H, d), 7.66 (1H, d), 6.03 (1H, d), 4.07 (2H, d), 2.01-1.96 (5H, m), 1.86-1.85 (2H, m), 1.65-1.64 (2H, m), 1.47-1.45 (2H, m), 0.96-0.95 (2H, dd), 0.65-0.64 (2H, dd).

Step 6: (2'-Cyclopropyl-6'-hydroxy-8'-oxo-8'H-spiro[cyclohexane-1,5'-indolizine]-7'-carbonyl)glycine (53)

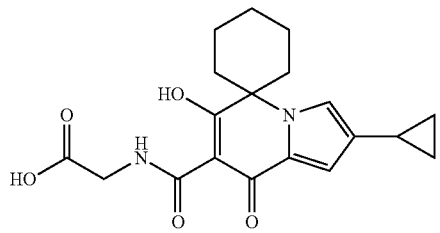

The synthetic route of the fourth step for compound 15 of Example 15 was repeated, wherein the starting material 15c was replaced with 52c2 to afford compound 53. LCMS ESI(+): 359 (M+1)$^+$.

Examples 54 and 55: (6'-Hydroxy-8'-oxo-1'-phenyl-8'H-spiro[cyclohexane-1,5'-indolizine]-7'-carbonyl)glycine (54) and (6'-Hydroxy-8'-oxo-2'-phenyl-8'H-spiro[cyclohexane-1,5'-indolizine]-7'-carbonyl)glycine (55)

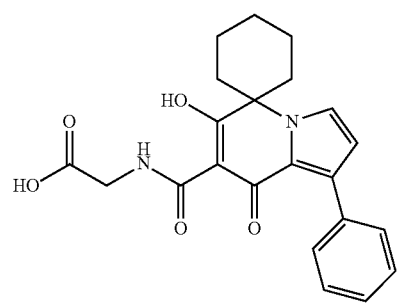

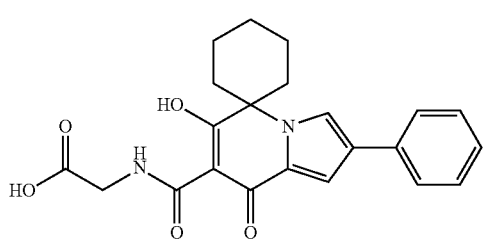

Step 1: 1-(3-phenyl-1H-pyrrol-1-yl)cyclohexane-1-carboxylic acid (54a)

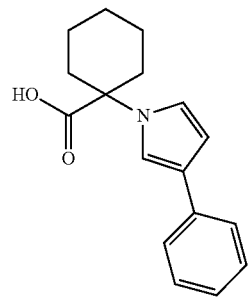

The synthetic route of the second step for compound 52a of Examples 52 and 53 was repeated, wherein the starting material cyclopropylborate was replaced with phenylborate to afford compound 54a. LCMS ESI(+): 270 (M+1)$^+$. $^1$H NMR (500 MHz, dmso-d6) δ (ppm): 12.67 (1H, s), 7.53-7.56 (2H, m), 7.39 (1H, t, J=2.0 Hz), 7.29 (2H, t, J=8.0 Hz), 7.10 (1H, t, J=8.0 Hz), 6.95 (2H, t, J=3.0 Hz), 6.47 (1H, dd, J=1.6 Hz) 2.25-2.35 (2H, m), 2.10-2.17 (2H, m), 1.43-1.55 (6H, m).

Step 2: Dimethyl 2-(1-(3-phenyl-1H-pyrrol-1-yl)cyclohexane-1-carbonyl)malonate (54b)

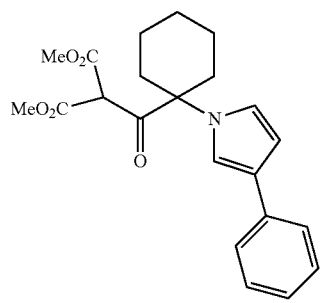

The synthetic route of the second step for compound 15b of Example 15 was repeated, wherein the starting material 15a was replaced with 54a to afford compound 54b. LCMS ESI(+): 384 (M+1)$^+$. $^1$H NMR (500 MHz, dmso-d6) δ (ppm): 7.58-7.56 (2H, m), 7.33-7.30 (2H, m), 7.27-7.25 (1H, m), 7.15-7.11 (1H, m), 7.00-6.99 (1H, s), 6.58-6.57 (1H, m), 4.85 (1H, s), 3.52 (6H, s), 2.46-2.43 (2H, m), 1.99-1.95 (2H, m), 1.64-1.62 (2H, m), 1.52-1.49 (2H, m), 1.42-1.30 (2H, m).

Step 3: Methyl 6'-Hydroxy-8'-oxy-1'-phenyl-8'H-spiro[cyclohexane-1,5'-indolizine]-7'-carboxylate (54c1), and Methyl 6'-Hydroxy-8'-oxy-2'-phenyl-8'H-spiro[cyclohexane-1,5'-indolizine]-7'-carboxylate (54c2)

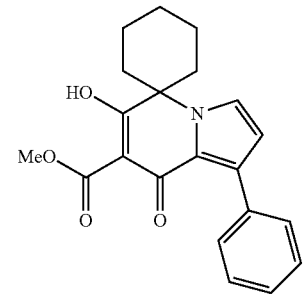

54c1

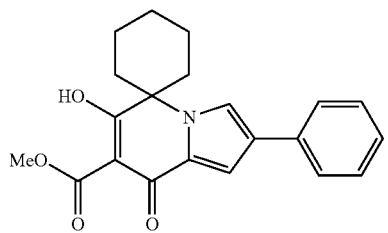

54c2

Compounds 54c1 and 54c2 were obtained via purification by column chromatography of two isomers obtained by cyclization of 54b as a starting material with methanesulfonic acid, under the conditions similar to those for the preparation of compound 1c. 54c1: LCMS ESI(+): 352 (M+1)$^+$; $^1$H NMR (500 MHz, dmso-d6) δ (ppm): 14.24 (1H, s) 7.83 (1H, s), 7.52-7.50 (2H, m), 7.37 (2H, t), 7.33-7.31 (1H, m), 6.50 (1H, d), 3.80 (3H, s), 2.10-1.95 (2H, m), 1.89-1.83 (4H, m), 1.69-1.64 (2H, m), 1.48-1.40 (2H, m). 54c2: LCMS ESI(+): 352 (M+1)$^+$.

Step 4: (6'-Hydroxy-8'-oxo-1'-phenyl-8'H-spiro[cyclohexane-1,5'-indolizine]-7'-carbonyl)glycine (54)

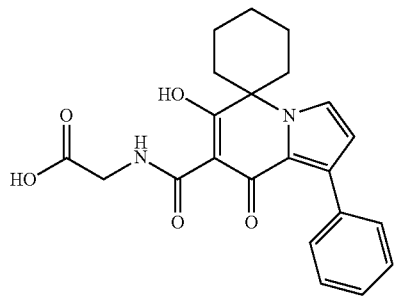

54

The synthetic route of the fourth step for compound 15 of Example 15 was repeated, wherein the starting material 15c was replaced with 54c1 to afford compound 54. LCMS ESI(+): 395 (M+1)$^+$. $^1$H NMR (500 MHz, dmso-d6) δ (ppm): 18.30 (1H, s), 12.97 (1H, s), 10.07 (1H, s), 7.83 (1H, s), 7.53-7.52 (2H, m), 7.36 (2H, t), 7.33-7.31 (1H, m), 6.53 (1H, br s), 4.06 (2H, d), 2.12-2.07 (2H, m), 2.01-1.93 (4H, m), 1.69-1.64 (2H, m), 1.48-1.40 (2H, m).

Step 5: (6'-Hydroxy-8'-oxo-2'-phenyl-8'H-spiro[cyclohexane-1,5'-indolizine]-7'-carbonyl)glycine (55)

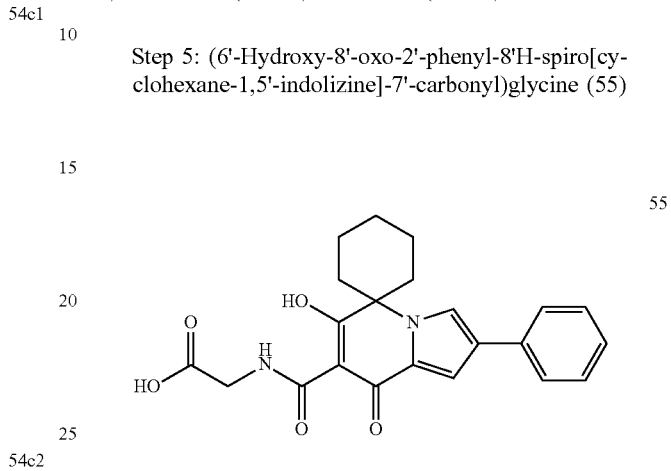

55

The synthetic route of the fourth step for compound 15 of Example 15 was repeated, wherein the starting material 15c was replaced with 54c2 to afford compound 55. LCMS ESI(+): 395 (M+1)$^+$.

Examples 56 and 57: (1'-(4-Fluorophenyl)-6'-hydroxy-8'-oxo-8'H-spiro[cyclohexane-1,5'-indolizine]-7'-carbonyl) glycine (56) and (2'-(4-Fluorophenyl)-6'-hydroxy-8'-oxo-8'H-spiro[cyclohexane-1,5'-indolizine]-7'-carbonyl) glycine (57)

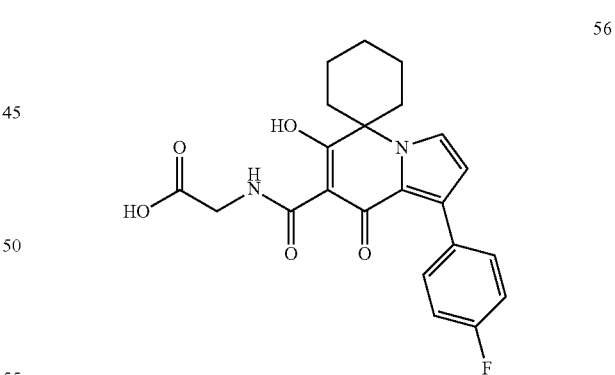

56

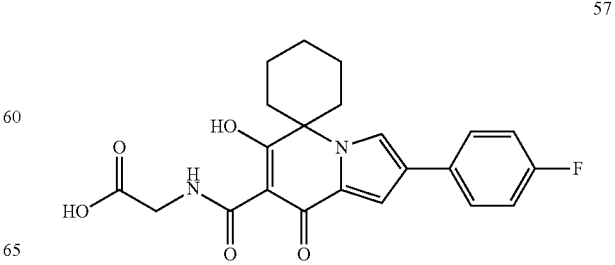

57

Step 1: 1-(3-(4-Fluorophenyl)-1H-pyrrol-1-yl)cyclohexane-1-carboxylic Acid (56a)

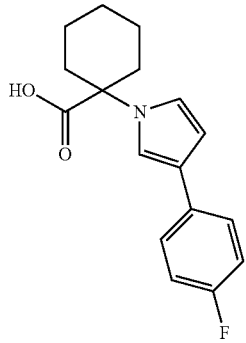

56a

The synthetic route of the second step for compound 52a of Examples 52 and 53 was repeated, wherein the starting material cyclopropylborate was replaced with 4-fluorophenylborate to afford compound 56a. LCMS ESI(+): 288 (M+1)$^+$.

Step 2: Dimethyl 2-(1-(3-(4-fluorophenyl)-1H-pyrrol-1-yl)cyclohexane-1-carbonyl)malonate (56b)

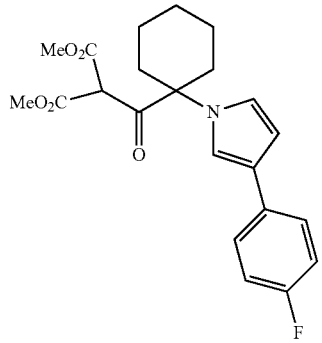

56b

The synthetic route of the second step for compound 15b of Example 15 was repeated, wherein the starting material 15a was replaced with 56a to afford compound 56b. LCMS ESI(+): 402 (M+1)$^+$.

Step 3: Methyl 1'-(4-Fluorophenyl)-6'-hydroxy-8'-oxo-8'H-spiro[methyl hexane-1,5'-indolizine]-7'-carboxylate (56c1) and Methyl 2'-(4-Fluorophenyl)-6'-hydroxy-8'-oxo-8'H-spiro[methyl hexane-1,5'-indolizine]-7'-carboxylate (56c2)

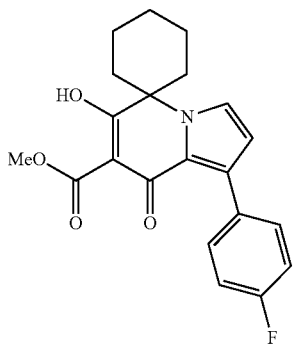

56c1

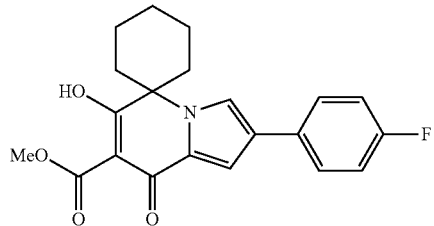

56c2

Compounds 56c1 and 56c2 were obtained via purification by column chromatography of two isomers obtained by cyclization of 56b as a starting material with methanesulfonic acid, under the conditions similar to those for the preparation of compound 1c. 56c1: LCMS ESI(+): 370 (M+1)$^+$; 56c2: LCMS ESI(+): 370 (M+1)$^+$.

Step 4: (1'-(4-Fluorophenyl)-6'-hydroxy-8'-oxo-8'H-spiro[cyclohexane-1,5'-indolizine]-7'-carbonyl) glycine (56)

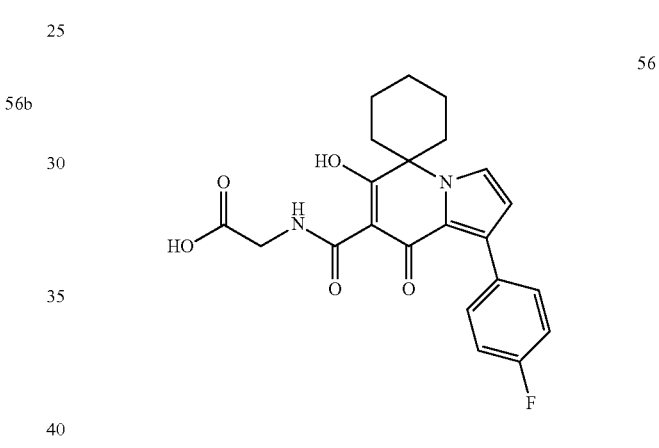

56

The synthetic route of the fourth step for compound 15 of Example 15 was repeated, wherein the starting material 15c was replaced with 56c1 to afford compound 56. LCMS ESI(+): 413 (M+1)$^+$.

Step 5: (2'-(4-Fluorophenyl)-6'-hydroxy-8'-oxo-8'H-spiro[cyclohexane-1,5'-indolizine]-7'-carbonyl) glycine (57)

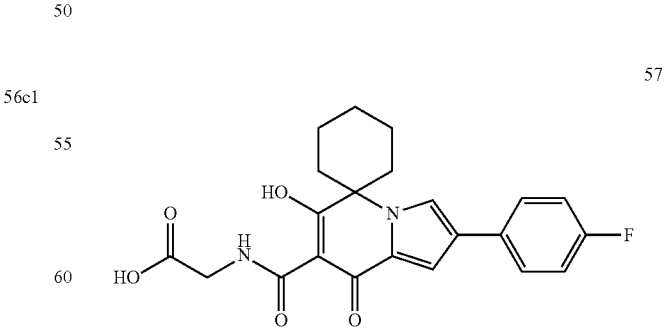

57

The synthetic route of the fourth step for compound 15 of Example 15 was repeated, wherein the starting material 15c was replaced with 56c2 to afford compound 57. LCMS ESI(+): 413 (M+1)$^+$.

Examples 58 and 59: (1'-(4-Chlorophenyl)-6'-hydroxy-8'-oxo-8'H-spiro[cyclohexane-1,5'-indolizine]-7'-carbonyl) glycine (58) and (2'-(4-Chlorophenyl)-6'-hydroxy-8'-oxo-8'H-spiro[cyclohexane-1,5'-indolizine]-7'-carbonyl) glycine (59)

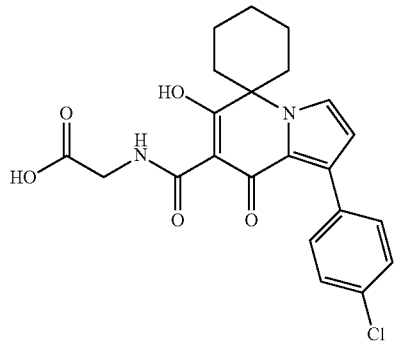

58

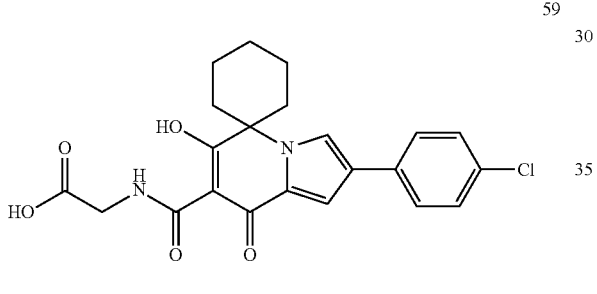

59

Step 1: 1-(3-(4-Chlorophenyl)-1H-pyrrol-1-yl)cyclohexane-1-carboxylic Acid (58a)

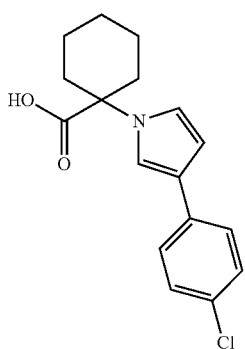

58a

The synthetic route of the second step for compound 52a of Examples 52 and 53 was repeated, wherein the starting material cyclopropylborate was replaced with 4-chlorophenylborate to afford compound 58a. LCMS ESI(+): 304 (M+1)$^+$.

Step 2: Dimethyl 2-(1-(3-(4-chlorophenyl)-1H-pyrrol-1-yl)cyclohexane-1-carbonyl)malonate (58b)

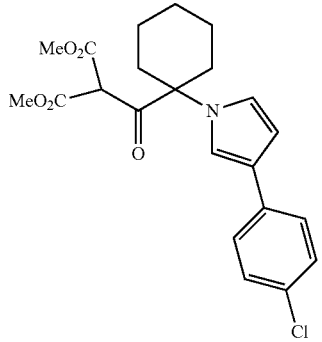

58b

The synthetic route of the second step for compound 15b of Example 15 was repeated, wherein the starting material 15a was replaced with 58a to afford compound 58b. LCMS ESI(+): 418 (M+1)$^+$.

Step 3: Methyl 1'-(4-Chlorophenyl)-6'-hydroxy-8'-oxo-8'H-spiro[methyl hexane-1,5'-indolizine]-7'-carboxylate (58c1) and Methyl 2'-(4-chlorophenyl)-6'-hydroxy-8'-oxo-8'H-spiro[cyclohexane-1,5'-indolizine]-7'-carboxylate (58c2)

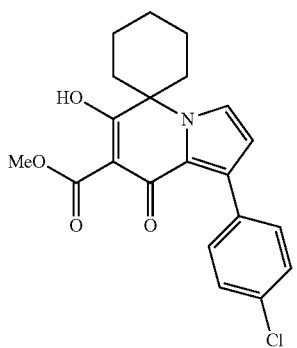

58c1

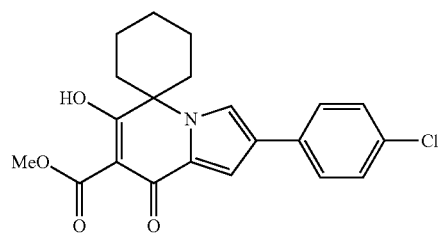

58c2

Compounds 58c1 and 58c2 were obtained via purification by column chromatography of two isomers obtained by cyclization of 58b as a starting material with methanesulfonic acid, under the conditions similar to those for the preparation of compound 1c. 58c1: LCMS ESI(+): 386 (M+1)$^+$; 58c2: LCMS ESI(+): 386 (M+1)$^+$.

Step 4: (1'-(4-Chlorophenyl)-6'-hydroxy-8'-oxo-8'H-spiro[cyclohexane-1,5'-indolizine]-7'-carbonyl) glycine (58)

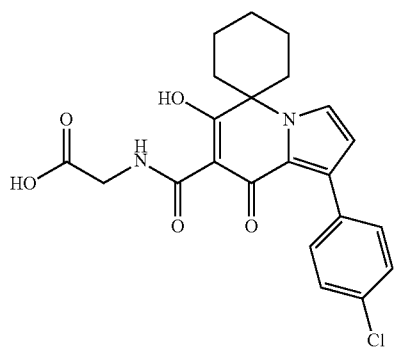

58

The synthetic route of the fourth step for compound 15 of Example 15 was repeated, wherein the starting material 15c was replaced with 58c1 to afford compound 58. LCMS ESI(+): 429 (M+1)⁺.

Step 5: (2'-(4-Chlorophenyl)-6'-hydroxy-8'-oxo-8'H-spiro[cyclohexane-1,5'-indolizine]-7'-carbonyl) glycine (59)

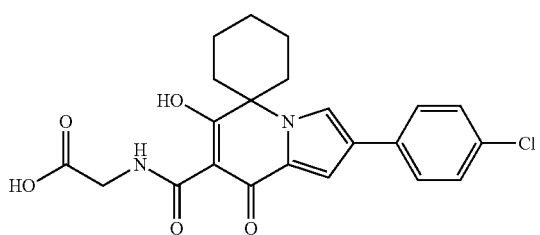

59

The synthetic route of the fourth step for compound 15 of Example 15 was repeated, wherein the starting material 15c was replaced with 58c2 to afford compound 59. LCMS ESI(+): 429 (M+1)⁺.

Examples 60 and 61: (6'-Hydroxy-1'-(4-methoxyphenyl)-8'-oxo-8'H-spiro[cyclohexane-1,5'-indolizine]-7'-carbonyl glycine (60) and (6'-hydroxy-2'-(4-methoxyphenyl)-8'-oxo-8'H-spiro[cyclohexane-1,5'-indolizine]-7'-carbonyl)glycine (61)

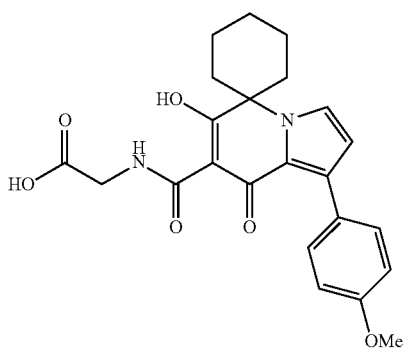

60

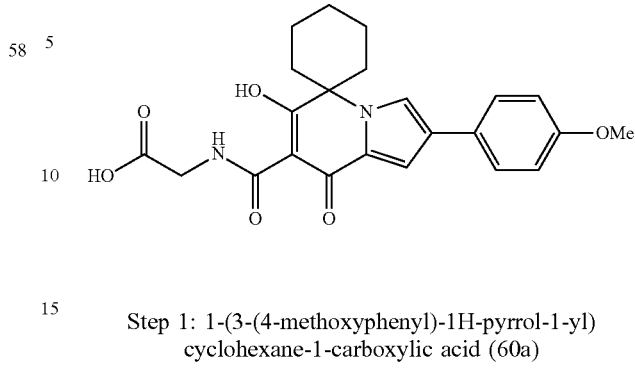

61

Step 1: 1-(3-(4-methoxyphenyl)-1H-pyrrol-1-yl)cyclohexane-1-carboxylic acid (60a)

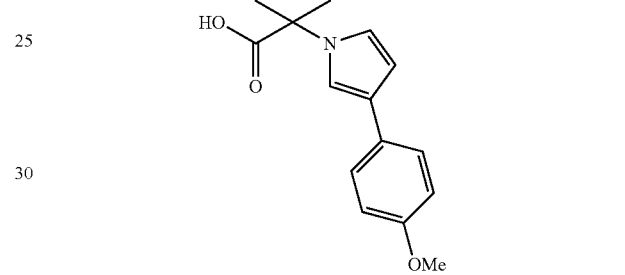

60a

The synthetic route of the second step for compound 52a of Examples 52 and 53 was repeated, wherein the starting material cyclopropylborate was replaced with 4-methoxyphenylborate to afford compound 60a. LCMS ESI(+): 300 (M+1)⁺.

Step 2: Dimethyl 2-(1-(3-(4-methoxyphenyl)-1H-pyrrol-1-yl)cyclohexane-1-carbonyl]malonate (60b)

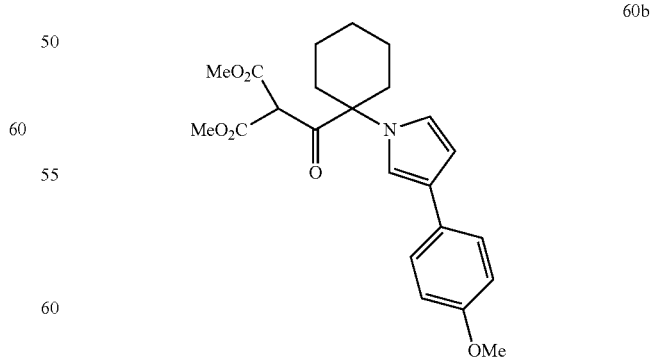

60b

The synthetic route of the second step for compound 15b of Example 15 was repeated, wherein the starting material 15a was replaced with 60a to afford compound 60b.

Step 3: Methyl 1'-(4-Methoxyphenyl)-6'-hydroxy-8'-oxo-8'H-spiro[cyclohexane-1,5'-indolizine]-7'-carboxylate (60c1) and Methyl 2'-(4-methoxyphenyl)-6'-hydroxy-8'-oxo-8'H-spiro[cyclohexane-1,5'-indolizine]-7'-carboxylate (60c2)

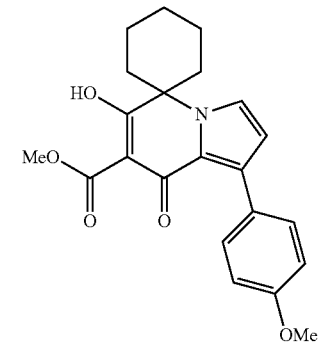

60c1

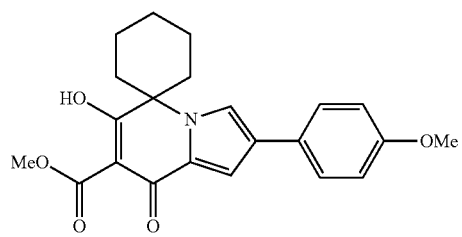

60c2

Compounds 60c1 and 60c2 were obtained via purification by column chromatography of two isomers obtained by cyclization of 60b as a starting material with methanesulfonic acid, under the conditions similar to those for the preparation of compound 1c. 60c1: LCMS ESI(+): 382 (M+1)$^+$; 60c2: LCMS ESI(+): 382 (M+1)$^+$.

Step 4: (6'-Hydroxy-(4-methoxyphenyl)-8'-oxo-8'H-spiro[cyclohexane-1,5'-indolizine]-7'-carbonyl glycine (60)

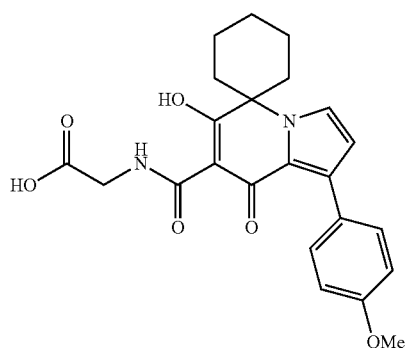

60

The synthetic route of the fourth step for compound 15 of Example 15 was repeated, wherein the starting material 15c was replaced with 60c1 to afford compound 60. LCMS ESI(+): 425 (M+1)$^+$.

Step 5: (6'-Hydroxy-2'-(4-methoxyphenyl)-8'-oxo-8'H-spiro[cyclohexane-1,5'-indolizine]-7'-carbonyl glycine (61)

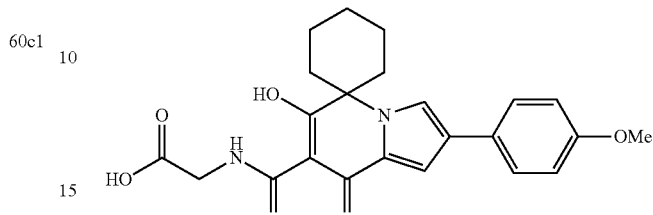

61

The synthetic route of the fourth step for compound 15 of Example 15 was repeated, wherein the starting material 15c was replaced with 60c2 to afford compound 61. LCMS ESI(+): 425 (M+1)$^+$.

Examples 62 and 63: (1'-cyclopropyl-6'-hydroxy-8'-oxo-8'H-spiro[cyclopentane-1,5'-indolizine]-7'-carbonyl)glycine (62) and (2'-Cyclopropyl-6'-hydroxy-8'-oxo-8'H-spiro[cyclopentane-1,5'-indolizine]-7'-carbonyl)glycine (63)

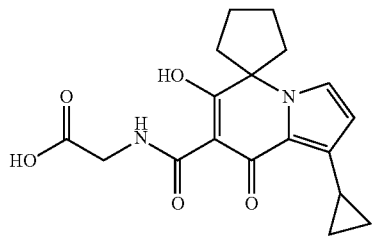

62

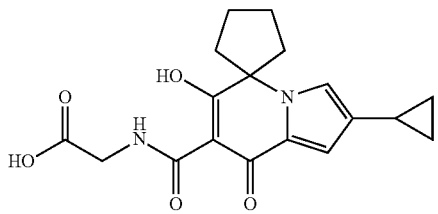

63

Step 1: 1-(3-bromo-1H-pyrrole-1-yl)cyclopentane-1-carboxylic acid (62-Br)

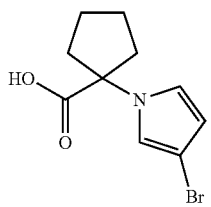

62-Br

The synthetic route of the first step for compound 52-Br of Examples 52 and 53 was repeated, wherein the starting material 13a was replaced with 8a to afford compound 62-Br. LCMS ESI(+): 258 (M+1)⁺. ¹H NMR (500 MHz, dmso-d6) δ (ppm): 12.9 (br s, 1H), 7.0 (m, 1H), 6.88 (m, 1H), 6.1 (m, 1H), 2.4-2.2 (m, 4H), 1.9-1.6 (m, 4H).

Step 2: 1-(3-cyclopropyl-1H-pyrrol-1-yl)cyclopentane-1-carboxylic acid (62a)

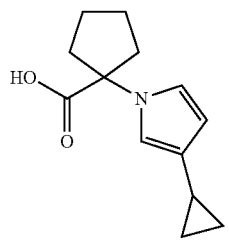

62a

The synthetic route of the second step for compound 52a of Examples 52 and 53 was repeated, wherein the starting material 52-Br was replaced with 62-Br to afford compound 62a. LCMS ESI(+): 220 (M+1)⁺. ¹H NMR (500 MHz, dmso-d6) δ (ppm): 12.63 (1H, br s), 6.67 (1H, t), 6.61 (1H, t), 5.72 (1H, t), 2.45-2.34 (4H, m), 2.24-2.20 (1H, m), 2.19-2.14 (2H, m), 1.74-1.67 (2H, m), 0.71-0.69 (2H, m), 0.40-0.38 (2H, m).

Step 3: Dimethyl 2-(1-(3-Cyclopropyl-1H-pyrrol-1-yl)cyclopentane-1-carbonyl) malonate (62b)

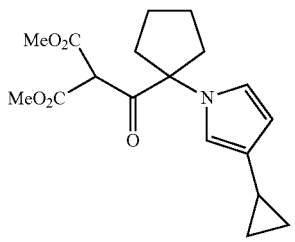

62b

The synthetic route of the second step for compound 52b of Examples 52 and 53 was repeated, wherein the starting material 52a was replaced with 62a to afford compound 62b. LCMS ESI(+): 334 (M+1)⁺. ¹H NMR (500 MHz, dmso-d6) δ (ppm): 6.72 (1H, t), 6.61 (1H, t), 5.88 (1H, t), 4.58 (1H, s), 3.58 (6H, s), 2.37-2.23 (5H, m), 1.73-1.62 (4H, m), 0.75-0.72 (2H, m), 0.43-0.40 (2H, m).

Step 4: Methyl 1'-cyclopropyl-6'-hydroxy-8'-oxo-8'H-spiro[cyclopentane-1,5'-indolizine]-7'-carboxylate (62c1) and Methyl 2'-Cyclopropyl-6'-hydroxy-8'-oxo-8'H-spiro[cyclopentane-1,5'-indolizine]-7'-carboxylate (62c2)

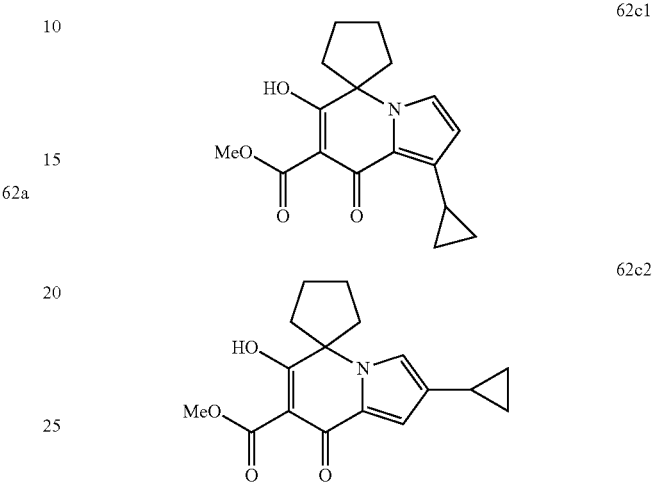

Compounds 62c1 and 62c2 were obtained via purification by column chromatography of two isomers obtained by cyclization of 62b as a starting material with methanesulfonic acid, under the conditions similar to those for the preparation of compound 1c. 62c1: LCMS ESI(+): 302 (M+1)⁺; ¹H NMR (500 MHz, dmso-d6) δ (ppm): 14.75 (1H, s), 7.46 (1H, d), 6.04 (1H, d), 3.82 (3H, s), 2.34-2.30 (2H, m), 2.02-1.97 (1H, m), 1.84-1.74 (6H, m), 0.98-0.96 (2H, m), 0.66-0.65 (2H, m). 62c2: LCMS ESI(+): 302 (M+1)⁺.

Step 5: (1'-Cyclopropyl-6'-hydroxy-8'-oxo-8'H-spiro[cyclopentane-1,5'-indolizine]-7'-carbonyl)glycine (62)

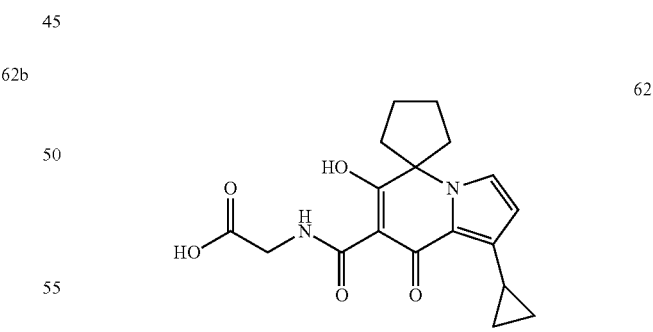

62

The synthetic route of the fourth step for compound 15 of Example 15 was repeated, wherein the starting material 15c was replaced with 62c1 to afford compound 62. LCMS ESI(+): 345 (M+1)⁺. ¹H NMR (500 MHz, dmso-d6) δ (ppm): 18.45 (1H, s), 13.01 (1H, s), 10.06 (1H, t), 7.44 (1H, d), 6.03 (1H, d), 5.77 (1H, s), 4.08 (2H, d), 2.39-2.36 (2H, m), 1.97-1.96 (6H, m), 1.85-1.84 (6H, m), 0.97-0.95 (2H, m), 0.66-0.62 (2H, m).

Step 6: (2'-Cyclopropyl-6'-hydroxy-8'-oxo-8'H-spiro[cyclopentane-1,5'-indolizine]-7'-carbonyl)glycine (63)

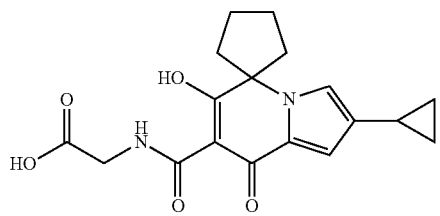

The synthetic route of the fourth step for compound 15 of Example 15 was repeated, wherein the starting material 15c was replaced with 62c2 to afford compound 63. LCMS ESI(+): 345 (M+1)$^+$.

Examples 64-65: (6'-Hydroxy-8'-oxo-1'-phenyl-8'H-spiro[cyclopentane-1,5'-indolizine]-7'-carbonyl)glycine (64) and (6'-Hydroxy-8'-oxo-2'-phenyl-8'H-spiro[cyclopentane-1,5'-indolizine]-7'-carbonyl)glycine (65)

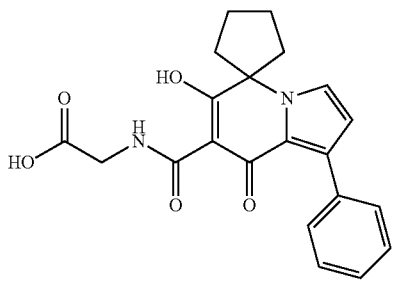

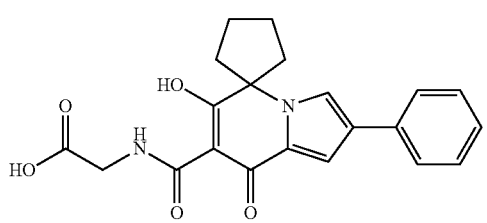

Step 1: 1-(3-phenyl-1H-pyrrol-1-yl)cyclopentane-1-carboxylic acid (64a)

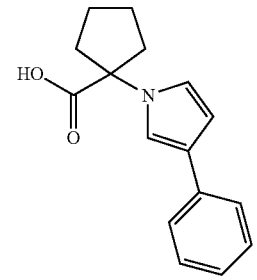

Compound 64a was prepared by Suzuki coupling reaction: compound 62-Br (1 eq.), phenylborate (1.5 eq.), Pd(PPh$_3$)$_2$Cl$_2$ (0.05 eq.), and 2M aqueous sodium carbonate solution (3 eq.) were mixed in n-propanol (4 vol.) and refluxed for 3 hours under nitrogen. After cooling, the reaction solution was diluted with water, acidified with diluted aqueous hydrochloric acid, and extracted with ethyl acetate. The ethyl acetate layer was separated, then washed twice with dilute aqueous sodium chloride, dried over anhydrous sodium sulfate, and filtered to remove the desiccant and then dried on a rotary evaporator. The residue was purified by column chromatography to afford product 64a. LCMS ESI(+): 256 (M+1)$^+$. $^1$H NMR (500 MHz, dmso-d6) δ (ppm): 7.47-7.50 (2H, m), 7.26 (2H, t, J=8.0 Hz), 7.22 (1H, t, J=2.0 Hz), 7.05 (1H, t, J=7.5 Hz), 6.81 (1H, t, J=2.5 Hz), 6.31-6.33 (1H, m), 2.42-2.48 (2H, m), 2.02-2.07 (2H, m), 1.65-1.72 (2H, m), 1.58-1.63 (2H, m).

Step 2: Dimethyl 2-(1-(3-phenyl-1H-pyrrol-1-yl)cyclopentane-1-carbonyl)malonate (64b)

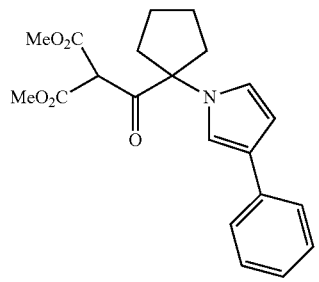

The synthetic route of the second step for compound 15b of Example 15 was repeated, wherein the starting material 15a was replaced with 64a to afford compound 64b. LCMS ESI(+): 370 (M+1)$^+$. $^1$H NMR (500 MHz, dmso-d6) δ (ppm): 7.56 (2H, d, J=7.0 Hz), 7.36 (1H, t, J=2.0 Hz), 7.31 (2H, t, J=7.5 Hz), 7.13 (1H, t, J=7.5 Hz), 6.93 (1H, t, J=2.5 Hz), 6.54-6.55 (1H, m), 4.88 (1H, s), 3.53 (3H, s), 2.35-2.44 (4H, m), 1.66-1.78 (4H, m).

Step 3: Methyl 6'-Hydroxy-8'-oxo-1'-phenyl-8'H-spiro[cyclopentane-1,5'-indolizine]-7'-carboxylate (64c1) and Methyl 6'-Hydroxy-8'-oxy-2'-phenyl-8'H-spiro[cyclopentane-1,5'-indolizine]-7'-carboxylate (64c2)

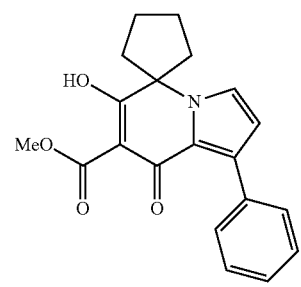
64c1

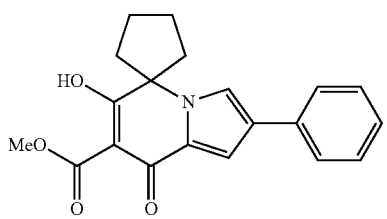
64c2

Compounds 64c1 and 64c2 were obtained via purification by column chromatography of two isomers obtained by cyclization of 64b as a starting material with methanesulfonic acid, under the conditions similar to those for the preparation of compound 1c. 64c1: LCMS ESI(+): 338 (M+1)+; 1H NMR (500 MHz, dmso-d6) δ (ppm): 14.44 (1H, s), 7.65 (2H, s), 7.50-7.53 (2H, m), 7.37 (2H, t, J=7.5 Hz), 7.30-7.33 (1H, m), 6.51 (1H, d, J=4.5 Hz), 3.80 (3H, s), 2.40-2.45 (2H, m), 1.89-1.98 (4H, m), 1.80-1.84 (2H, m). 64c2: LCMS ESI(+): 338 (M+1)+; 1H NMR (500 MHz, dmso-d6) δ (ppm): 14.10 (1H, s), 8.12 (1H, d), 7.80 (2H, d), 7.44 (3H, d), 7.29 (1H, t), 3.88 (3H, s), 2.48-2.43 (2H, m), 2.13-2.10 (2H, m), 2.09-2.00 (2H, m), 1.99-1.85 (2H, m).

Step 4: (6'-Hydroxy-8'-oxo-1'-phenyl-8'H-spiro[cyclopentane-1,5'-indolizine]-7'-carbonyl)glycine (64)

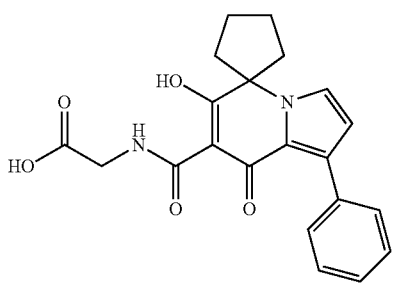
64

The synthetic route of the fourth step for compound 15 of Example 15 was repeated, wherein the starting material 15c was replaced with 64c1 to afford compound 64. LCMS ESI(+): 381 (M+1)+. 1H NMR (500 MHz, dmso-d6) δ (ppm): 18.36 (1H, s), 12.95 (1H, s), 10.11 (1H, s), 7.64 (1H, s), 7.53 (2H, d, J=7.5 Hz), 7.29-7.39 (3H, m), 6.52 (1H, s), 4.07 (2H, d, J=5.5 Hz), 2.44-2.48 (2H, m), 1.89-2.04 (6H, m).

Step 5: (6'-Hydroxy-8'-oxo-2'-phenyl-8'H-spiro[cyclopentane-1,5'-indolizine]-7'-carbonyl)glycine (65)

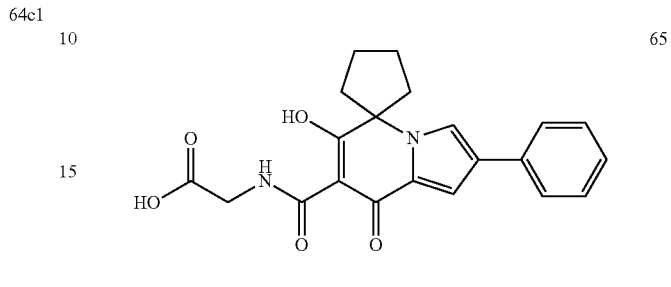
65

The synthetic route of the fourth step for compound 15 of Example 15 was repeated, wherein the starting material 15c was replaced with 64c2 to afford compound 65. LCMS ESI(+): 381 (M+1)+. 1H NMR (500 MHz, dmso-d6) δ (ppm): 18.21 (1H, s), 13.05 (1H, s), 10.03 (1H, s), 8.12 (1H, d), 7.80 (2H, d), 7.43 (3H, d), 7.29 (1H, t), 4.16 (2H, d), 2.51 (2H, br, s), 2.16-1.96 (6H, m).

Example 66: (6'-Hydroxy-8'-oxo-1'-phenyl-8'H-spiro[cyclopentane-1,5'-indolizine]-7'-carbonyl)-L-alanine (66)

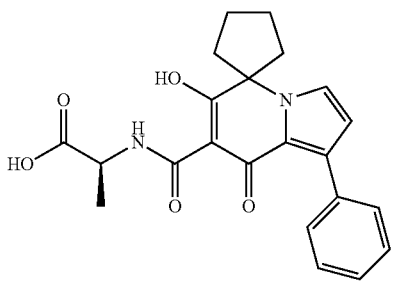
66

Step 1: (6'-Hydroxy-8'-oxo-1'-phenyl-8'H-spiro[cyclopentane-1,5'-indolizine]-7'-carbonyl)-L-alanine (66)

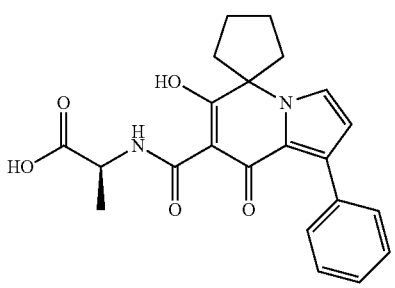
66

The synthetic route of the first step of Example 2 was repeated, wherein the starting material 1c was replaced with 64c1 to afford compound 66. LCMS ESI(+): 381 (M+1)⁺. ¹H NMR (500 MHz, dmso-d6) δ (ppm): 18.36 (1H, s) 12.95 (1H, s), 10.11 (1H, s), 7.64 (1H, s), 7.53 (2H, d, J=7.5 Hz), 7.29-7.39 (3H, m) 6.52 (1H, s) 4.07 (2H, d, J=5.5 Hz), 2.44-2.48 (2H, m), 1.89-2.04 (6H, m).

Example 67: (6'-Hydroxy-8'-oxo-8'H-spiro[cyclo-heptane-1,5'-indolizine]-7'-carbonyl)glycine (67)

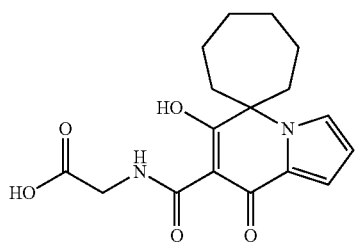

Step 1: 1-(1H-pyrrol-1-yl)cycloheptane-1-carboxylic acid (67a)

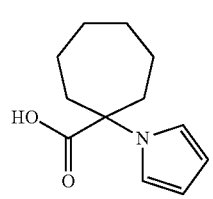

The synthetic route of the first step of Example 6 was repeated, wherein the starting material 1-aminocyclobutane-1-carboxylic acid was replaced by 1-aminocycloheptane-1-carboxylic acid, which was prepared according to the literature ACS Combinatorial Sciences, 2016, 18(6), 330-336, to afford compound 67a. ¹H NMR (400 MHz, dmso-d6) δ (ppm): 12.80 (br, 1H), 6.82 (t, 2H), 6.00 (t, 2H), 2.4-2.2 (m, 4H), 1.7-1.4 (m, 8H). LC MS ESI(+): 208 (M+H)⁺.

Step 2: Dimethyl 2-(1-(1H-pyrrol-1-yl)cycloheptan-1-yl)malonate (67b)

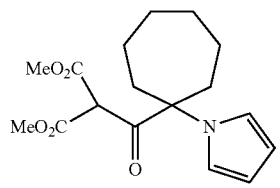

The synthetic route of the second step of Example 8 was repeated, wherein the starting materials diethyl malonate and 8a were respectively replaced with dimethyl malonate and 67a to afford compound 67b. ¹H NMR (500 MHz, dmso-d6) δ (ppm): 6.85 (t, 2H), 6.13 (t, 2H), 4.50 (s, 1H), 3.56 (s, 6H), 2.4-2.1 (m, 4H), 1.7-1.4 (m, 8H). LC MS ESI(+): 322 (M+H)⁺.

Step 3: Ethyl 6'-Hydroxy-8'-oxo-8'H-spiro[cyclo-heptane-1,5'-indolizine]-7'-carboxylate (67c)

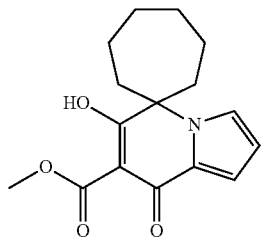

The synthetic route of the third step of Example 8 was repeated, wherein the starting material 8b was replaced with 67b to afford compound 67c. LC MS ESI(+): 290 (M+H)⁺. ¹H NMR (500 MHz, dmso-d6) δ (ppm): 12.8 (br, 1H), 7.71 (dd, 1H, J=1.5 Hz, 2.5 Hz), 7.03 (dd, 1H, J=1.6 Hz, J=4.0 Hz), 6.45 (dd, 1H, J=2.6 Hz, J=4.1 Hz), 3.81 (s, 3H), 2.3-1.5 (m, 12H).

Step 4: (6'-Hydroxy-8'-oxo-8'H-spiro[cycloheptane-1,5'-indolizine]-7'-carbonyl)glycine (67)

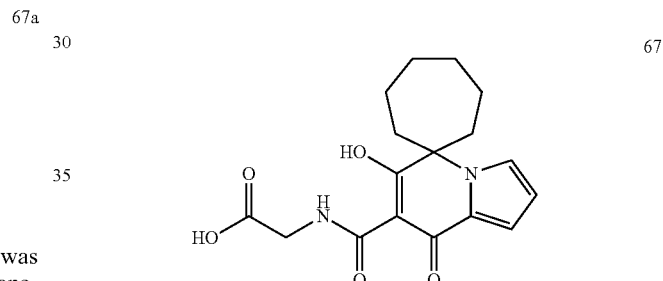

The synthetic route of the fourth step of Example 6 was repeated, wherein the starting material 6c was replaced with 67c to afford compound 67. LCMS ESI(+): 333 (M+1)⁺. ¹H NMR (500 MHz, dmso-d6) δ (ppm): 18.01 (s, 1H), 12.98 (br, s, 1H), 9.91 (br, s, 1H), 7.73 (br s, 1H), 7.00 (d, 1H, J=3.6 Hz), 6.47 (t, 1H), 4.07 (d, 2H, J=5.4 Hz), 2.35-1.50 (m, 12H).

Example 68: ((1,4-trans)-6'-hydroxy-4-methyl-8'-oxo-8'H-spiro[cyclohexane-1,5'-indolizine]-7'-carbonyl)glycine (68)

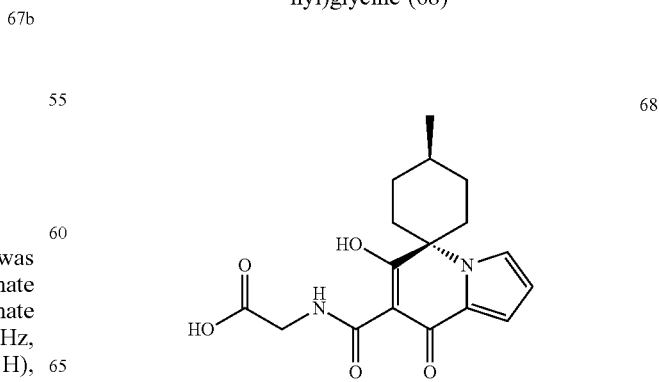

Step 1: (1,4-trans)-4-methyl-1-(1H-pyrrol-1-yl)cyclohexane-1-carboxylic Acid (68a)

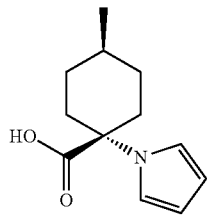

68a

The synthetic route of the fourth step of Example 6 was repeated, wherein the starting material 1-aminocyclobutane-1-carboxylic acid was replaced by (1,4-trans)-1-amino-4-methyl cyclohexane-1-carboxylic acid (CAS: 32958-46-6; which was prepared according to J. Chem. Soc. 1961, 4372-9) to afford compound 68a. $^1$H NMR (400 MHz, dmso-d6) δ (ppm): 12.94 (s, 1H), 6.88 (t, 2H), 6.01 (t, 2H), 2.7-2.6 (m, 2H), 1.8-1.6 (m, 4H), 1.6-1.3 (br, m, 1H), 1.10 (t, 2H, J=11.6 Hz), 0.88 (d, 3H, J=6.2 Hz). LC MS ESI(+): 208 (M+H)$^+$.

Step 2: dimethyl 2-((1,4-trans)-4-methyl-1-(1H-pyrrol-1-yl)cyclohexane-1-yl)malonate (68b)

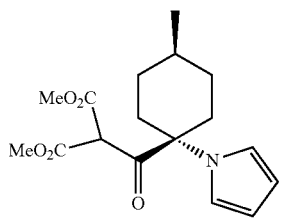

68b

The synthetic route of the second step of Example 8 was repeated, wherein the starting materials diethyl malonate and 8a were respectively replaced with dimethyl malonate and 68a to afford compound 68b. $^1$H NMR (500 MHz, dmso-d6) δ (ppm): 6.86 (t, 2H), 6.10 (t, 2H), 4.78 (s, 1H), 3.54 (s, 6H), 2.59 (br, 1H), 2.0-1.2 (m, 8H), 0.90 (d, 3H, J=6.4 Hz). LC MS ESI(+): 322 (M+H)$^+$.

Step 3: Methyl (1,4-trans)-6'-hydroxy-4-methyl-8'-oxo-8'H-spiro[cyclohexane-1,5'-indolizine]-7'-carboxylate (68c)

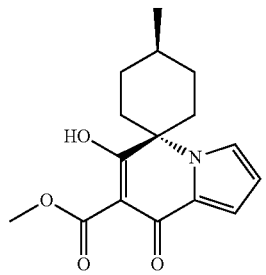

68c

The synthetic route of the third step of Example 8 was repeated, wherein the starting material 8b was replaced with 68b to afford compound 68c. $^1$H NMR (500 MHz, dmso-d6) δ (ppm): 13.70 (br, s, 1H), 7.74 (br s, 1H), 6.99 (d, 1H), 6.46 (t, 1H), 3.81 (s, 3H), 1.99 (m, 4H), 1.57 (m, 5H), 0.93 (br s, 3H). LC MS ESI(+): 290 (M+H)$^+$.

Step 4: ((1,4-trans)-6'-hydroxy-4-methyl-8'-oxo-8'H-spiro[cyclohexane-1,5'-indolizine]-7'-carbonyl)glycine (68)

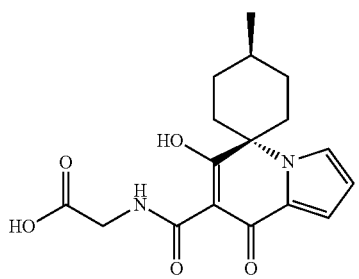

68

The synthetic route of the fourth step of Example 6 was repeated, wherein the starting material 6c was replaced with 68c to afford compound 68. $^1$H NMR (500 MHz, dmso-d6) δ (ppm): 18.06 (s, 1H), 12.90 (br s, 1H), 9.89 (t, 1H), 7.79 (br s, 1H), 6.96 (d, 1H, J=3.2 Hz), 6.48 (t, 1H), 4.07 (d, 2H, J=5.8 Hz), 2.2-1.5 (m, 9H), 0.97 (br, 1H). LCMS ESI(+): 333 (M+1)$^+$.

Example 69: ((1,4-cis)-6'-hydroxy-4-methyl-8'-oxo-8'H-spiro[cyclohexane-1,5'-indolizine]-7'-carbonyl)glycine (69)

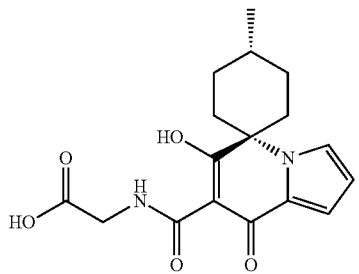

69

Step 1: (1,4-cis)-4-methyl-1-(1H-pyrrol-1-yl)cyclohexane-1-carboxylic Acid (69a)

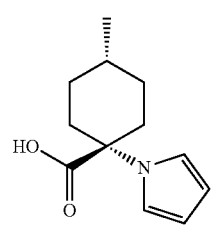

69a

The synthetic route of the fourth step of Example 6 was repeated, wherein the starting material 1-aminocyclobutane-1-carboxylic acid was replaced by (1,4-cis)-1-amino-4-methyl cyclohexane-1-carboxylic acid (CAS: 32958-45-5; which was prepared according to J. Chem. Soc. 1961, 4372-9) to afford compound 69a. ¹H NMR (400 MHz, dmso-d6) δ (ppm): 12.66 (br s, 1H), 6.88 (t, 2H), 6.03 (t, 2H), 2.54 (m, 1H), 2.1-1.9 (m, 2H), 1.65-1.36 (m, 3H), 1.0-0.84 (m, 3H), 0.76 (d, 3H, J=6.4 Hz). LC MS ESI(+): 208 (M+H)⁺.

Step 2: dimethyl 2-((1,4-cis)-4-methyl-1-(1H-pyrrol-1-yl)cyclohexane-1-yl)malonate (69b)

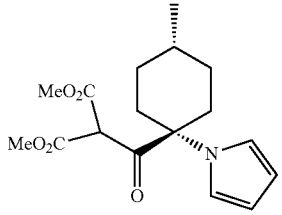

69b

The synthetic route of the second step of Example 8 was repeated, wherein the starting materials diethyl malonate and 8a were respectively replaced with dimethyl malonate and 69a to afford compound 69b. ¹H NMR (500 MHz, dmso-d6) δ (ppm): 6.93 (t, 2H), 6.15 (t, 2H), 4.54 (s, 1H), 3.57 (s, 6H), 2.5 (m, 1H), 2.0-1.8 (m, 2H), 1.7-1.35 (m, 3H), 1.0-0.80 (m, 3H), 0.75 (d, 3H, J=6.4 Hz). LC MS ESI(+): 322 (M+H)⁺.

Step 3: Methyl (1,4-cis)-6'-hydroxy-4-methyl-8'-oxo-8'H-spiro[cyclohexane-1,5'-indolizine]-7'-carboxylate (69c)

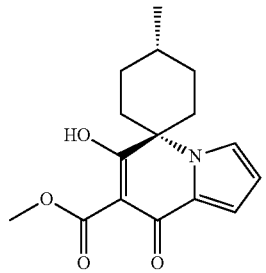

69c

The synthetic route of the third step of Example 8 was repeated, wherein the starting material 8b was replaced with 69b to afford compound 69c. ¹H NMR (500 MHz, dmso-d6) δ (ppm): 13.8 (br, s, 1H), 7.77 (dd, 1H, J=1.4 Hz, 2.4 Hz), 7.06 (dd, 1H, J=1.6 Hz, J=4.0 Hz), 6.44 (dd, 1H, J=2.4 Hz, J=4.0 Hz), 3.80 (s, 3H), 2.2-2.0 (m, 2H), 1.85-1.65 (m, 4H), 1.65-1.20 (m, 3H), 1.00 (d, 3H, J=6.2 Hz). LC MS ESI (+): 290 (M+H)⁺.

Step 4: ((1,4-cis)-6'-hydroxy-4-methyl-8'-oxo-8'H-spiro[cyclohexane-1,5'-indolizine]-7'-carbonyl)glycine (69)

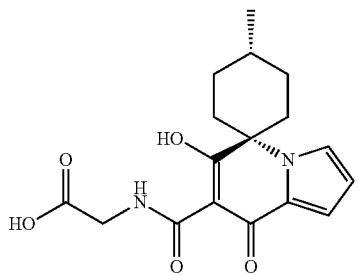

69

The synthetic route of the fourth step of Example 6 was repeated, wherein the starting material 6c was replaced with 69c to afford compound 69. ¹H NMR (500 MHz, dmso-d6) δ (ppm): 18.04 (s, 1H), 12.98 (br, s, 1H), 9.93 (br, 1H), 7.81 (br, s, 1H), 7.05 (d, 1H, J=3.8 Hz), 6.46 (d, 1H, J=3.4 Hz), 4.07 (d, 2H, J=5.6 Hz), 2.3-1.3 (m, 9H), 1.04 (d, 3H, J=6.2 Hz). LCMS ESI(+): 333 (M+1)⁺.

Examples 70 and 71: (6'-Hydroxy-8'-oxo-1'-phenyl-8'H-spiro[cyclobutane-1,5'-indolizine]-7'-carbonyl) glycine (L) and (6'-Hydroxy-8'-oxo-2'-phenyl-8'H-spiro[cyclobutane-1,5'-indolizine]-7'-carbonyl) glycine (a)

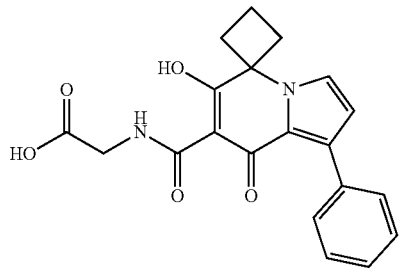

70

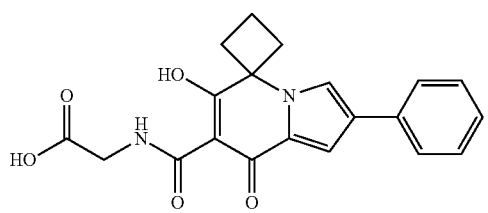

71

Step 1: 1-(3-bromo-1H-pyrrol-1-yl)cyclobutane-1-carboxylic Acid (70-Br)

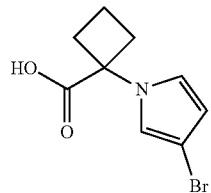

The synthetic route of the first step for compound 52-Br of Examples 52 and 53 was repeated, wherein the starting material 13a was replaced with 6a to afford compound 70-Br. LCMS ESI(+): 244 (M+1)$^+$.

Step 2: 1-(3-phenyl-1H-pyrrol-1-yl)cyclobutane-1-carboxylic Acid (70a)

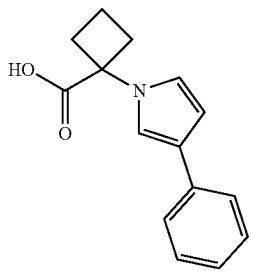

The synthetic route of the second step for compound 52a of Examples 52 and 53 was repeated, wherein the starting materials cyclopropylborate and 52-Br were respectively replaced with phenylborate and 70-Br to afford compound 70a. LCMS ESI(+): 242 (M+1)$^+$.

Step 3: Dimethyl 2-(1-(3-phenyl-1H-pyrrol-1-yl)cyclobutane-1-carbonyl) malonate (70b)

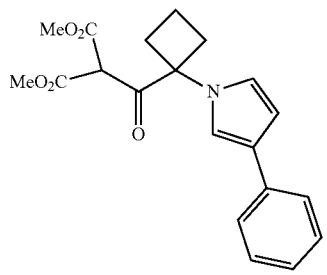

The synthetic route of the second step for compound 52b of Examples 52 and 53 was repeated, wherein the starting material 52a was replaced with 70a to afford compound 70b. LCMS ESI(+): 356 (M+1)$^+$.

Step 4: Methyl 6'-Hydroxy-8'-oxo-1'-phenyl-8'H-spiro[cyclobutane-1,5'-indolizine]-7'-carboxylate (70c1) and Methyl 6'-Hydroxy-8'-oxy-2'-phenyl-8'H-spiro[cyclobutane-1,5'-indolizine]-7'-carboxylate (70c2)

Compounds 70c1 and 70c2 were obtained via purification by column chromatography of two isomers obtained by cyclization of 70b as a starting material with methanesulfonic acid, under the conditions similar to those for the preparation of compound 1c. 70c1: LCMS ESI(+): 324 (M+1)$^+$; 70c2: LCMS ESI(+): 324 (M+1)$^+$.

Step 5: (6'-Hydroxy-8'-oxo-1'-phenyl-8'H-spiro[cyclobutane-1,5'-indolizine]-7'-carbonyl)glycine (70)

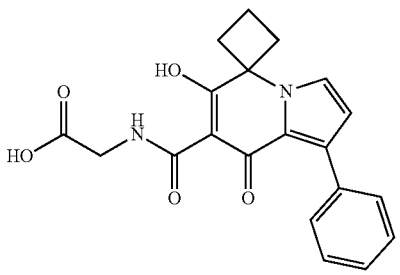

The synthetic route of the fourth step for compound 15 of Example 15 was repeated, wherein the starting material 15c was replaced with 70c1 to afford compound 70. LCMS ESI(+): 367 (M+1)$^+$.

Step 6: (6'-Hydroxy-8'-oxo-2'-phenyl-8'H-spiro[cyclobutane-1,5'-indolizine]-7'-carbonyl)glycine (a)

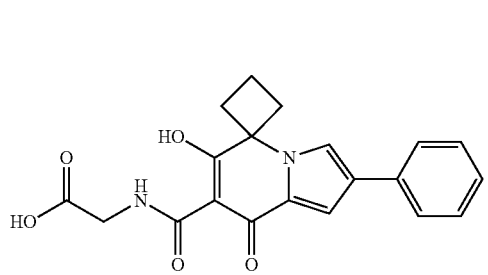

71

The synthetic route of the fourth step for compound 15 of Example 15 was repeated, wherein the starting material 15c was replaced with 70c2 to afford compound 71. LCMS ESI(+): 367 (M+1)⁺.

Example 72: (6'-Hydroxy-8'-oxo-3'-phenyl-8'H-spiro[cyclopentane-1,5'-indolizine]-7'-carbonyl)glycine-2,2-dideuterium (72)

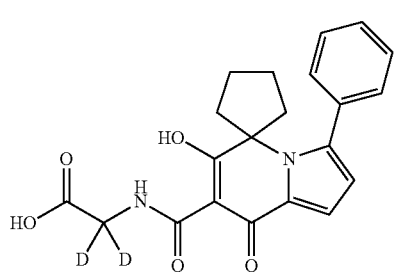

72

Step 1: (6'-Hydroxy-8'-oxo-3'-phenyl-8'H-spiro[cyclopentane-1,5'-indolizine]-7'-carbonyl)glycine-2,2-dideuterium (72)

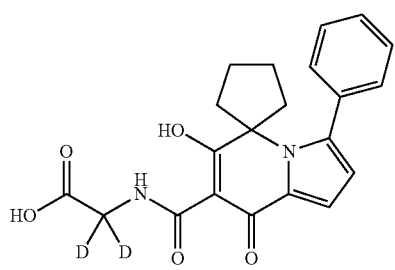

72

The compound of Example 24, glycine-2,2-dideuterium and 0.5 M NaOMe solution in methanol were combined, and then dried under reduced pressure to give a residue, to which 2-methoxyethanol was added. The resulting reaction mixture was refluxed for 1.5 hours. The reaction solution was then cooled, diluted with water, and then acidified to pH 2-3 with 2 M aqueous hydrochloric acid to give solid. The solid was filtered under reduced pressure and washed with water to afford the product, i.e. the compound 72. LCMS ESI(+): 383 (M+1)⁺. ¹H NMR (500 MHz, dmso-d6) δ (ppm): 17.95 (s, 1H), 12.93 (s, 1H), 9.86 (s, 1H), 7.49 (m, 5H), 7.07 (d, J=3.6 Hz, 1H), 6.35 (d, J=3.6 Hz, 1H), 2.29 (m, br, 2H), 2.15 (m, br, 2H), 1.53 (m, br, 2H), 0.93 (m, br, 2H).

Example 73: (6'-Hydroxy-3'-(4-hydroxyphenyl)-8'-oxo-8'H-spiro[cyclopentane-1,5'-indolizine]-7'-carbonyl)glycine (73)

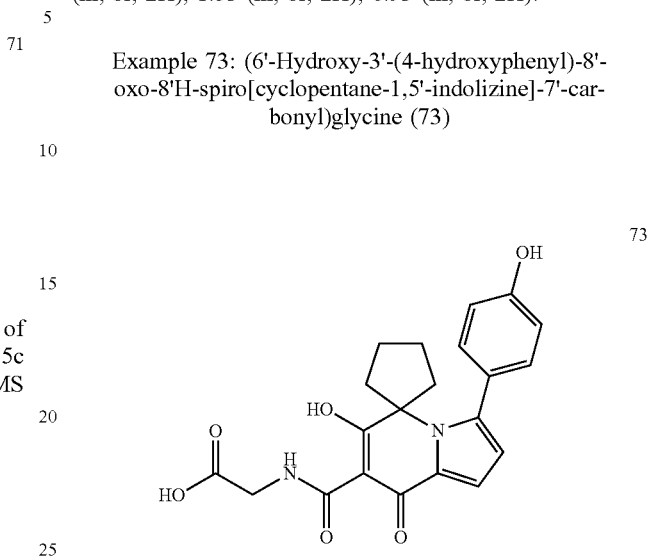

73

Step 1: (6'-Hydroxy-3'-(4-hydroxyphenyl)-8'-oxo-8'H-spiro[cyclopentane-1,5'-indolizine]-7'-carbonyl)glycine (73)

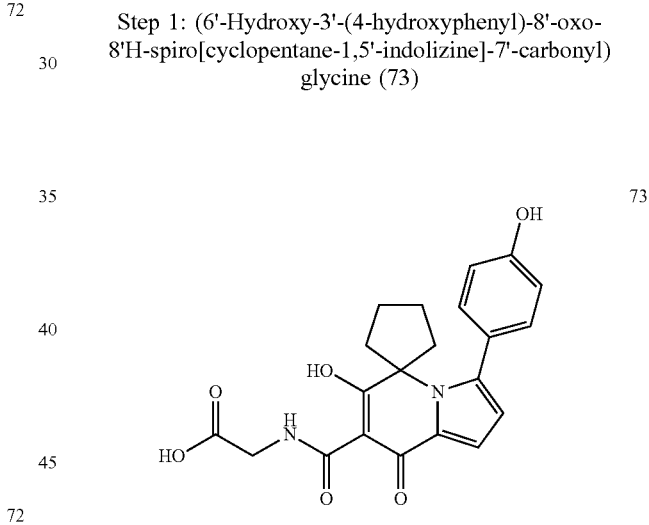

73

The compound 28 of Example (100 mg) was dissolved in dichloromethane (1.5 ml), and cooled with ice-water bath, to which a solution of boron tribromide in dichloromethane (0.96 ml, concentration: 1 M) was added. The resulting mixture was then stirred at RT for 1.5 hours. After reaction, an aqueous solution of sodium carbonate was added and the solution was extracted twice with ethyl acetate. The aqueous phase was acidified to pH=3-4 with 1 M aqueous hydrochloric acid and extracted with ethyl acetate. The ethyl acetate phase was washed twice with dilute aqueous sodium chloride solution, dried over anhydrous sodium sulfate, filtered, and concentrated. Crystallization of residue from ethanol gave the solid product as Compound 73 (64 mg). LCMS ESI(+): 397 (M+1)⁺. ¹H NMR (500 MHz, dmso-d6) δ (ppm): 17.88 (s, 1H), 12.92 (s, 1H), 9.88 (s, 1H), 9.78 (s, 1H), 7.35-7.23 (m, 2H), 7.04 (d, J=4.0 Hz, 1H), 6.88-6.78 (m, 2H), 6.29 (d, J=4.1 Hz, 1H), 4.07 (d, J=5.5 Hz, 2H), 2.34-2.21 (m, 2H), 2.15 (m, 2H), 1.56 (m, 2H), 1.03 (m, 2H).

Example 74: (6'-Hydroxy-3'-(2-methoxyphenyl)-8'-oxo-8'H-spiro[cyclopentane-1,5'-indolizine]-7'-carbonyl glycine (74)

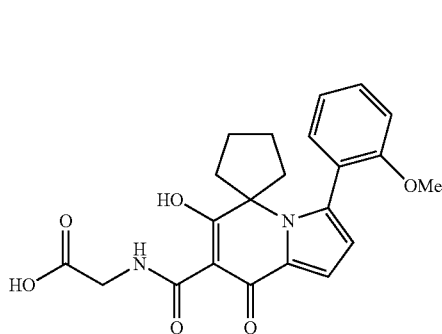

Step 1: 1-(2-(2-methoxyphenyl)-1H-pyrrol-1-yl)cyclopentane-1-carboxylic Acid (74a)

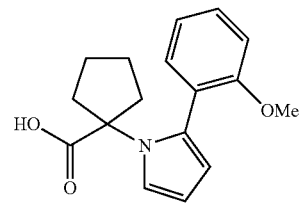

The synthetic route of the first step for compound 24a of Example 24 was repeated, wherein the starting material 3-(1,3-dioxane-2-yl)-1-phenylpropan-1-one was replaced by 3-(1,3-dioxane-2-yl)-1-(2-methoxyphenyl)propan-1-one, which was prepared according to the method described in Liebis Annalen der Chemie, 1989, (9), 863-881, to afford compound 74a. LCMS ESI(+): 286 (M+1)+.

Step 2: Dimethyl 2-(1-(2-(2-methoxyphenyl)-1H-pyrrol-1-yl)cyclopentane-1-carbonyl)malonate (74b)

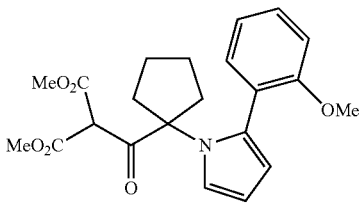

The synthetic route of the second step for compound 15b of Example 15 was repeated, wherein the starting material 15a was replaced with 74a to afford compound 74b. LCMS ESI(+): 400 (M+1)+.

Step 3: Methyl 6'-Hydroxy-3'-(2-methoxyphenyl)-8'-oxo-8'H-spiro[cyclopentane-1,5'-indolizine]-7'-carboxylate (74c)

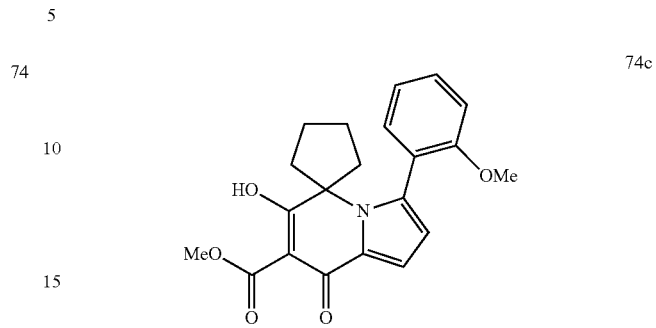

The synthetic route of the third step for compound 15c of Example 15 was repeated, wherein the starting material 15b was replaced with 74b to afford compound 74c. LCMS ESI(+): 368 (M+1)+.

Step 4: (6'-Hydroxy-3'-(2-methoxyphenyl)-8'-oxo-8'H-spiro[cyclopentane-1,5'-indolizine]-7'-carbonyl glycine (74)

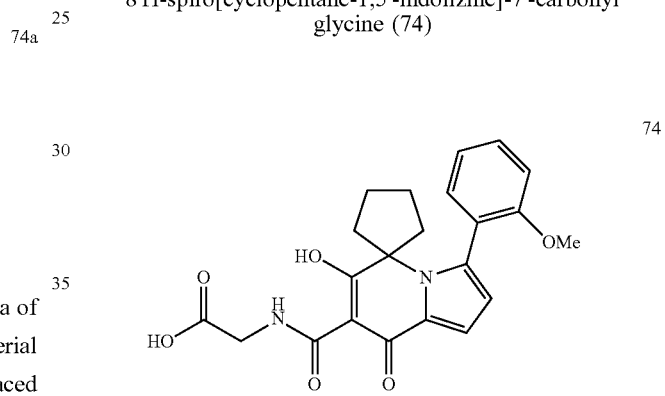

The synthetic route of the fourth step for compound 15 of Example 15 was repeated, wherein the starting material 15c was replaced with 74c to afford compound 74. LCMS ESI(+): 411 (M+1)+. $^1$H NMR (500 MHz, dmso-d6) δ (ppm): 17.9 (1H, s), 12.94 (1H, s), 9.89 (1H, s), 7.53-7.50 (1H, m), 7.39-7.37 (1H, m), 7.16-7.14 (1H, m), 7.07-7.04 (1H, m), 6.29 (1H, d), 4.08 (2H, d), 3.75 (3H, s), 2.3-2.1 (4H, br), 1.6-1.48 (2H, br), 1.0-0.8 (2H, br).

Example 75: (6'-Hydroxy-3'-(3-methoxyphenyl)-8'-oxo-8'H-spiro[cyclopentane-1,5'-indolizine]-7'-carbonyl glycine (75)

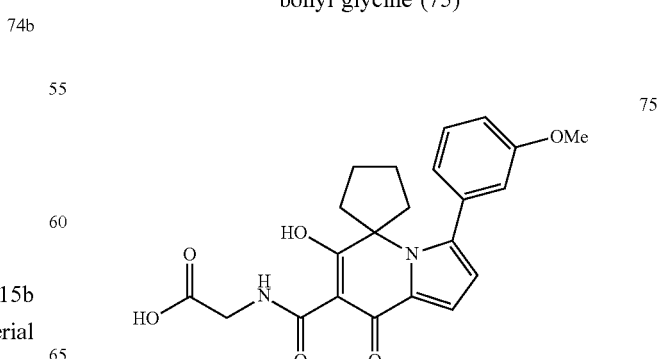

Step 1: 1-(2-(3-methoxyphenyl)-1H-pyrrol-1-yl)cyclopentane-1-carboxylic Acid (75a)

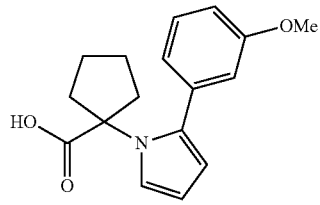
75a

The synthetic route of the first step for compound 24a of Example 24 was repeated, wherein the starting material 3-(1,3-dioxane-2-yl)-1-phenylpropan-1-one was replaced by 3-(1,3-dioxane-2-yl)-1-(3-methoxyphenyl)propan-1-one, which was prepared according to the method described in Liebis Annalen der Chemie, 1989, (9), 863-881, to afford compound 75a. LCMS ESI(+): 286 (M+1)$^+$.

Step 2: Dimethyl 2-(1-(2-(3-methoxyphenyl)-1H-pyrrol-1-yl)cyclopentane-1-carbonyl)malonate (75b)

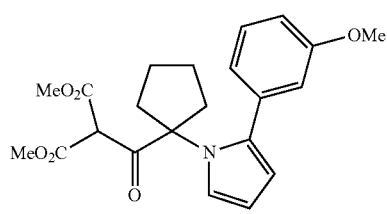
75b

The synthetic route of the second step for compound 15b of Example 15 was repeated, wherein the starting material 15a was replaced with 75a to afford compound 75b. LCMS ESI(+): 400 (M+1)$^+$.

Step 3: Methyl 6'-Hydroxy-3'-(3-methoxyphenyl)-8'-oxo-8'H-spiro[cyclopentane-1,5'-indolizine]-7'-carboxylate (74c)

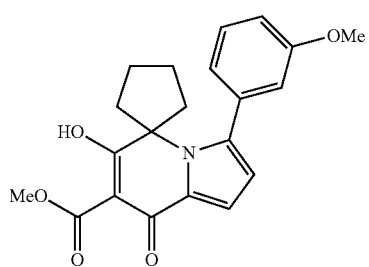
75c

The synthetic route of the third step for compound 15c of Example 15 was repeated, wherein the starting material 15b was replaced with 75b to afford compound 75c. LCMS ESI(+): 368 (M+1)$^+$.

Step 4: (6'-Hydroxy-3'-(3-methoxyphenyl)-8'-oxo-8'H-spiro[cyclopentane-1,5'-indolizine]-7'-carbonyl glycine (75)

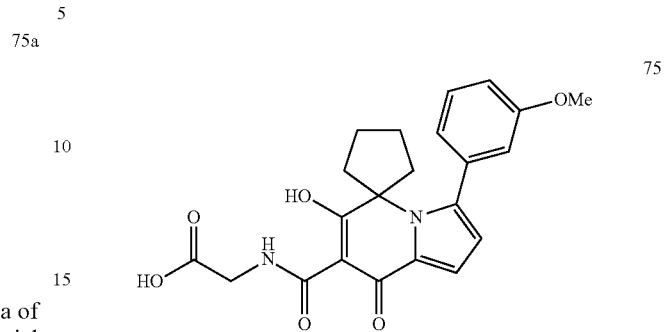
75

The synthetic route of the fourth step for compound 15 of Example 15 was repeated, wherein the starting material 15c was replaced with 75c to afford compound 75. LCMS ESI(+): 411 (M+1)$^+$. $^1$H NMR (500 MHz, dmso-d6) δ (ppm): 12.98 (1H, s), 9.88 (1H, s), 7.40-7.36 (1H, m), 7.08-7.02 (4H, m), 6.36 (1H, d), 4.08 (2H, d), 3.79 (3H, s), 2.29-2.19 (4H, br), 1.57 (2H, br), 1.06-1.01 (2H, br).

Evaluation of Pharmacological Activity

1. Effect of Compounds on Activities of HIF Prolyl Hydroxylase-2

Activities of HIF prolyl hydroxylase was determined according to the method as described in Anal Biochem, 2004, 330: 74-80, which was slightly modified. A 96-well plate was pretreated with blocker casein and 1 mM biotin for 30 minutes, and then biotin-linked HIF-1α556-574 (biotinyl-DLDLEMLAPYIPMDDDFQL) was immobilized on the 96-well plate. The 96-well plate was then filled with an appropriate amount of HIF-PHD2-containing buffer (20 mM Tris (pH 7.5), 5 mM KCl, 1.5 mM MgCl$_2$, 20 mM 2-oxoglutarate, 10 mM FeSO$_4$, 2 mM ascorbic acid, 4% EDTA-free protease inhibitor) and was incubated for 1 to 60 minutes at RT. The reaction mixture also contained different concentrations of HIF prolyl hydroxylase inhibitors to be tested. The reaction was stopped by rinsing the 96-well plate three times with washing buffer. In 100 µl binding buffer (50 mM tris(hydroxymethyl)-aminomethane, pH 7.5, 120 mM NaCl), hydroxylated HIF-1α556-574 was reacted with Eu—VBC protein in the binding buffer at RT for 60 minutes. The reaction solution was aspirated, and the unbound Eu—VBC protein was washed away by washing 3 times with an elution buffer. Subsequently, 10 µl of rabbit anti-Eu—VBC polyclonal antibody was added. After further 30 minutes, 10 µl of anti-rabbit polyclonal antibody immunoglobulin coupled to horseradish peroxidase was added to the binding buffer. To determine the amount of bound Eu—VBC protein, it was incubated with TMB for 15 minutes. The color reaction was terminated by addition of 100 µl of 1 M sulfuric acid. The amount of bound Eu—VBC protein was determined by measuring optical density at 450 nm, which was proportional to the amount of hydroxylated proline in the peptide substrate.

The IC$_{50}$ data in the table below are representative data. These values represent only the data measured by the applicant at the time of filing the application. Due to variations in reagents, measurement conditions, and mode of operation in the methods given above, the IC$_{50}$ data obtained may show some variations. Therefore, these values should be regarded as relative ones rather than absolute ones.

| Examples | PHD2 IC$_{50}$ (μM) |
|---|---|
| 1 | 0.9 |
| 2 | 2.5 |
| 3 | >10 |
| 4 | 0.8 |
| 5 | 2.7 |
| 6 | 0.5 |
| 7 | 1.5 |
| 8 | 0.5 |
| 9 | >10 |
| 10 | >10 |
| 11 | 2.1 |
| 16 | 0.6 |
| 17 | 0.5 |
| 21 | >10 |
| 22 | >10 |
| 30 | 0.8 |
| 32 | 0.7 |
| 45 | 1.1 |
| 46 | >10 |
| 52 | 0.6 |
| 53 | 0.7 |
| 67 | 1.2 |
| 68 | 0.7 |
| 69 | 0.8 |

The above IC$_{50}$ data indicates that compounds of the present invention can effectively inhibit HIF prolyl hydroxylase.

2. Effect of Compounds of Examples on Hemoglobin in Mice

Male C57B1/6 mice of 8-10 weeks (Shanghai Slack Laboratory Animals Co., Ltd.) were administrated orally the test compounds in 30 mg/kg for 2 weeks, 3 times each week and Roxadustat (CAS: 808118-40-3) was administrated in an amount of 60 mg/kg as a positive control. Before the first administration and 6 hours after the last administration, about 30 μl of blood was taken from the mandibular vein, and the hemoglobin content was measured by Hemocue hemoglobin analyzer. The hemoglobin elevation was calculated as the value obtained by subtracting the first hemoglobin content from the hemoglobin content after the last administration.

In addition, hemoglobin elevation was also tested in the same manner for Roxadustat as a positive control. Roxadustat was purchased from Selleckchem, which was known to be a potent inhibitor of HIF prolyl hydroxylase in the art and be able to increase hemoglobin production.

The hemoglobin elevation caused by representative compounds of the invention are given in the table below.

| Examples | Hemoglobin elevation (g/dL) |
|---|---|
| 1 | 1.0 |
| 2 | 0.6 |
| 4 | 0.8 |
| 5 | 1.0 |
| 6 | 0.9 |
| 7 | 0.7 |
| 8 | 3.1 |
| 9 | 2.0 |
| 10 | 1.9 |
| 11 | 2.0 |
| 12 | 0.8 |
| 13 | 4.3 |
| 14 | 1.0 |
| 21 | 1.8 |
| 24 | 4.0 |
| 35 | 2.5 |
| 39 | 4.8 |
| 62 | 0.1 |
| 67 | 0.8 |
| 68 | 5.2 |
| 69 | 0.7 |
| Roxadustat | 1.7 |

As can be seen from the above table, compounds of the present invention showed comparable or even better hemoglobin elevation compared to Roxadustat under the same measurement conditions. The results showed that compounds of the present invention may stabilize HIFs by inhibiting prolyl hydroxylase, and thus can be used as medicine for treating and/or preventing diseases associated with HIFs such as anemia through, among others, increasing erythropoietin production and elevating hemoglobin content.

While embodiments of the present invention have been illustrated and described, it is not intended that all possible embodiments of the invention have been illustrated and described. Rather, the words used in the specification are merely illustrative and not restrictive, and it shall be understood that various changes may be made without departing from the spirit and scope of the invention.

The invention claimed is:

1. A compound of Formula I,

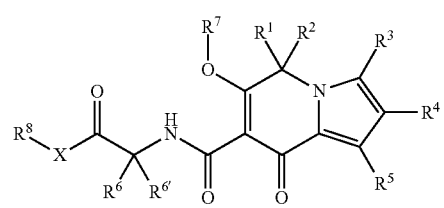

or an isotopically labeled compound thereof, or an optical isomer thereof, a geometric isomer thereof, a tautomer thereof or a mixture of various isomers, or a pharmaceutically acceptable salt thereof, or a prodrug thereof, in which $R^1$ and $R^2$ are each independently selected from the group consisting of cyano, alkyl, heterocyclyl, alkenyl, alkynyl, aryl, heteroaryl, acyl, amino, $R^9O-$, $R^9S-$, $R^9(O=)S-$, and $R^9(O=)_2S-$, wherein $R^9$ is alkyl, heterocyclyl, alkenyl, alkynyl, aryl or heteroaryl; and wherein the alkyl, heterocyclyl, alkenyl, alkynyl, aryl, heteroaryl, acyl, and amino are optionally substituted by one or more substituents wherein the substituents are independently selected from the group consisting of halo, cyano, hydroxy, amino, carboxy, acyl, alkyl, heterocyclyl, alkenyl, alkynyl, aryl, heteroaryl, =O, =S, —SH, $R^{10}O-$, $R^{10}S-$, $R^{10}(O=)S-$, and $R^{10}(O=)_2S-$, and wherein $R^{10}$ is alkyl, heterocyclyl, alkenyl, alkynyl, aryl, or heteroaryl;

or $R^1$ and $R^2$ are taken together to form a ring;

$R^3$, $R^4$ and $R^5$ are each independently selected from the group consisting of hydrogen, halogen, hydroxy, carboxy, cyano, amino, acyl, alkyl, heterocyclyl, alkenyl, alkynyl, aryl, heteroaryl, $R^{11}O—$, $R^{11}S—$, $R^{11}(O=)S—$, and $R^{11}(O=)_2S—$, wherein $R^{11}$ is alkyl, heterocyclyl, alkenyl, alkynyl, aryl or heteroaryl;
wherein the alkyl, heterocyclyl, alkenyl, alkynyl, aryl, heteroaryl, acyl, and amino are optionally substituted by one or more substituents wherein the substituents are independently selected from the group consisting of halogen, cyano, hydroxy, amino, carboxy, acyl, alkyl, heterocyclyl, alkenyl, alkynyl, aryl, heteroaryl, =O, =S, —SH, $R^{12}O—$, $R^{12}S—$, $R^{12}(O=)S—$, and $R^{12}(O=)_2S—$, and wherein $R^{12}$ is alkyl, heterocyclyl, alkenyl, alkynyl, aryl, or heteroaryl;
$R^6$ and $R^{6'}$ are each independently selected from the group consisting of hydrogen and optionally substituted alkyl;
$R^7$ is selected from the group consisting of hydrogen, alkyl and acyl; wherein the alkyl and acyl are optionally substituted by the following groups: halogen, cyano, hydroxy, amino, carboxy, acyl, alkyl, heterocyclyl, alkenyl, alkynyl, aryl, heteroaryl, =O, =S, —SH, $R^{13}O—$, $R^{13}S—$, $R^{13}(O=)S—$, and/or $R^{13}(O=)_2S—$, wherein $R^{13}$ is alkyl, heterocyclyl, alkenyl, alkynyl, aryl, or heteroaryl;
$R^8$ is selected from the group consisting of hydrogen, alkyl and —OC(O)$R^{14}$, wherein $R^{14}$ is alkyl, heterocyclyl, alkenyl, alkynyl, aryl or heteroaryl; wherein the alkyl, heterocyclyl, alkenyl, alkynyl, aryl, or heteroaryl group is optionally substituted with the following groups: halogen, cyano, hydroxy, amino, carboxy, acyl, alkyl, heterocyclyl, alkenyl, alkynyl, aryl, heteroaryl, =O, =S, —SH, $R^{15}O—$, $R^{15}S—$, $R^{15}(O=)S—$, and/or $R^{15}(O=)_2S—$; wherein $R^{15}$ is alkyl, heterocyclyl, alkenyl, alkynyl, aryl, or heteroaryl; and
X is an oxygen atom or a sulfur atom or NH.

2. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein
$R^1$ and $R^2$ are independently selected from the group consisting of cyano, C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members, heteroaryl containing 5 to 14 ring members, C1-C12 acyclic alkyl —C(=O)—, C2-C12 acyclic alkenyl-C(=O)—, amino, $R^9O—$, $R^9S—$, $R^9(O=)S—$, and $R^9(O=)_2S—$, wherein $R^9$ is C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members; wherein the above C1-C12 acyclic alkyl group, C2-C12 acyclic alkenyl group, C2-C12 acyclic alkynyl group, C6-C14 aryl group, C3-C8 cycloalkyl group, C3-C8 cycloalkenyl, heterocycloalkyl having 3 to 8 ring members, heterocycloalkenyl having 3 to 8 ring members, heteroaryl having 5 to 14 ring members, C1-C12 acyclic alkyl-C(=O)—, C2-C12 acyclic alkenyl-C(=O)—, and amino group are optionally substituted by 1 to 3 substituents wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, heteroaryl-O— having 5 to 14 ring members, C1-C6 acyclic alkyl-S—, C3-C8 cycloalkyl-S—, C2-C6 acyclic alkenyl-S—, C2-C6 acyclic alkynyl —S—, C3-C8 cycloalkenyl-S—, C6-C14 aryl-S—, heteroaryl-S— having 5 to 14 ring members, heterocycloalkyl having 3 to 8 ring members, heterocycloalkenyl having 3 to 8 ring members, =O, =S, —SH, —CF$_3$, —CO$_2$C$_1$-C$_6$ acyclic alkyl, C1-C6 acyclic alkyl-S—, C1-C6 acyclic alkyl (O=)S— and C1-C6 acyclic alkyl (O=)$_2$S—; or
$R^1$ and $R^2$ are taken together to form an optionally substituted cycloalkane ring, cycloalkylene ring, heterocycloalkane ring, or heterocycloalkylene ring having 3 to 8 ring members;
$R^3$, $R^4$ and $R^5$ are each independently selected from the group consisting of hydrogen, halogen, hydroxy, carboxy, cyano, C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members, heteroaryl having 5 to 14 ring members, C1-C12 acyclic alkyl-C(=O)—, C2-C12 acyclic alkenyl-C(=O)—, amino, $R^{11}O—$, $R^{11}S—$, $R^{11}(O=)S—$, and $R^{11}(O=)_2S—$wherein $R^{11}$ is C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3-8 ring members, or heterocycloalkenyl having 3 to 8 ring members; wherein the above C1-C12 acyclic alkyl, C2-C12 acyclic alkenyl, C2-C12 acyclic alkynyl, C6-C14 aryl, C3-C8 cycloalkyl, C3-C8 cycloalkenyl, heterocycloalkyl having 3 to 8 ring members, heterocycloalkenyl having 3 to 8 ring members, heteroaryl having 5 to 14 ring members, C1-C12 acyclic alkyl-C(=O)—, C2-C12 acyclic alkenyl-C(=O)—, and amino are optionally substituted with from 1 to 3 substituents wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, heteroaryl-O— having 5 to 14 ring members, C1-C6 acyclic alkyl-S—, C3-C8 cycloalkyl-S—, C2-C6 acyclic alkenyl-S—, C2-C6 acyclic alkynyl-S—, C3-C8 cycloalkenyl-S—, C6-C14 aryl-S—, heteroaryl-S— having 5 to 14 ring members, heterocycloalkyl having 3 to 8 ring members, heterocycloalkenyl having 3 to 8 ring members, =O, =S, —SH, —CF$_3$, —CO$_2$C$_1$—C6 acyclic alkyl group, C1-C6 acyclic alkyl-S—, C1-C6 acyclic alkyl (O=)S— and C1-C6 acyclic alkyl (O=)$_2$S—;
$R^6$ and $R^{6'}$ are each independently selected from the group consisting of hydrogen, C1-C6 acyclic alkyl and C3-C8 cycloalkyl; the above C1-C6 acyclic alkyl and C3-C8 cycloalkyl are optionally substituted by 1 to 3 substituents wherein the substituents are independently selected from the group consisting of hydroxy, halogen, cyano, amino, carboxy, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, and heteroaryl-O— having 5 to 14 ring members;
$R^7$ is selected from the group consisting of hydrogen, C1-C6 acyclic alkyl, C3-C8 cycloalkyl, C1-C6 acyclic alkyl-C(=O)—, and C2-C6 acyclic alkenyl-C(=O)—; wherein the C1—C6 acyclic alkyl, C3-C8 cycloalkyl, C1-C6 acyclic alkyl-C(=O)—, and C2-C6 acyclic alkenyl-C(=O)— are optionally substituted by 1 to 3 substituents, wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, and heteroaryl-O— having 5 to 14 ring members;

$R^8$ is selected from the group consisting of hydrogen, C1-C12 acyclic alkyl, C3-C8 cycloalkyl and —OC(O)—C1—C12 acyclic alkyl; wherein the C1-C12 acyclic alkyl, C3-C8 cycloalkyl and —OC(O)—C1-C12 acyclic alkyl group are optionally substituted by 1 to 3 substituents, wherein the substituents are independently selected from the group consisting of hydroxyl, halogen, cyano, amino, carboxyl, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, and heteroaryl-O— having 5 to 14 ring members; and X is an oxygen atom or a sulfur atom or NH.

3. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 2, wherein $R^1$ and $R^2$ are each independently selected from the group consisting of cyano, amino, and unsubstituted C1-C6 acyclic alkyl; or R1 and R2 are taken together to form an optionally substituted cycloalkane ring or heterocycloalkane ring having 3-8 ring members.

4. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 3, wherein $R^1$ and $R^2$ are each independently selected from methyl and ethyl; or $R^1$ and $R^2$ are taken together to form a cyclopropane ring, a cyclobutane ring, a cyclohexane ring, a methylcyclohexane ring, a cycloheptane ring, tetrahydrofuran ring or tetrahydropyran ring.

5. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^3$, $R^4$ and $R^5$ are each independently selected from the group consisting of hydrogen, halogen, hydroxy, carboxy, cyano, amino, C1-C6 acyclic alkyl, C6-C14 aryl, C3-C8 cycloalkyl, C1-C6 acyclic alkyl —O—, and heteroaryl having 5 to 14 ring members; wherein the above C1-C6 acyclic alkyl, C6-C14 aryl, C3-C8 cycloalkyl, C1-C6 acyclic alkyl-O—, heteroaryl having 5 to 14 ring members and amino are optionally substituted by 1 to 3 substituents, wherein the substituents are independently selected from the group consisting of hydroxyl, halogen, cyano, amino, carboxyl, C6-C14 aryl and C1-C6 acyclic alkyl.

6. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 5, wherein $R^3$, $R^4$ and $R^5$ are each independently selected from the group consisting of hydrogen, halogen, hydroxy, carboxy, cyano, amino, methyl, ethyl, propyl, butyl, phenyl, benzyl, tolyl, methoxyphenyl, chlorophenyl, fluorophenyl, bromophenyl, cyclopropyl, cyclobutyl, cyclopentyl, cyclohexyl and pyridyl.

7. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^6$ and $R^{6'}$ are each independently selected from hydrogen, unsubstituted C1-C6 acyclic alkyl, unsubstituted C3-C8 cycloalkyl, and C1-C6 acyclic alkyl substituted by 1-3 halogens.

8. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 7, wherein $R^6$ and $R^{6'}$ are each independently selected from the group consisting of hydrogen, methyl, ethyl, propyl, cyclopropyl, and cyclobutyl.

9. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^7$ is selected from the group consisting of hydrogen, unsubstituted C1-C6 acyclic alkyl, unsubstituted C1-C6 acyclic alkyl-C(=O)— and unsubstituted C2-C6 acyclic alkenyl-C(=O)—.

10. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 9, wherein $R^7$ is selected from the group consisting of hydrogen, methyl, ethyl, formyl, and acetyl.

11. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^8$ is selected from the group consisting of hydrogen, C1-C6 acyclic alkyl, and —OC(O)—C1—C12 acyclic alkyl; wherein the C1-C6 acyclic alkyl and —OC(O)—C1-C12 acyclic alkyl are optionally substituted by 1 to 3 substituents, wherein the substituents are independently selected from hydroxy, halo, cyano, amino, carboxy, C1-C6 acyclic alkyl and C1-C6 acyclic alkyl-O—.

12. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 11, wherein $R^8$ is selected from the group consisting of hydrogen, methyl, ethyl, propyl, butyl, pentyl, formyloxy, acetoxy, propionyloxy, butyryloxy and pentanoyloxy.

13. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein X is an oxygen atom.

14. A compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof, wherein the compound is selected from the group consisting of:

(6'-hydroxy-8'-oxo-8'H-spiro[cyclopropane-1,5'-indolizine]-7'-carbonyl)glycine;

(6'-hydroxy-8'-oxo-8'H-spiro[cyclopropane-1,5'-indolizine]-7'-carbonyl)-L-alanine;
(6'-hydroxy-8'-oxo-8'H-spiro[cyclopropane-1,5'-indolizine]-7'-carbonyl)-D-alanine;
(6-hydroxy-5,5-dimethyl-8-oxo-5,8-dihydroindolizin-7-carbonyl)glycine;
(6-hydroxy-5,5-dimethyl-8-oxo-5,8-dihydroindolizin-7-carbonyl)-L-alanine;
(6'-hydroxy-8'-oxo-8'H-spiro[cyclobutane-1,5'-indolizine]-7'-carbonyl)glycine;
(6'-hydroxy-8'-oxo-8'H-spiro[cyclobutane-1,5'-indolizine]-7'-carbonyl)-L-alanine;
(6'-hydroxy-8'-oxo-8'H-spiro[cyclopentane-1,5'-indolizine]-7'-carbonyl)glycine;
(6'-Hydroxy-8'-oxo-8'H-spiro[cyclopentane-1,5'-indolizine]-7'-carbonyl)glycine methyl ester;
(6'-Hydroxy-8'-oxo-8'H-spiro[cyclopentane-1,5'-indolizine]-7'-carbonyl)glycine ethyl ester;
(6'-hydroxy-8'-oxo-8'H-spiro[cyclopentane-1,5'-indolizine]-7'-carbonyl)-L-alanine;
(6'-hydroxy-8'-oxo-8'H-spiro[cyclopentane-1,5'-indolizine]-7'-carbonyl)-D-alanine;
(6'-hydroxy-8'-oxo-8'H-spiro[cyclohexane-1,5'-indolizine]-7'-carbonyl)glycine;
(6'-hydroxy-8'-oxo-8'H-spiro[cyclohexane-1,5'-indolizine]-7'-carbonyl)-L-alanine;
(3'-cyclobutyl-6'-hydroxy-8'-oxo-8'H-spiro[cyclopentane-1,5'-indolizine]-7'-carbonyl) glycine;
(3'-cyclopropyl-6'-hydroxy-8'-oxo-8'H-spiro[cyclopentane-1,5'-indolizine]-7'-carbonyl) glycine;
(6'-hydroxy-3'-methyl-8'-oxo-8'H-spiro[cyclopentane-1,5'-indolizine]-7'-carbonyl)glycine;
(3'-(tert-butyl)-6'-hydroxy-8'-oxo-8'H-spiro[cyclopentane-1,5'-indolizine]-7'-carbonyl) glycine;
(3'-cyclopentyl-6'-hydroxy-8'-oxo-8'H-spiro[cyclopentane-1,5'-indolizine]-7'-carbonyl) glycine;
(3'-cyclohexyl-6'-hydroxy-8'-oxo-8'H-spiro[cyclopentane-1,5'-indolizine]-7'-carbonyl) glycine;
(6'-hydroxy-8'-oxo-8'H-spiro[cyclopentane-1,5'-indolizine]-7'-carbonyl)-L-alanine ethyl ester;
(((6'-hydroxy-8'-oxo-8'H-spiro[cyclohexane-1,5'-indolizine]-7'-carbonyl)glycyloxy)) methyl pivalate;
(6'-hydroxy-8'-oxo-3'-(pyridin-3-yl)-8'H-spiro[cyclopentane-1,5'-indolizine]-7'-carbonyl) glycine;
(6'-hydroxy-8'-oxo-3'-phenyl-8'H-spiro[cyclopentane-1,5'-indolizine]-7'-carbonyl)glycine;
(3'-(4-fluorophenyl)-6'-hydroxy-8'-oxo-8'H-spiro[cyclopentane-1,5'-indolizine]-7'-carbonyl) glycine (3'-(4-chlorophenyl)-6'-hydroxy-8'-oxo-8'H-spiro[cyclopentane-1,5'-indolizine]-7'-carbonyl) glycine (3'-(4-chlorophenyl)-6'-hydroxy-8'-oxo-8'H-spiro [cyclopentane-1,5'-indolizine]-7'-carbonyl) -L-alanine;
(6'-hydroxy-3'-(4-methoxyphenyl)-8'-oxo-8'H-spiro[cyclopentane-1,5'-indolizine]-7'-carbonyl glycine;
(6'-hydroxy-8'-oxo-3'-(4-methylphenyl)-8'H-spiro[cyclopentane-1,5'-indolizine]-7'-carbonyl) glycine (3'-cyclopropyl-6'-hydroxy-8'-oxo-8'H-spiro[cyclohexane-1,5'-indolizine]-7'-carbonyl)glycine;
(3'-tert-butyl-6'-hydroxy-8'-oxo-8'H-spiro[cyclohexane-1,5'-indolizine]-7'-carbonyl)glycine;
(6'-hydroxy-3'-methyl-8'-oxo-8'H-spiro[cyclohexane-1,5'-indolizine]-7'-carbonyl)glycine;
(3'-(4-chlorophenyl)-6'-hydroxy-8'-oxo-8'H-spiro[cyclopentane-1,5'-indolizine]-7'-carbonyl) -D-alanine;
(3'-cyclobutyl-6'-hydroxy-8'-oxo-8'H-spiro[cyclohexane-1,5'-indolizine]-7'-carbonyl) glycine;
(6'-hydroxy-8'-oxo-3'-phenyl-8'H-spiro[cyclohexane-1,5'-indolizine]-7'-carbonyl)glycine;
(3'-(4-chlorophenyl)-6'-hydroxy-8'-oxo-8'H-spiro[cyclohexane-1,5'-indolizine]-7'-carbonyl) glycine (3'-(4-fluorophenyl)-6'-hydroxy-8'-oxo-8'H-spiro[cyclohexane-1,5'-indolizine]-7'-carbonyl) glycine (6'-hydroxy-3'-(4-methoxyphenyl)-8'-oxo-8'H-spiro [cyclohexane-1,5'-indolizine]-7'-carbonyl glycine;
(6'-hydroxy-8'-oxo-3'-phenyl-8'H-spiro[cyclobutane-1,5'-indolizine]-7'-carbonyl)glycine;
(6'-hydroxy-8'-oxo-3'-phenyl-8'H-spiro[cyclopropane-1,5'-indolizine]-7'-carbonyl)glycine;
(6-hydroxy-5,5-dimethyl-8-oxo-3-phenyl-5,8-dihydroindolizin-7-carbonyl)glycine;
(6'-hydroxy-8'-oxo-3'-phenyl-8'H-spiro[cyclopentane-1,5'-indolizine]-7'-carbonyl)-L-alanine;
(6-hydroxy-8-oxo-3-phenyl-2',3',5',6'-tetrahydro-8H-spiro[indolizin-5,4'-pyran]-7-carbonyl)glycine;
(6'-hydroxy-8'-oxo-3'-phenyl-8'H-spiro[cyclopentane-1,5'-indolizine]-7'-carbonyl)-D-alanine;
(6-hydroxy-8-oxo-2',3',5',6'-tetrahydro-8H-spiro[indolizin-5,4'-pyran]-7-carbonyl)glycine;
(6'-hydroxy-8'-oxo-8'H-spiro[cyclohexane-1,5'-indolizine]-7'-carbonyl)glycine ethyl ester;
(3'-(4-fluorophenyl)-6'-hydroxy-8'-oxo-8'H-spiro[cyclopentane-1,5'-previous]-7'-carbonyl) glycine ethyl ester
(6'-hydroxy-8'-oxo-3'-phenyl-8'H-spiro[cyclohexane-1,5'-indolizine]-7'-carbonyl)glycine-2,2-dideuterium (6'-Hydroxy-8'-oxo-3'-(phenyl-4-hydra)-8'H-spiro[cyclohexane-1,5'-indolizine]-7'-carbonyl) glycine (3'-(4-Chlorophenyl)-6'-hydroxy-8'-oxo-8'H-spiro [cyclopentane-1,5'-indolizine]-7'-carbonyl) glycine methyl ester;
(3'-(4-fluorophenyl)-6'-hydroxy-8'-oxo-8'H-spiro[cyclopentane-1,5'-indolizine]-7'-carbonyl) glycine methyl ester;
(1'-cyclopropyl-6'-hydroxy-8'-oxo-8'H-spiro[cyclohexane-1,5'-indolizine]-7'-carbonyl) glycine;
(2'-cyclopropyl-6'-hydroxy-8'-oxo-8'H-spiro[cyclohexane-1,5'-indolizine]-7'-carbonyl) glycine;
(6'-hydroxy-8'-oxo-1'-phenyl-8'H-spiro[cyclohexane-1,5'-indolizine]-7'-carbonyl)glycine;
(6'-hydroxy-8'-oxo-2'-phenyl-8'H-spiro[cyclohexane-1,5'-indolizine]-7'-carbonyl)glycine;
(1'-(4-fluorophenyl)-6'-hydroxy-8'-oxo-8'H-spiro[cyclohexane-1,5'-indolizine]-7'-carbonyl) glycine (2'-(4-fluorophenyl)-6'-hydroxy-8'-oxo-8'H-spiro[cyclohexane-1,5'-indolizine]-7'-carbonyl) glycine (1'-(4-chlorophenyl)-6'-hydroxy-8'-oxo-8'H-spiro [cyclohexane-1,5'-indolizine]-7'-carbonyl) glycine (2'-(4-chlorophenyl)-6'-hydroxy-8'-oxo-8'H-spiro [cyclohexane-1,5'-indolizine]-7'-carbonyl) glycine (6'-hydroxy-1'-(4-methoxyphenyl)-8'-oxo-8'H-spiro [cyclohexane-1,5'-indolizine]-7'-carbonyl glycine;
(6'-hydroxy-2'-(4-methoxyphenyl)-8'-oxo-8'H-spiro[cyclohexane-1,5'-indolizine]-7'-carbonyl glycine;
(1'-cyclopropyl-6'-hydroxy-8'-oxo-8'H-spiro[cyclopentane-1,5'-indolizine]-7'-carbonyl) glycine;
(2'-cyclopropyl-6'-hydroxy-8'-oxo-8'H-spiro[cyclopentane-1,5'-indolizine]-7'-carbonyl) glycine;
(6'-hydroxy-8'-oxo-1'-phenyl-8'H-spiro[cyclopentane-1,5'-indolizine]-7'-carbonyl)glycine;
(6'-hydroxy-8'-oxo-2'-phenyl-8'H-spiro[cyclopentane-1,5'-indolizine]-7'-carbonyl)glycine;
(6'-hydroxy-8'-oxo-1'-phenyl-8'H-spiro[cyclopentane-1,5'-indolizine]-7'-carbonyl)-L-alanine;

(6'-hydroxy-8'-oxo-8'H-spiro[cycloheptane-1,5'-indolizine]-7'-carbonyl)glycine;

((1,4-trans)-6'-hydroxy-4-methyl-8'-oxo-8'H-spiro[cyclohexane-1,5'-indolizine]-7'—carbonyl)glycine;

((1,4-cis)-6'-hydroxy-4-methyl-8'-oxo-8'H-spiro[cyclohexane-1,5'-indolizine]-7'—carbonyl)glycine;

(6'-hydroxy-8'-oxo-1'-phenyl-8'H-spiro[cyclobutane-1,5'-indolizine]-7'-carbonyl)glycine;

(6'-hydroxy-8'-oxo-2'-phenyl-8'H-spiro[cyclobutane-1,5'-indolizine]-7'-carbonyl)glycine;

(6'-hydroxy-8'-oxo-3'-phenyl-8'H-spiro[cyclopentane-1,5'-indolizine]-7'-carbonyl)glycine-2,2-di-deuterium (6'-hydroxy-3'-(4-hydroxyphenyl)-8'-oxo-8'H-spiro[cyclopentane-1,5'-indolizine]-7'-carbonyl)glycine;

(6'-hydroxy-3'-(2-methoxyphenyl)-8'-oxo-8'H-spiro[cyclopentane-1,5'-indolizine]-7'-carbonyl glycine; and (6'-hydroxy-3'-(3-methoxyphenyl)-8'-oxo-8'H-spiro[cyclopentane-1,5'-indolizine]-7'-carbonyl glycine.

15. A pharmaceutical composition comprising a compound of formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, and one or more pharmaceutically acceptable carriers, adjuvants or excipients.

* * * * *

UNITED STATES PATENT AND TRADEMARK OFFICE
CERTIFICATE OF CORRECTION

PATENT NO. : 11,021,478 B2  
APPLICATION NO. : 16/611838  
DATED : June 1, 2021  
INVENTOR(S) : Liu et al.

Page 1 of 1

It is certified that error appears in the above-identified patent and that said Letters Patent is hereby corrected as shown below:

In the Specification

In Column 3, Line 31, please replace "=O, =S, –SH, $R^{15}S–$, $R^{15}$ (O=) S–" with ----=O, =S, –SH, $R^{15}O–$, $R^{15}S–$, $R^{15}$ (O=) S– --- and In Column 4, Line 36, please replace "$R^{11}O–$, $R^{11}$ (O=) S–" with ---$R^{11}O–$, $R^{11}S–$, $R^{11}$ (O=) S– ---.

Signed and Sealed this  
Ninth Day of November, 2021

Drew Hirshfeld  
*Performing the Functions and Duties of the  
Under Secretary of Commerce for Intellectual Property and  
Director of the United States Patent and Trademark Office*